(12) United States Patent
Berthelette et al.

(10) Patent No.: US 8,685,999 B2
(45) Date of Patent: Apr. 1, 2014

(54) BETA CARBOLINE SULPHONYLUREA DERIVATIVES AS EP4 RECEPTOR ANTAGONISTS

(75) Inventors: Carl Berthelette, Laval (CA); Michael Boyd, Saint-Lazare (CA); Jason Burch, Redwood City, CA (US); Claude Dufresne, Dollard-des-Ormeaux (CA); Julie Farand, Jersey City, NJ (US); Yongxin Han, Kirkland (CA); Claudio F. Sturino, Ile-Bizard (CA)

(73) Assignee: Merck Sharp & Dohme Corp., Rahway, NJ (US)

( * ) Notice: Subject to any disclaimer, the term of this patent is extended or adjusted under 35 U.S.C. 154(b) by 299 days.

(21) Appl. No.: 13/120,786

(22) PCT Filed: Sep. 22, 2009

(86) PCT No.: PCT/CA2009/001330
§ 371 (c)(1),
(2), (4) Date: Jul. 27, 2011

(87) PCT Pub. No.: WO2010/034110
PCT Pub. Date: Apr. 1, 2010

(65) Prior Publication Data
US 2011/0275660 A1     Nov. 10, 2011

Related U.S. Application Data

(60) Provisional application No. 61/194,144, filed on Sep. 25, 2008.

(51) Int. Cl.
*C07D 471/04*  (2006.01)
*A61K 31/437*  (2006.01)

(52) U.S. Cl.
USPC .......................................... 514/292; 546/81

(58) Field of Classification Search
USPC ............................................ 514/292; 546/81
See application file for complete search history.

(56) References Cited

FOREIGN PATENT DOCUMENTS

| | | |
|---|---|---|
| CA | 2416867 A1 | 1/2002 |
| CA | 2426457 A1 | 4/2002 |
| CA | 2471952 A1 | 7/2003 |
| CA | 2481532 A1 | 10/2003 |
| CA | 2600510 A1 | 9/2006 |
| CA | 2681146 A1 | 10/2008 |
| WO | WO2006/122403 A1 | 11/2006 |

*Primary Examiner* — Rita Desai
(74) *Attorney, Agent, or Firm* — Maria V. Marucci; Valerie J. Camara

(57) ABSTRACT

The invention is directed to β-carboline sulphonylurea derivatives as EP4 receptor antagonists useful for the treatment of EP4 mediated diseases or conditions, such as acute and chronic pain, inflammation, osteoarthritis, and rheumatoid arthritis. Pharmaceutical compositions and methods of use are also included.

17 Claims, No Drawings

BETA CARBOLINE SULPHONYLUREA DERIVATIVES AS EP4 RECEPTOR ANTAGONISTS

CROSS REFERENCE TO RELATED APPLICATIONS

This application is a U.S. National Phase application under 35 U.S.C. §371 of PCT Application No. PCT/CA2009/001330, filed Sep. 22, 2009, which claims priority under 35 U.S.C. §119(e) from U.S. Provisional Application Ser. No. 61/194,144, filed Sep. 25, 2008.

BACKGROUND OF THE INVENTION

This invention relates to compounds and methods for treating prostaglandin E mediated diseases, and certain pharmaceutical compositions thereof. More particularly, the compounds of the invention are structurally different from NSAIDs and opiates, and are antagonists of the pain and inflammatory effects of E-type prostaglandins.

Three review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154; Journal of Lipid Mediators and Cell Signaling, 1996, 14, 83-87; and Prostaglandins and Other Lipid Mediators, 2002, 69, 557-573.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, have effects on vascular homeostasis, reproduction, gastrointestinal functions and bone metabolism. These compounds may have a diminished ability to induce some of the mechanism-based side effects of NSAIDs which are indiscriminate cyclooxygenase inhibitors. In particular, the compounds are believed to have a reduced potential for gastrointestinal toxicity, a reduced potential for renal side effects, a reduced effect on bleeding times and a lessened ability to induce asthma attacks in aspirin-sensitive asthmatic subjects.

In The Journal of Clinical Investigation (2002, 110, 651-658), studies suggest that chronic inflammation induced by collagen antibody injection in mice is mediated primarily through the EP4 subtype of $PGE_2$ receptors. Patent publications U.S. Pat. No. 5,965,741 (Oct. 12, 1999), U.S. Pat. No. 5,811,459 (Sep. 22, 1998) and EP 0752421-B1 (Oct. 12, 2005) disclose compounds as being useful in the treatment of prostaglandin mediated diseases.

The present invention is directed to novel compounds that are antagonists of the EP4 subtype of $PGE_2$ receptors. The compounds would therefore be useful for the treatment of diseases or conditions mediated by the EP4 receptor, such as acute and chronic pain, inflammation, osteoarthritis, and rheumatoid arthritis.

SUMMARY OF THE INVENTION

The invention is directed to β-carboline sulphonylurea derivatives of Formula I as EP4 receptor antagonists useful for the treatment of EP4 mediated diseases or conditions, such as acute and chronic pain, inflammation, osteoarthritis, and rheumatoid arthritis. Pharmaceutical compositions and methods of use are also included.

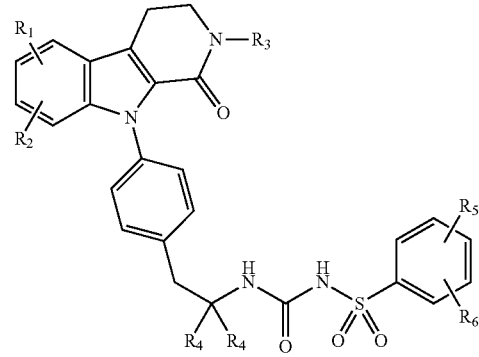

Formula I

DETAILED DESCRIPTION OF THE INVENTION

The invention encompasses a genus of compounds of Formula I

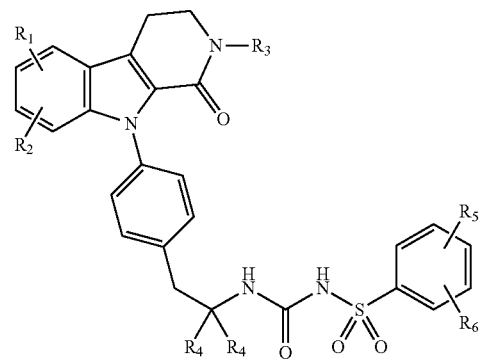

Formula I or a pharmaceutically acceptable salt thereof, wherein:

x is 0, 1, or 2;
y is 0, 1, or 2;
n is 1, 2, 3, 4, 5 or 6;
$R_1$, $R_2$ are each independently selected from hydrogen, halogen, $C_{1-6}$ alkyl, $C_{3-6}$ cycloalkyl, aryl, heteroaryl, $NR_aR_b$, $S(O)_xR_a$, $C(O)_yR_a$, and $OR_a$, wherein said alkyl, cycloalkyl, aryl, and heteroaryl are optionally substituted with one or more substituents $R_7$;
$R_3$ is selected from hydrogen, $C_{1-6}$ alkyl, $C_{3-6}$ cycloalkyl, aryl, and heteroaryl, wherein said alkyl, cycloalkyl, aryl, and heteroaryl are optionally substituted with one or more substituents $R_7$;
$R_4$ are each independently selected from hydrogen, and $(CH_2)_n$, optionally two $R_4$ can join together for form a 3 to 6 membered ring;
$R_5$, $R_6$ are each independently selected from hydrogen, halogen, $C_{1-6}$ alkyl, $C_{3-6}$ cycloalkyl, aryl, heteroaryl, $NR_aR_b$, $S(O)_xR_a$, and $OR_a$, wherein said alkyl, cycloalkyl, aryl, and heteroaryl are optionally substituted with one or more substituents $R_7$;
$R_a$, $R_b$ are each independently selected from hydrogen, $C_{1-6}$ alkyl, $C_{3-10}$ cycloalkyl, aryl, heterocyclyl, wherein said alkyl, cycloalkyl, aryl and heterocyclyl are optionally substituted with one or more substituents $R_7$; and
$R_7$ is selected from hydroxy, aryl, heterocyclyl, halogen, —$C_{1-6}$ alkyl, $C_{1-6}$ alkoxy, hydrogen, $CO_2H$, cyano, $O(C=O)C_{1-6}$ alkyl, $OC_{1-6}$ alkyl, $NO_2$, trifluoromethoxy, trifluoroethoxy, $-O(C_{1-10})$ perfluoroalkyl, $(C_{1-10})$ perfluoroalkyl, $C_{1-10}$ alkylaminocarbonylamino, aminocarbonylamino, $C_{1-10}$ alkyloxycarbonylamino$C_{1-10}$ alkyl, oxycarbonylamino, oxycarbonylamino$C_{1-10}$ alkyl, $C_{1-10}$ alkyloxycarbonylamino, $C_{1-10}$ alkylcarbonylamino$C_{1-10}$ alkyl, carbonylamino$C_{1-10}$ alkyl, $C_{1-10}$ alkylcarbonylamino, carbonylamino, $C_{1-10}$ alkylaminosulfonylamino$C_{1-10}$ alkyl, aminosulfonylamino$C_{1-10}$ alkyl, $C_{1-10}$ alkylaminosulfonylamino, aminosulfonylamino, $C_{1-10}$ alkylsulfonylamino$C_{1-10}$ alkyl, $C_{1-10}$ alkylsulfonylamino, sulfonylamino$C_{1-10}$ alkyl, sulfonylamino, $C_{1-10}$ alkylsulfonyl, sulfonyl, $C_{1-10}$ alkylaminosulfonyl, aminosulfonyl, $C_{1-10}$ alkylaminocarbonyl, aminocarbonyl, $-(C=O)N(C_{0-6}$ alkyl$)_2$, $-S(C_{0-6}$ alkyl$)$, and $NH_2$.

Within the genus, the invention encompasses a sub-genus of compounds wherein $R_1$, $R_2$ are each independently selected from hydrogen, halogen, $C_{1-4}$ alkyl, $C_{3-6}$ cycloalkyl, aryl, heteroaryl, $C(O)_yRa$, and $S(O)_xRa$, wherein said aryl and heteroaryl groups are optionally substituted with one or more $R_7$.

Within the sub-genus, the invention encompasses a class of compounds wherein $R_3$ is selected from hydrogen, $C_1$-$C_6$ alkyl, $C_3$-$C_6$ cycloalkyl, and aryl.

Within the class, the invention encompasses a sub-class of compounds wherein $R_4$ is independently selected from hydrogen, and $(CH_2)_n$ where n is 1-3, optionally the two $R_4$ join together to form a 3-6 membered ring. In a variant of this embodiment, the two $R_4$ join together to form a 3-6 membered ring.

Within the sub-class, the invention encompasses a family of compounds wherein $R_5$, $R_6$ are each independently selected from hydrogen, halogen, $C_{1-6}$ alkyl, $C_{3-6}$ cycloalkyl, and $OC_{1-4}$ alkyl.

Within the family, the invention encompasses a sub-family of compounds wherein $R_7$ is selected from hydrogen, halogen, $C_1$-$C_4$ alkyl, and phenyl.

In another embodiment, the invention encompasses a second sub-genus of compounds wherein $R_1$, $R_2$ are each independently selected from hydrogen, methyl, cyclopropyl, chlorine, bromine, phenyl, pyridyl, thienyl (or thiophenyl), pyrazolyl, oxadiazolyl, $C(O)_yRa$, and $S(O)_xRa$, wherein said phenyl and oxadiazolyl are optionally substituted with one or more $R_7$.

Within the second sub-genus, the invention encompasses a class of compounds wherein $R_3$ is selected from hydrogen, methyl, ethyl, cyclopropyl, cyclopropylmethyl, and phenyl.

Within the class, the invention encompasses a sub-class of compounds wherein $R_4$ is independently selected from hydrogen, and $(CH_2)_n$, optionally the two $R_4$ join together to form a 3-6 membered ring. In a variant of this embodiment, the two $R_4$ join together to form a 3 membered ring.

Within the sub-class, the invention encompasses a family of compounds wherein $R_5$, $R_6$ are each independently selected from hydrogen, chlorine, methyl, and methoxyl.

Within the family, the invention encompasses a sub-family of compounds wherein $R_a$, $R_b$ are each independently selected from hydrogen, methyl, ethyl, and phenyl.

Within the sub-family, the invention encompasses illustrating compounds wherein $R_7$ is selected from hydrogen, methyl, fluorine, and phenyl.

In another embodiment of the invention, $R_1$, $R_2$ are each independently selected from hydrogen, halogen, $C_{1-3}$ alkyl, cyclopropyl, phenyl, benzyl, pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl, $C(O)_yRa$, and $S(O)_xRa$, wherein said phenyl and oxadiazolyl are optionally substituted with one or more $R_7$.

In another aspect of the invention, $R_1$, $R_2$ are each independently selected from hydrogen, methyl, ethyl, cyclopropyl, chlorine, bromine, fluorine, phenyl, benzyl, pyridyl, pyrazinyl, pyrimidinyl, pyridazinyl, thienyl (or thiophenyl), thiazolyl, pyrazolyl, oxazolyl, oxadiazolyl, thiazolyl, $C(O)_yRa$, and $S(O)_xRa$, wherein said phenyl and oxadiazolyl are optionally substituted with one or more $R_7$.

In a further aspect of the invention, $R_1$, $R_2$ are each independently selected from hydrogen, methyl, cyclopropyl, chlorine, bromine, phenyl, pyridyl, thienyl (or thiophenyl), pyrazolyl, oxadiazolyl, $C(O)_yRa$, and $S(O)_xRa$, wherein said phenyl and oxadiazolyl are optionally substituted with one or more $R_7$.

In another embodiment of the invention, $R_3$ is selected from hydrogen, $C_{1-6}$ alkyl, $C_{3-6}$ cycloalkyl, and aryl.

In another aspect of the invention, $R_3$ is selected from hydrogen, methyl, ethyl, cyclopropyl, cyclopropylmethyl, and phenyl.

In another embodiment of the invention $R_4$ is independently selected from hydrogen, and $(CH_2)_n$ where n is 1-3, $R_4$ is independently selected from hydrogen, and $(CH_2)_n$ where n is 1-3, optionally the two $R_4$ join together to form a 3 membered ring.

In another embodiment of the invention, $R_5$, $R_6$ are each independently selected from hydrogen, halogen, $C_{1-6}$ alkyl, $C_{3-6}$ cycloalkyl, and $OC_{1-4}$ alkyl.

In another aspect of the invention, $R_5$, $R_6$ are each independently selected from hydrogen, chlorine, bromine, fluorine, methyl, ethyl, cyclopropyl, methoxyl, and ethoxyl.

In a further aspect of the invention, $R_5$, $R_6$ are each independently selected from hydrogen, chlorine, methyl, and methoxyl.

In another embodiment of the invention, $R_a$, $R_b$ are each independently selected from hydrogen, methyl, ethyl, and phenyl.

In another embodiment of the invention, $R_7$ is selected from hydrogen, halogen, $C_{1-4}$ alkyl, and phenyl.

In another aspect of the invention, $R_7$ is selected from hydrogen, methyl, fluorine, and phenyl.

In another embodiment of the two $R_4$ join together to form a 3-6 membered ring. In a variant of this embodiment, the two $R_4$ join together to form a 3 membered ring.

Illustrative but non-limiting examples of the invention are the following:

4-chloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;

4-methyl-N-[({2-[4-(2,5,7-trimethyl-1-oxo-1,2,3,4-tetrahydro-9H-beta-carbolin-9-yl)phenyl]ethyl}amino)carbonyl]benzenesulfonamide;

4-chloro-N-[({2-[4-(5,7-dichloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(6-chloro-2-methyl-1-oxo-1,2,3,4-tetrahydro-9H-beta-carbolin-9-yl)phenyl]ethyl}amino)carbonyl]benzenesulfonamide;

N-[({2-[4-(6-bromo-2-methyl-1-oxo-1,2,3,4-tetrahydro-9H-beta-carbolin-9-yl)phenyl]ethyl}amino)carbonyl]-4-chlorobenzenesulfonamide;

4-chloro-N-[({2-[4-(5,7-dichloro-2-ethyl-1-oxo-1,2,3,4-tetrahydro-9H-beta-carbolin-9-yl)phenyl]ethyl}amino)carbonyl]benzenesulfonamide;

4-chloro-N-{[(2-{4-[5,7-dichloro-2-(cyclopropylmethyl)-1-oxo-1,2,3,4-tetrahydro-9H-beta-carbolin-9-yl]phenyl}ethyl)amino]carbonyl}benzenesulfonamide;

4-chloro-N-[({2-[4-(2-methyl-1-oxo-6-phenyl-1,2,3,4-tetrahydro-9H-beta-carbolin-9-yl)phenyl]ethyl}amino)carbonyl]benzenesulfonamide;

4-chloro-N-[({2-[4-(5,7-dichloro-1-oxo-2-phenyl-1,2,3,4-tetrahydro-9H-beta-carbolin-9-yl)phenyl]ethyl}amino)carbonyl]benzenesulfonamide;

4-chloro-N-[({2-[4-(6,7-dichloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5,6-dichloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(7-chloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5-chloro-2-methyl-1-oxo-1,2,3,4-tetrahydro-9H-beta-carbolin-9-yl)phenyl]ethyl}amino)carbonyl]benzenesulfonamide;

N-[({2-[4-(5-bromo-2-methyl-1-oxo-1,2,3,4-tetrahydro-9H-beta-carbolin-9-yl)phenyl]ethyl}amino)carbonyl]-4-chlorobenzenesulfonamide;

N-[({2-[4-(7-bromo-2-methyl-1-oxo-1,2,3,4-tetrahydro-9H-beta-carbolin-9-yl)phenyl]ethyl}amino)carbonyl]-4-chlorobenzenesulfonamide;

N-[({1-[4-(6-bromo-2-methyl-1-oxo-1,2,3,4-tetrahydro-9H-beta-carbolin-9-yl)benzyl]cyclopropyl}amino)carbonyl]-4-chlorobenzenesulfonamide;

4-chloro-N-[({2-[4-(2-methyl-1-oxo-5-phenyl-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-7-phenyl-1,2,3,4-tetrahydro-9H-beta-carbolin-9-yl)phenyl]ethyl}amino)carbonyl]benzenesulfonamide;

4-chloro-N-{[(2-{4-[6-(4-fluorophenyl)-2-methyl-1-oxo-1,2,3,4-tetrahydro-9H-beta-carbolin-9-yl]phenyl}ethyl)amino]carbonyl}benzenesulfonamide;

4-chloro-N-[({2-[4-(8-chloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-6-pyridin-3-yl-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-6-pyridin-2-yl-1,2,3,4-tetrahydro-9H-beta-carbolin-9-yl)phenyl]ethyl}amino)carbonyl]benzenesulfonamide;

4-chloro-N-{[(1-{4-[6-(2-fluorophenyl)-2-methyl-1-oxo-1,2,3,4-tetrahydro-9H-beta-carbolin-9-yl]benzyl}cyclopropyl)amino]carbonyl}benzenesulfonamide;

4-chloro-N-[({1-[4-(2-methyl-1-oxo-6-pyridin-3-yl-1,2,3,4-tetrahydro-9H-beta-carbolin-9-yl)benzyl]cyclopropyl}amino)carbonyl]benzenesulfonamide;

4-chloro-N-{[(1-{4-[2-methyl-1-oxo-6-(3-thienyl)-1,2,3,4-tetrahydro-9H-beta-carbolin-9-yl]benzyl}cyclopropyl)amino]carbonyl}benzenesulfonamide;

4-chloro-N-[({1-[4-(2-methyl-1-oxo-6-pyridin-2-yl-1,2,3,4-tetrahydro-9H-beta-carbolin-9-yl)benzyl]cyclopropyl}amino)carbonyl]benzenesulfonamide;

4-chloro-N-{[(1-{4-[2-methyl-6-(2-methylphenyl)-1-oxo-1,2,3,4-tetrahydro-9H-beta-carbolin-9-yl]benzyl}cyclopropyl)amino]carbonyl}benzenesulfonamide;

4-chloro-N-[({1-[4-(2,5,7-trimethyl-1-oxo-1,2,3,4-tetrahydro-9H-beta-carbolin-9-yl)benzyl]cyclopropyl}amino)carbonyl]benzenesulfonamide;

2,6-dichloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;

2,6-dimethoxy-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;

4-chloro-N-[({1-[4-(6-cyclopropyl-2-methyl-1-oxo-1,2,3,4-tetrahydro-9H-beta-carbolin-9-yl)benzyl]cyclopropyl}amino)carbonyl]benzenesulfonamide;

4-chloro-N-[({2-[4-(6-cyclopropyl-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5-cyclopropyl-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(7-cyclopropyl-2-methyl-1-oxo-1,2,3,4-tetrahydro-9H-beta-carbolin-9-yl)phenyl]ethyl}amino)carbonyl]benzenesulfonamide;

sodium[(4-chlorophenyl)sulfonyl]{[(1-{4-[2-methyl-6-(5-methyl-1,3,4-oxadiazol-2-yl)-1-oxo-1,2,3,4-tetrahydro-9H-beta-carbolin-9-yl]benzyl}cyclopropyl)amino]carbonyl}azanide;

4-chloro-N-{[(2-{4-[2-methyl-6-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(2-{4-[2-methyl-7-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(2-{4-[2-methyl-5-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(1-{4-[2-methyl-6-(methylsulfonyl)-1-oxo-1,2,3,4-tetrahydro-9H-beta-carbolin-9-yl]benzyl}cyclopropyl)amino]carbonyl}benzenesulfonamide;

4-chloro-N-({[2-(4-{2-methyl-6-[4-(methylsulfonyl)phenyl]-1-oxo-1,2,3,4-tetrahydro-9H-beta-carbolin-9-yl}phenyl)ethyl]amino}carbonyl)benzenesulfonamide;

4-chloro-N-({[2-(4-{2-methyl-6-[3-(methylsulfonyl)phenyl]-1-oxo-1,2,3,4-tetrahydro-9H-beta-carbolin-9-yl}phenyl)ethyl]amino}carbonyl)benzenesulfonamide;

methyl 9-[4-({1-[({[(4chlorophenyl)sulfonyl]amino}carbonyl)amino]cyclopropyl}methyl)phenyl]-2-methyl-1-oxo-2,3,4,9-tetrahydro-1H-beta-carboline-6-carboxylate;

9-[4-({1-[({[(4-chlorophenyl)sulfonyl]amino}carbonyl)amino]cyclopropyl}methyl)phenyl]-2-methyl-1-oxo-2,3,4,9-tetrahydro-1H-beta-carboline-6-carboxylic acid;

4-chloro-N-{[(1-{4-[2-methyl-1-oxo-6-(1H-pyrazol-5-yl)-1,2,3,4-tetrahydro-9H-beta-carbolin-9-yl]benzyl}cyclopropyl)amino]carbonyl}benzenesulfonamide;

4-chloro-N-{[(1-{4-[2-methyl-1-oxo-6-(5-phenyl-1,3,4-oxadiazol-2-yl)-1,2,3,4-tetrahydro-9H-beta-carbolin-9-yl]benzyl}cyclopropyl)amino]carbonyl}benzenesulfonamide;

4-chloro-N-{[(1-{4-[2-methyl-1-oxo-6-(phenylsulfonyl)-1,2,3,4-tetrahydro-9H-beta-carbolin-9-yl]benzyl}cyclopropyl)amino]carbonyl}benzenesulfonamide; and pharmaceutically acceptable salts and solvates thereof.

The invention also encompasses a pharmaceutical composition comprising a compound of Formula I in admixture with one or more physiologically acceptable carriers or excipients.

The invention also encompasses a compound of Formula I or a pharmaceutically acceptable derivative thereof for use in human or veterinary medicine.

The invention also encompasses a method of treating a human or animal subject suffering from a condition which is mediated by the action of PGE$_2$ at EP4 receptors, which method comprises administering to said subject an effective amount of a compound of Formula I.

The invention also encompasses the use of a compound of Formula I for the manufacture of a therapeutic agent for the treatment of a condition which is mediated by the action of PGE$_2$ at EP4 receptors.

The invention also encompasses a method for treating acute or chronic pain, migraine, inflammation, osteoarthritis, rheumatoid arthritis, juvenile rheumatoid arthritis, gout, bursitis, ankylosing spondylitis, primary dysmenorrheal, or atherosclerosis in a patient in need thereof comprising administering to the patient a therapeutically effective amount of a compound of Formula I or a pharmaceutically acceptable salt thereof.

DEFINITIONS

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes all of the hexyl alkyl and pentyl alkyl isomers as well as n-, iso-, sec- and t-butyl, n- and isopropyl, ethyl and methyl. "C$_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-C$_4$ alkylene-B" represents A-CH$_2$-CH$_2$-CH$_2$-CH$_2$-B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, C$_{1-20}$ alkyl, CF$_3$, NH$_2$, N(C$_{1-6}$ alkyl)$_2$, NO$_2$, oxo, CN, N$_3$, —OH, —O(C$_{1-6}$ alkyl), C$_{3-10}$ cycloalkyl, C$_{2-6}$ alkenyl, C$_{2-6}$ alkynyl, (C$_{0-6}$ alkyl) S(O)$_{0-2}$—, (C$_{0-6}$ alkyl) S(O)$_{0-2}$(C$_{0-6}$ alkyl)-, (C$_{0-6}$ alkyl)C(O)NH—, H$_2$N—C(NH)—, —O(C$_{1-6}$ alkyl)CF$_3$, (C$_{0-6}$ alkyl)C(O)—, (C$_{0-6}$ alkyl)OC(O)—, (C$_{0-6}$ alkyl)O(C$_{1-6}$ alkyl)-, (C$_{0-6}$ alkyl)C(O)$_{1-2}$(C$_{0-6}$ alkyl)-, (C$_{0-6}$ alkyl)OC(O)NH—, —NH(C$_{1-6}$ alkyl)NHC(O)NH(C$_{1-6}$ alkyl), NHC(O)OC$_{1-6}$ alkyl, —NH(C$_{1-6}$ alkyl)NHSO$_2$(C$_{1-6}$ alkyl), —(C$_{0-6}$ alkyl)NHSO$_2$(C$_{1-6}$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "C$_0$" as employed in expressions such as "C$_{0-6}$ alkyl" means a direct covalent bond; or when the term appears at the terminus of a substituent, C$_{0-6}$ alkyl means hydrogen or C$_{1-6}$alkyl. Similarly, when an integer defining the presence of a certain number of atoms in a group is equal to zero, it means that the atoms adjacent thereto are connected directly by a bond. For example, in the structure

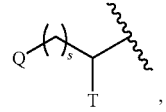

wherein s is an integer equal to zero, 1 or 2, the structure is

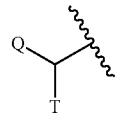

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

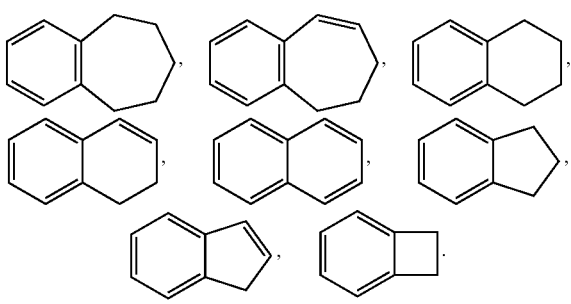

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azabenzimidazole, benzoimidazolyl, benzofuranyl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuranyl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, tetrahidroquinolinyl, 2,3-dihydrobenzofuranyl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

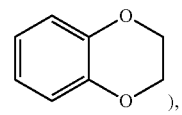), imidazo(2,1-b)(1,3)thiazole, (i.e.,

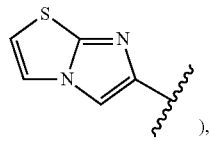 [SMILES: *c1cn2ccsc2n1]), and benzo-1,3-dioxolyl (i.e.,

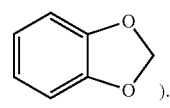).

In certain contexts herein,

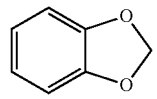

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_{3-10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_{1-20}$ alkyl, $CF_3$, $NH_2$, $N(C_{1-6}$ alkyl$)_2$, $NO_2$, oxo, CN, $N_3$, —OH, —O($C_{1-6}$ alkyl), $C_{3-10}$ cycloalkyl, $C_{2-6}$ alkenyl, $C_{2-6}$ alkynyl, ($C_{0-6}$ alkyl) S(O)$_{0-2}$—, aryl-S(O)$_{0-2}$—, ($C_{0-6}$ alkyl)S(O)$_{0-2}$($C_{0-6}$ alkyl)-, ($C_{0-6}$ alkyl)C(O)NH—, $H_2$N—C(NH)—, —O($C_{1-6}$ alkyl)$CF_3$, ($C_{0-6}$ alkyl)C(O)—, ($C_{0-6}$ alkyl)OC(O)—, ($C_{0-6}$ alkyl)$_2$NC(O)—, ($C_{0-6}$alkyl)O($C_{1-6}$ alkyl)-, ($C_{0-6}$ alkyl)C(O)$_{1-2}$($C_{0-6}$ alkyl)-, ($C_{0-6}$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . .") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

It will be understood that, as used herein, references to the compounds of Formula I are meant to also include the pharmaceutically acceptable salts.

Utilities

The compounds of the invention are antagonists of the EP4 receptor and are therefore useful in treating EP4 receptor mediated diseases.

In view of their ability to bind to the EP4 receptor, the compounds of the invention are useful in the treatment of the disorders that follow. Thus, the compounds of the invention are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesias), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, CORD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of the invention are also useful in the treatment of immunological diseases such as autoimmune diseases, immunological deficiency diseases or organ transplantation. The compounds of the invention are also effective in increasing the latency of HIV infection.

The compounds of the invention are also useful in the treatment of diseases of abnormal platelet function (e.g. occlusive vascular diseases).

The compounds of the invention are also useful for the preparation of a drug with diuretic action.

The compounds of the invention are also useful in the treatment of impotence or erectile dysfunction.

The compounds of the invention are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect, compounds of the invention may be useful in inhibiting bone resorption and/or promoting bone generation.

The compounds of the invention are also useful for attenuating the hemodynamic side effects of NSAIDs and COX-2 inhibitors.

The compounds of the invention are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of the invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, and motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula I are also useful in the treatment of neuroprotection and in the treatment of neurodegeneration following stroke, cardiac arrest, pulmonary bypass, traumatic brain injury, spinal cord injury or the like.

The compounds of the invention are also useful in the treatment of tinnitus.

The compounds of the invention are also useful in preventing or reducing dependence on, or preventing or reducing tolerance or reverse tolerance to, a dependence—inducing agent. Examples of dependence inducing agents include opioids (e.g. morphine), CNS depressants (e.g. ethanol), psychostimulants (e.g. cocaine) and nicotine.

The compounds of the invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of the invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

The compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium, cervix, prostate, thyroid and brain.

It is to be understood that reference to treatment includes both treatment of established symptoms and prophylactic treatment, unless explicitly stated otherwise.

Dose Ranges

The magnitude of prophylactic or therapeutic dose of a compound of Formula I will, of course, vary with the nature and severity of the condition to be treated, and with the particular compound of Formula I used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I per kg of body weight per day.

In the case where an oral composition is employed, a suitable dosage range is, e.g. from about 0.01 mg to about 100 mg of a compound of Formulas I per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I per kg of body weight per day.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefore, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: COX-2 inhibitors, such as celecoxib, rofecoxib, etoricoxib, valdecoxib or parecoxib; 5-lipoxygenase inhibitors; NSAIDs, such as diclofenac, indomethacin, nabumetone or ibuprofen; leukotriene receptor antagonists; DMARDs such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; monoaminergic uptake inhibitors such as venlafaxine; opioid analgesics; local anaesthetics; 5HT agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of Formula I or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

The weight ratio of the compound of the Formula I to the second active ingredient may be varied and will depend upon the effective dose of each ingredient. Generally, an effective dose of each will be used. Thus, for example, when a compound of Formula I is combined with an NSAID the weight ratio of the compound of Formula I to the NSAID will generally range from about 1000:1 to about 1:1000, preferably about 200:1 to about 1:200. Combinations of a compound of Formula I and other active ingredients will generally also be within the aforementioned range, but in each case, an effective dose of each active ingredient should be used.

ABBREVIATIONS USED IN THE DESCRIPTION OF THE PREPARATION OF THE COMPOUNDS OF THE PRESENT INVENTION aq aqueous
$Boc_2O$ di-t-butyl dicarbonate
$BF_3OEt_2$ Boron trifluoride etherate
brine saturated aqueous sodium chloride solution
$CH_2Cl_2$ or DCM dichloromethane
DMF N,N-Dimethylformamide
DIPA diisopropylamine
DIPEA N,N'-diisopropylethylamine
DMAP 4-N,N-dimethylaminopyridine
DMF N,N-dimethylformamide
DMSO dimethylsulfoxide
EtMgBr ethylmagnesiumbromide
$Et_3N$ triethylamine
EtOAc ethyl acetate
EtOH ethanol
$Et_2O$ or ether diethyl ether
g grams
h or hr hour
HCl hydrochloric acid
HCOOH Formic acid
$H_2NOSO_3H$ Hydroxylamine-o-sulfonic acid
HEPES 4-(2-hydroxyethyl)-1-piperazineethanesulfonic acid
HPLC High performance liquid chromatography
IPA 2-propanol i-PrOH isopropyl alcohol
i-Pr$_2$NH di-isopropyl amine
K$_2$CO$_3$ Potassium carbonate
K$_2$PO$_4$ Potassium phosphate
MeI methyliodide
mg milligrams
mL milliliters
mmol millimole
MeCN acetonitrile
MeOH methanol
MES 2-(N-morpholino)ethanesulfonic acid
min minutes
MS Mass Spectrum
nBuLi n-butyllithium
Na$_2$CO$_3$ sodium carbonate
NaH Sodium hydride
NaNO$_2$ Sodium nitrate
NaOAc sodium acetate
Na$_2$SO$_4$ sodium sulfate
Pd(dppf)Cl$_2$ (1,1'-Bis(diphenylphosphino)ferrocene)palladium(II)dichloride
Pd(OAc)$_2$ palladium(II)acetate
PivCl pivaloyl chloride
PyBOP (benzotriazol-1-yloxy)tripyrrolidinophosphonium hexafluorophosphate
R$_f$ retention time
rt room temperature
TFA trifluoroacetic acid
Tf$_2$O trifluoromethanesulfonic(triflic)anhydride
THF tetrahydrofuran
Ti(O$^i$Pr)$_4$ titanium (IV) isopropoxide
μL microliters

SYNTHESIS

The compounds of this invention may be prepared by employing reactions as shown in the following schemes 1 through 5, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The preferred methods for synthesizing the non-commercially available starting materials used in the synthesis of compounds of Formula I are presented below.

Scheme 1

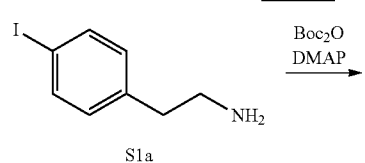

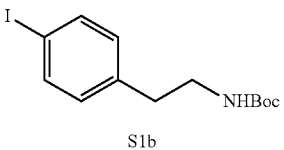

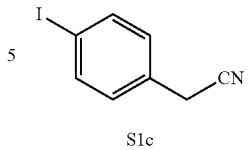

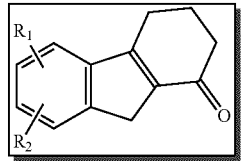

Scheme 1 represents the synthesis of representative 1-(4-iodobenzyl) components prepared by methods known in the art of organic synthesis using commercially available reagents.

Scheme 2

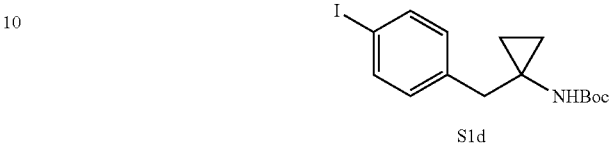

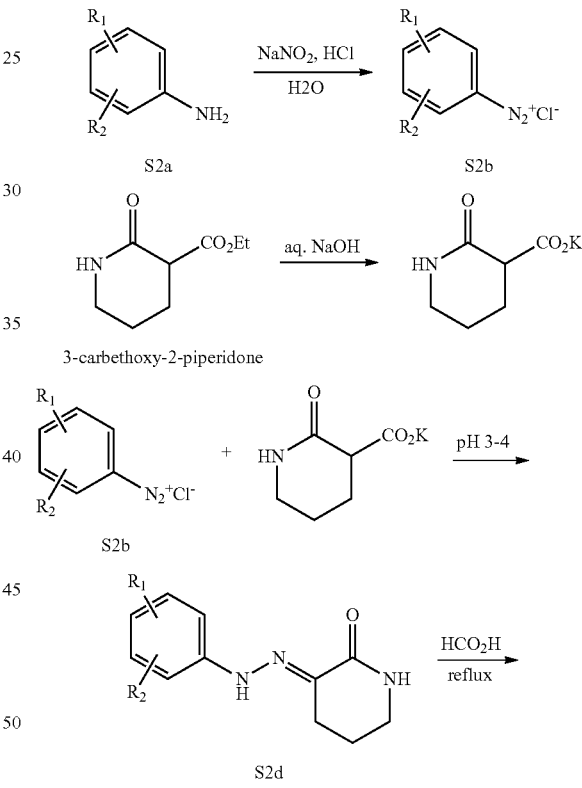

Scheme 2 represents the synthesis of a generic β-carboline component. Commercially available anilines (S2a) were converted to the diazonium salts (S2b) using well established chemistry (e.g. Vorlaender; Meyer, F. *Justus Liebegs Ann. Chem.* 1902, 320, 138) and these were converted to carbolines (S2e) using Fisher-indole chemistry (Abramovitch, R. A.; Bulman, A. *Synlett* 1992, 10, 795).

Scheme 3

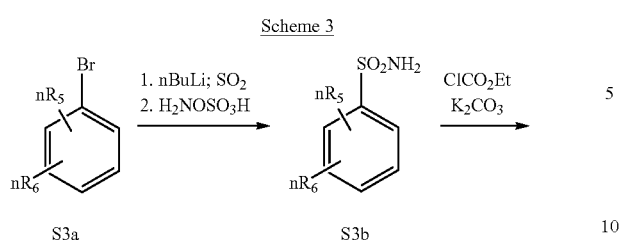 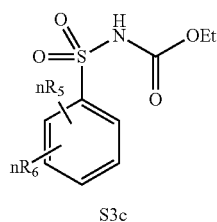

Scheme 3 represents the synthesis of a genetic sulphonylurea component. Sulfonamides (S3b) were either commercially available, or prepared from the respective aryl bromides (S3a) using lithiation/sulfonation chemistry (Graham, S. L.; Scholtz, T. H. *Synthesis* 1986, 1031). Conversion to the desired sulfonylcarbamates (S3c) was straightforward.

Scheme 4

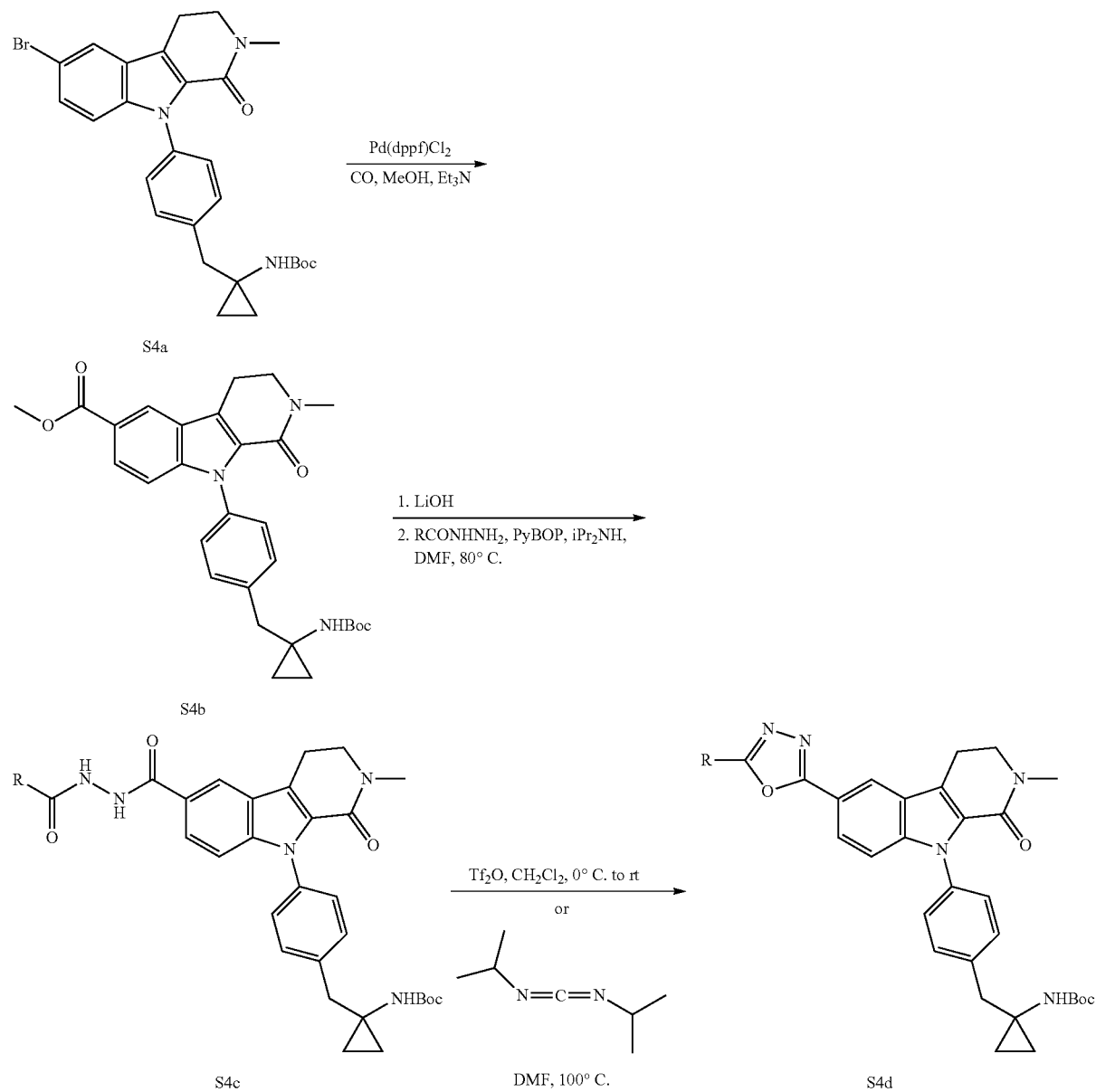

Scheme 4 represents the functionalization of bromocarboline. Palladium-catalyzed carbonylation, followed by hydrolysis and straightforward amide coupling provided the hydrazides (S4c). Cyclization to the desired oxadiazoles (S4d) was mediated by either triflic anhydride (Liras, S.; Allen, M. P.; Segelstein, B. E. *Syn. Comm.* 2000, 30, 437) or diisopropyl carbodiimide.

Scheme 5

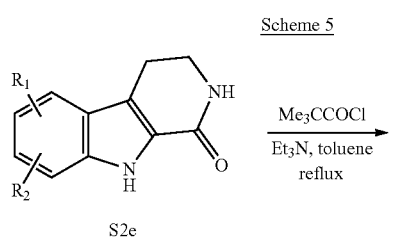

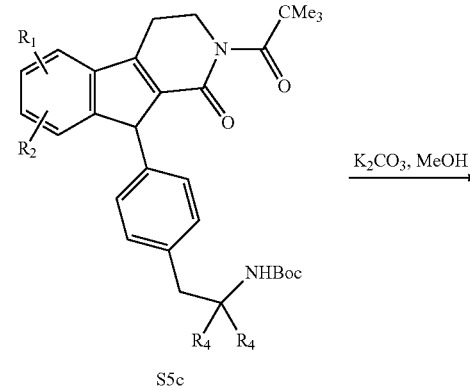

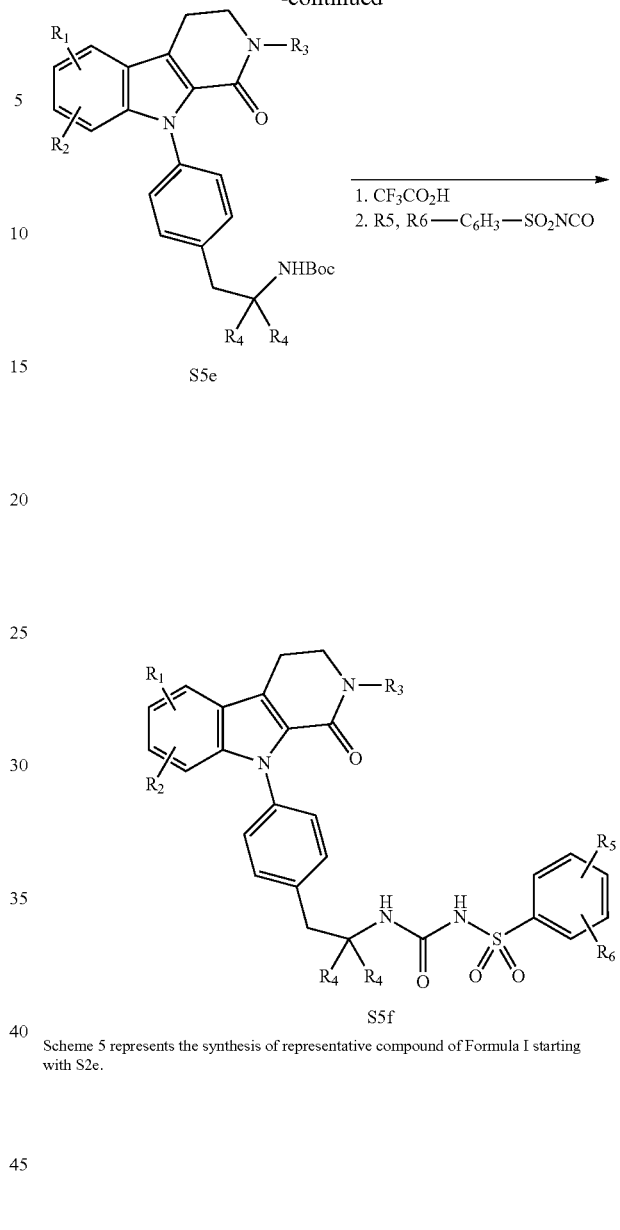

Scheme 5 represents the synthesis of representative compound of Formula I starting with S2e.

Protection of the lactam NH of the carbolines (S2e) was necessary prior to N-arylation of the indole, and this was accomplished by forming the pivaloyl succinamides (S5a). Ullman-type conditions were employed to effect the desired arylation (Antilla, J. L.; Klapars, A.; Buchwald, S. L. *J. Am. Chem. Soc.* 2002, 124, 11684), providing the N-aryl carbolines (S5c). The iodides (S5b) were either commercially available ($R_4$, $R_4$=H) or available from the nitrile via a Kulinkovich cyclization (Bertus, P.; Szymoniak, *J. Chem. Commun.* 2001, 1792) of the requisite nitrile ($R_4$—$R_4$=$CH_2C_2$). Pevely removal and calculation provided the N-alkyl Carolinas (S5e), which were converted to the final sulfonylurea's (S5f) by Boc-deprotection and treatment either with commercially available isocyanates or previously prepared sulfonylcarbamates (S3c).

EXAMPLE 1

4-chloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide (1-1)

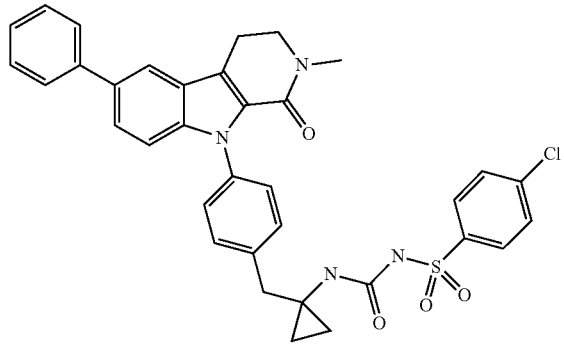 [SMILES: CN1CCc2c(n(-c3ccc(CC4(NC(=O)NS(=O)(=O)c5ccc(Cl)cc5)CC4)cc3)c3ccc(-c4ccccc4)cc23)C1=O]

Step 1(a)-(c): RE 1a, RE 1b, and RE 1c

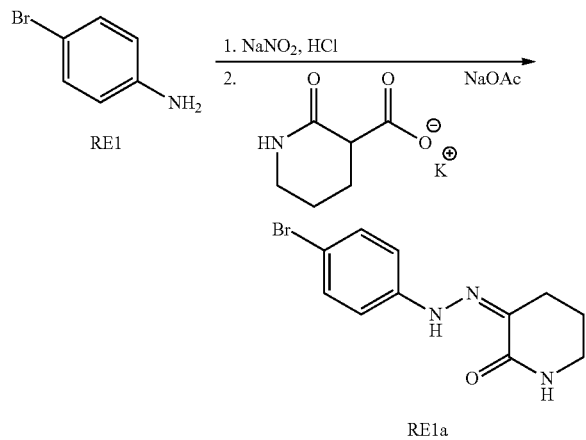

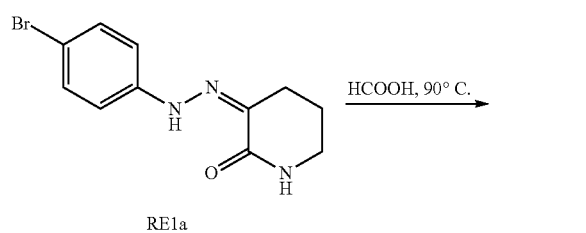

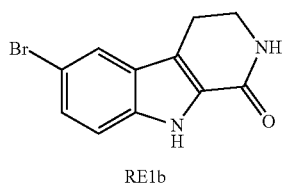

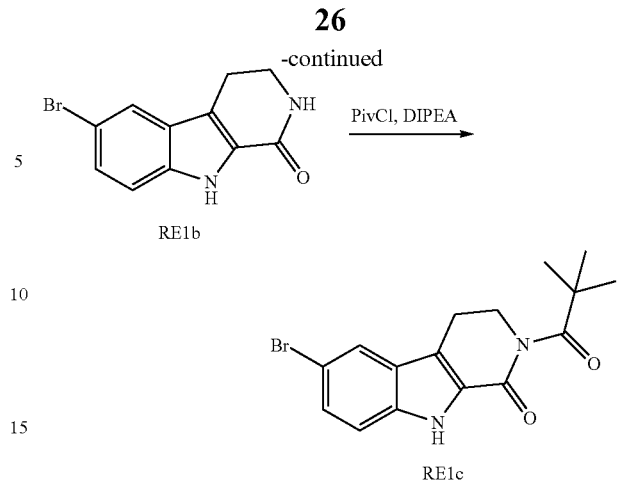

Step 1(a)

To a solution of 3-carbethoxy-2-piperidone (49.7 g, 290 mmol) in H$_2$O (500 mL) was added solid KOH (17.1 g, 305 mmol) and the mixture was stirred overnight at rt ("carboxylate solution"). In a separate reaction flask, approximately 200 g of ice was added to a suspension of the aniline (50.0 g, 290 mmol) in 100 mL conc. HCl(aq), and the mixture was cooled to 0° C. To this mixture was added a solution of NaNO$_2$ (22.0 g, 319 mmol) in H$_2$O (100 mL) via dropping funnel over approximately 1 hour. The mixture became homogeneous, and was stirred for an additional hour at 0° C. ("diazonium solution"). To the carboxylate solution was added approximately 200 g ice, and this solution was chilled to 0° C. The diazonium solution was then transferred to an addition funnel, approximately 200 g of ice was added, and this solution was added to the carboxylate over approximately 1.5 hours. When the addition was complete, the pH of the mixture was adjusted to approximately 4 using approximately 150 mL of sat. NaOAc(aq), and the resulting mixture was stirred for 3 hours at 0° C. The fine precipitate which was formed was removed by filtration through a medium porosity fritted funnel, and rinsed with 3×200 mL H$_2$O and 2×200 mL Et$_2$O, then air dried overnight to provide 44 g of approximately 90% purity diazolactam (RE1a) as a light yellow solid which was used directly without further purification.

Step 1(b)

A solution of the diazolactam (44.0 g, approximately 90% purity) in formic acid (250 mL) was heated to 90° C. for 90 minutes, at which point a solid had formed. The mixture was cooled to rt, then diluted with 500 mL H$_2$O. The resulting light brown solid was removed by filtration, then washed with 100 mL H$_2$O, 100 mL 2 M Na$_2$CO$_3$(aq), 2×100 mL H$_2$O then 100 mL cold Et$_2$O. The resulting solid was air dried then pumped under high vacuum to provide 37.6 g (142 mmol, 49% (2 steps)) of indole as a light yellow solid.

Step 1(c)

To a solution of the lactam (19.0 g, 71.7 mmol) in toluene (150 mL) was added Hunig's base (25.0 mL, 143 mmol) then pivaloyl chloride (9.70 mL, 78.9 mmol). The mixture was heated to 110° C. for 2 hours, then cooled to rt. An additional 2.0 mL (16.3 mmol) of pivaloyl chloride was added, and heating continued for an additional 2 hours. After cooling to rt, the red solution was poured into H$_2$O (250 mL) and the product extracted with ethyl acetate (3×200 mL). The combined organic fractions were washed with brine (200 mL), dried (Na$_2$SO$_4$) and concentrated in vacuo. Purification by flash column chromatography (80:20 hexanes:EtOAc) provided 11.2 g (32.0 mmol, 45%) of the desired protected lactam as a yellow powder (RE1c).

Step 2 (a) and (b): RE 2a and RE 2b

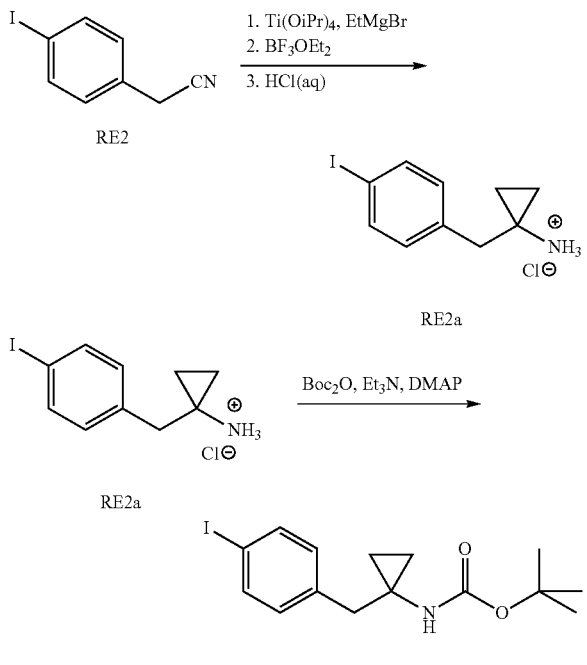

Step 2(a)

A solution of the nitrile (50.0 g, 206 mmol) in toluene (500 mL) was cooled to −25° C., then Ti(O$^i$Pr)$_4$ (60.3 mL, 206 mmol) was added. A commercial (Aldrich) solution of EtMgBr (3.0 M, 137 mL, 411 mmol) was then added dropwise at a rate which maintained the internal temperature between −20 and −25° C. (over approximately 60 minutes). The mixture was stirred for 60 minutes at this temperature, then the BF$_3$OEt$_2$ (52.1 mL, 411 mmol) was added dropwise maintaining a constant internal temperature (over approximately 30 minutes). After stirring the resulting solution for 60 minutes, the mixture was poured into 750 mL 3 N HCl(aq) and stirred rapidly for 30 minutes while warming to room temperature. The mixture was then transferred to a separatory funnel, and allowed to settle for 30 minutes. The thick yellow oil which separated on the bottom was carefully removed, then dissolved in CH$_2$Cl$_2$ (1 L), dried (Na$_2$SO$_4$) and concentrated in vacuo to provide 24 g of the amine salt (RE2a) of sufficient purity (approximately 80%) to be used directly.

Step 2(b)

To a solution of the amine salt (24 g, approximately 80% purity, approximately 78 mmol) in MeOH was added Et$_3$N (27.2 mL, 195 mmol) and Boc$_2$O (17.1 g, 78 mmol) and DMAP. The mixture was stirred for 24 hours at rt. NMR analysis of an aliquot indicated only approximately 60% conversion, so an extra equivalent of Boc$_2$O (17.1 g) and Et$_3$N (10.9 mL) were added, and stirring continued for an additional 24 hours. NMR analysis at this stage showed approximately 80% conversion, so another equivalent of Boc$_2$O (17.1 g) and Et$_3$N (10.9 mL) were added and the mixture was stirred for an additional 24 hours. MeOH was then removed in vacuo, then the residue was diluted with Et$_2$O (400 mL) and washed with H$_2$O (400 mL) and brine (400 mL). The aqueous fractions were further extracted with Et$_2$O (400 mL), then the combined organic extracts were dried (Na$_2$SO$_4$; CH$_2$Cl$_2$ added) and concentrated in vacuo. Purification by flash column chromatography (dry load; 100:0 to 80:20 hexanes:EtOAc, linear gradient) provided 12.0 g (30.5 mmol, 15% (2 steps)) of N-Boc cyclopropyl amine (RE2b) as a yellow solid of approximately 95% purity.

Step 3: RE 3

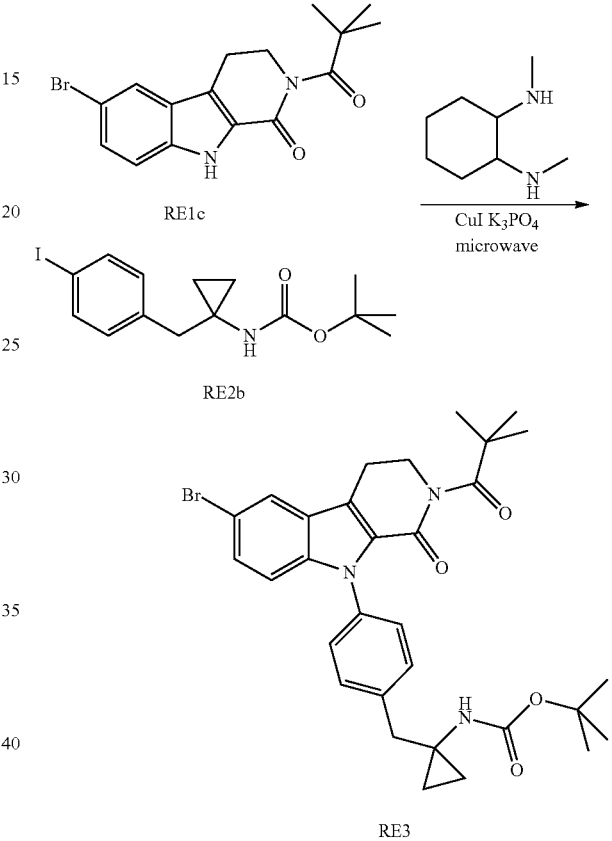

To a mixture of the iodide (1.00 g, 2.68 mmol), carboline (0.982 g, 2.81 mmol), CuI (0.102 g, 0.536 mol) and K$_3$PO$_4$ (1.14 g, 5.36 mmol) in a microwave vial was added toluene that had been degassed by bubbling N$_2$ through for approximately 15 minutes. The ligand (rac-trans-N,N'-dimethylcyclohexane-1,2-diamine, 0.169 mL, 1.07 mmol) was then added, and the mixture was capped and placed in the microwave generator for 30 minutes at 110° C. The mixture was then diluted with H$_2$O (100 mL) and extracted with CH$_2$Cl$_2$ (2×100 mL). The combined organic extracts were dried (Na$_2$SO$_4$) and concentrated in vacuo. Purification by flash column chromatography (load w/CH$_2$Cl$_2$; 100:0 to 60:40 hexanes:EtOAc, linear gradient) provided 468 mg of N-aryl carboline as a approximately 5:1 mixture of bromide:iodide at the 5-position of the carboline. The bromide:iodide ratio obtained is variable, but the mixture can be used directly in downstream coupling processes.

Step 4(a) and (b): RE 4b and RE 4c

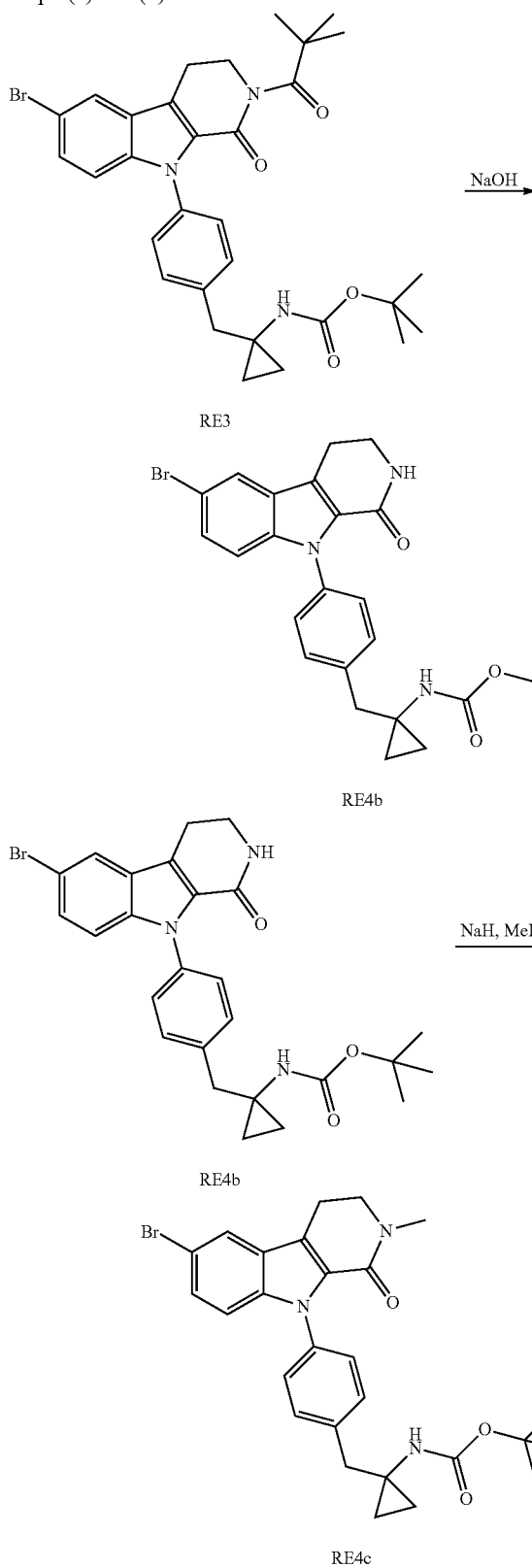

stirred for 45 minutes at rt, at which point TLC analysis showed complete conversion. The mixture was diluted with EtOAc (100 mL) and H$_2$O (100 mL) and brine (25 mL). After separation, the organic phase was then washed with additional brine (100 mL), then the aqueous fractions were further extracted with EtOAc (100 mL). The combined organic extracts were dried (Na$_2$SO$_4$) and concentrated in vacuo to provide 394 mg of free lactam as a 5:1 mixture of bromide:iodide.

Step 4(b)

To a solution of the lactam (5:1 mixture of bromide:iodide; 394 mg) in THF (8.0 mL) was added NaH (60 wt %, 34.0 mg, 0.849 mmol) and the mixture was stirred for 30 minutes at rt. MeI was then added, and the mixture was stirred overnight then quenched by pouring into sat. NH$_4$Cl(aq) (100 mL). The product was extracted with CH$_2$Cl$_2$ (2×100 mL), and the combined organic extracts were dried (Na$_2$SO$_4$) and concentrated in vacuo. Purification by flash column chromatography (load w/CH$_2$Cl$_2$; 50:50 to 0:100 hexanes:EtOAc, linear gradient) provided 234 mg of N-methyl lactam (5:1 mixture of bromide:iodide) as well as 75 mg of recovered starting material.

Step 5: RE 5-1

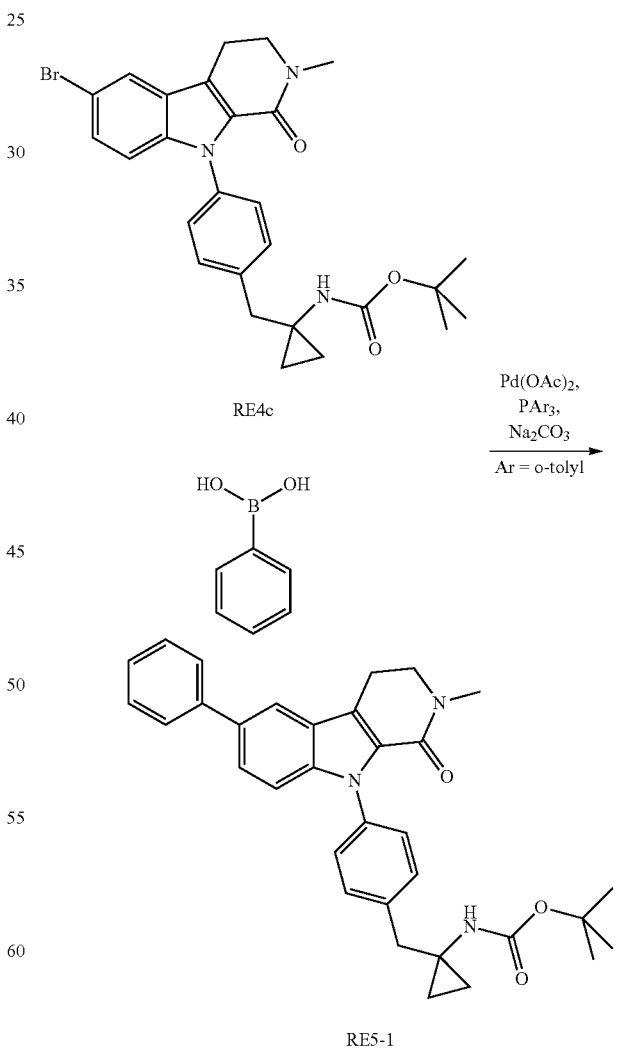

Step 4(a)

To a solution of the N-Piv carboline (5:1 mixture of bromide:iodide; 468 mg) in 1:1 MeOH/THF (8 mL) was added NaOH(aq) (2 M, 1.57 mL, 3.15 mmol) and the mixture was A suspension of the aryl bromide (280 mg, 0.534 mmol), boronic acid (98 mg, 0.801 mmol), Na$_2$CO$_3$ (113 mg, 1.07 mmol), the phosphine (32.5 mg, 0.107 mmol) and Pd catalyst (12.0 mg, 0.053 mmol) in 6:1 toluene/water (3.5 mL) was heated to 110° C. for 2 hours, at which point Pd black had crashed out of solution. The mixture was cooled to rt then filtered through a plug of SiO$_2$ and NaHCO$_3$ with EtOAc as eluent. After concentration in vacuo, NMR analysis showed complete conversion to the desired product. Purification by flash column chromatography (load w/CH$_2$Cl$_2$; 50:50 to 10:90 hexanes:EtOAc, linear gradient) provided 279 mg (0.533 mmol, quant) of pure phenyl carboline as an off-white solid (RE5-1).

Step 6(a) and (b): RE 6b and RE 6c

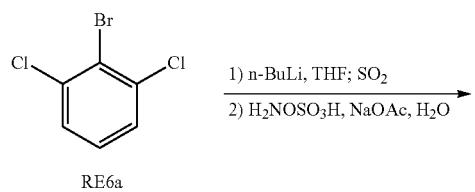

RE6a

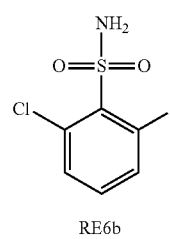

RE6b

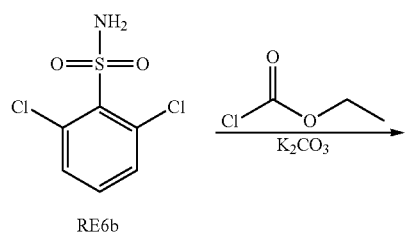

RE6b

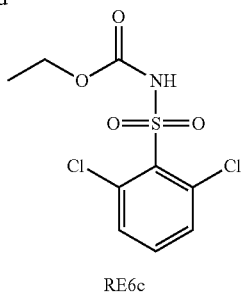

RE6c

Step 6(a)

To a solution of 1-bromo-2,6-dichlorobenzene (4.34 g, 19.2 mmol) in THF (20 mL) at −78° C. was added n-BuLi (1.6 M in hexanes, 10.0 mL, 16.0 mmol). The reaction mixture (precipitate formed with time) was stirred at −78° C. for 4 hours. Sulfur dioxide was then bubbled into the mixture for 15 min. The yellow solution was warmed to RT, during which time a colorless precipitate formed. After 30 min at RT, hexane was added and the sulfinic salt was removed by filtration. The salt was dissolved in water (50 mL) and sodium acetate (3.28 g, 40.0 mmol) was added. The solution was cooled to 10° C. and hydroxylamine-O-sulfonic acid (2.26 g, 20.0 mmol) was added. The ice-water bath was removed, and a white product precipitated out within minutes. The reaction was stirred at RT overnight. The reaction was extracted with EtOAc (3×50 mL), and the combined organic layers were washed with 5% NaHCO$_3$(aq) (50 mL) and brine (50 mL), then dried (Na$_2$SO$_4$) and concentrated in vacuo to provide 2.66 g (11.8 mmol, 74%) of the sulfonamide (RE6b) as a white solid.

Step 6(b)

To a heterogeneous mixture of sulfonamide (14.5 g, 64.1 mmol) and potassium carbonate (31.0 g, 224 mmol) in acetone (130 mL) was added ethyl chloroformate (15.4 mL, 160 mmol). The reaction was heated to reflux overnight, then cooled to rt, and quenched by the addition of 200 mL 1 N HCl (aq). The product was extracted with EtOAc (3×200 mL), and the combined organic extracts were dried (Na$_2$SO$_4$) and concentrated in vacuo to provide 18.8 g (63.1 mmol, 98%) of pure sulfonyl carbamate (RE6c) as a white solid.

Step 7(a) and (b): RE 7 and RE 7a

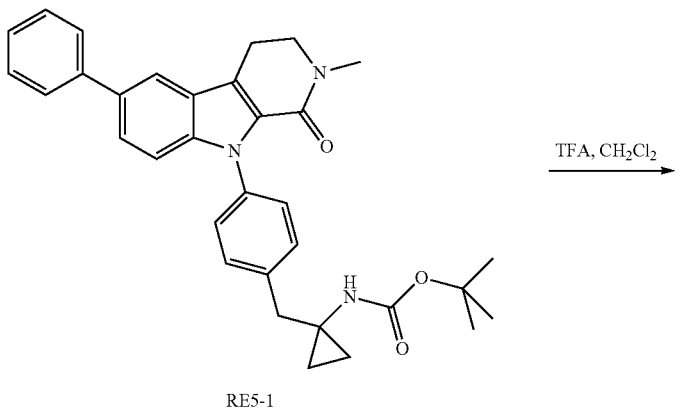

RE5-1

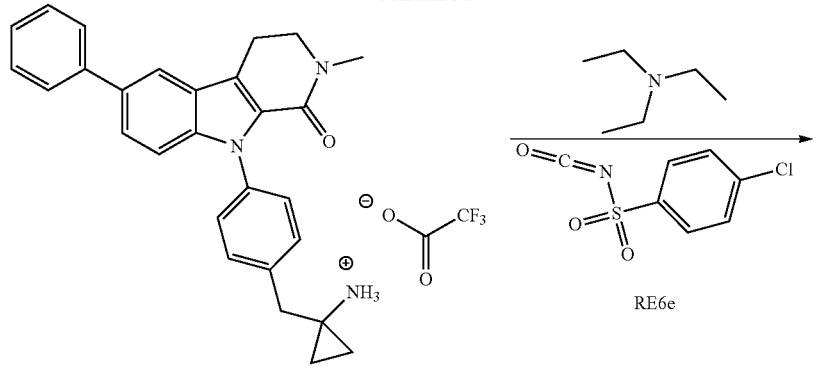

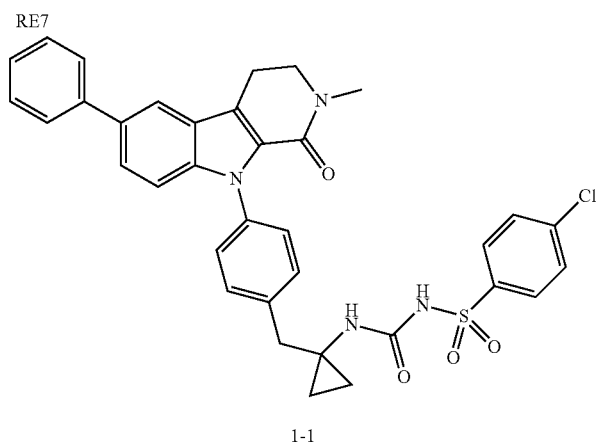

Step 7(a)

To a solution of the carbamate (RE5-1) (280 mg, 0.537 mmol) in $CH_2Cl_2$ (2.0 mL) was added TFA (2.0 mL) and the mixture was stirred at rt for 30 minutes at which point TLC analysis indicated complete conversion. The mixture was concentrated in vacuo then pumped under high vacuum for 30 minutes to provide 287 mg (0.537 mmol, quant) of ammonium salt which was used directly without purification. If the free base is desired, the ammonium salt can be shaken vigorously in a biphasic mixture of $CH_2Cl_2$ and sat. $NaHCO_3$(aq). After separation, the organic layer can be dried ($Na_2SO_4$), then in vacuo concentration provides the free base.

Step 7(b)

To a solution of the amine salt (RE7) (287 mg, 0.537 mmol) in $CH_2Cl_2$ (5.0 mL) was added $Et_3N$ (0.150 mL, 1.07 mmol) and the mixture was stirred for 30 minutes. The isocyanate (0.080 mL, 0.537 mmol) was then added and the mixture was stirred for 3 hours at rt at which point TLC analysis indicated complete conversion. The mixture was concentrated in vacuo, then purified directly by flash column chromatography (load w/$CH_2Cl_2$; 50:50 to 0:100 hexanes:(99:1 EtOAc:AcOH), linear gradient) to provide 253 mg (0.396 mmol, 74%) of pure sulfonylurea as a light yellow solid (1-1) (MS (M+H) 639.1).

Compounds (Examples 1-2 through 1-37) were prepared in a similar manner as the compound, Example 1-1, but using the appropriate lactam to generate the desired product.

TABLE 1

| Ex | IUPAC name | Structure | MS |
|---|---|---|---|
| 1-1 | 4-chloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | 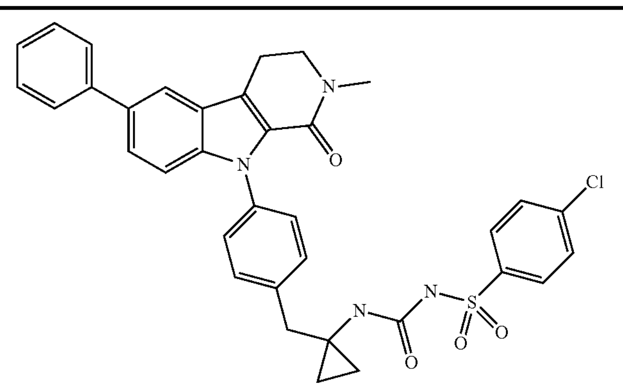 | 639.1 (M + H) |

TABLE 1-continued

| Ex | IUPAC name | Structure | MS |
|---|---|---|---|
| 1-2 | 4-methyl-N-[({2-[4-(2,5,7-trimethyl-1-oxo-1,2,3,4-tetrahydro-9H-beta-carbolin-9-yl)phenyl]ethyl}amino)carbonyl]benzenesulfonamide | 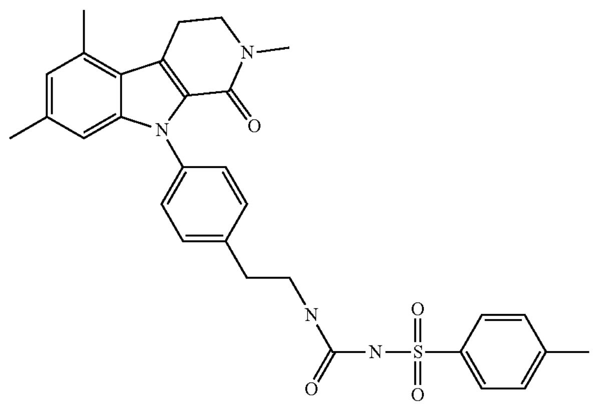 | |
| 1-3 | 4-chloro-N-[({2-[4-(5,7-dichloro-2-methyl-1-oxo-1,2,3,4-tetrahydro-9H-beta-carbolin-9-yl)phenyl]ethyl}amino)carbonyl]benzenesulfonamide | 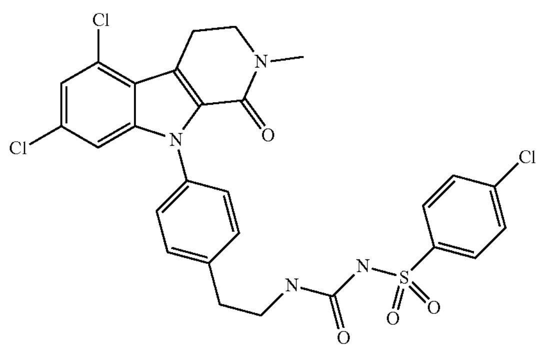 [SMILES: CN1CCc2c(n(-c3ccc(CCNC(=O)NS(=O)(=O)c4ccc(Cl)cc4)cc3)c3cc(Cl)cc(Cl)c23)C1=O] | 606.5 (M + H) |
| 1-4 | 4-chloro-N-[({2-[4-(6-chloro-2-methyl-1-oxo-1,2,3,4-tetrahydro-9H-beta-carbolin-9-yl)phenyl]ethyl}amino)carbonyl]benzenesulfonamide | 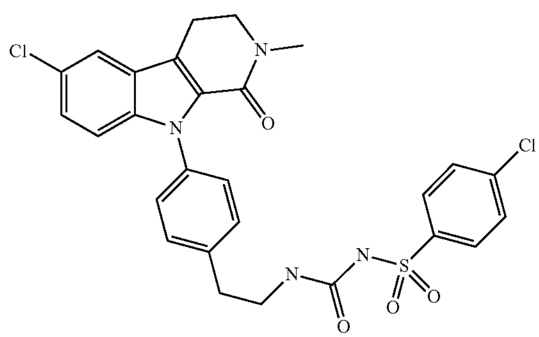 | 571.9 (M + H) |
| 1-5 | N-[({2-[4-(6-bromo-2-methyl-1-oxo-1,2,3,4-tetrahydro-9H-beta-carbolin-9-yl)phenyl]ethyl}amino)carbonyl]-4-chlorobenzenesulfonamide | 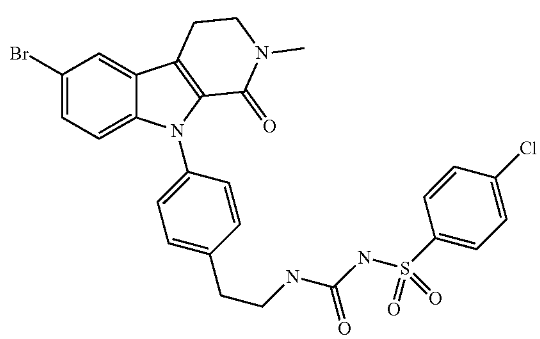 | 616.4 (M + H) |

TABLE 1-continued

| Ex | IUPAC name | Structure | MS |
|---|---|---|---|
| 1-6 | 4-chloro-N-[({2-[4-(5,7-dichloro-2-ethyl-1-oxo-1,2,3,4-tetrahydro-9H-beta-carbolin-9-yl)phenyl]ethyl}amino)carbonyl]benzenesulfonamide | 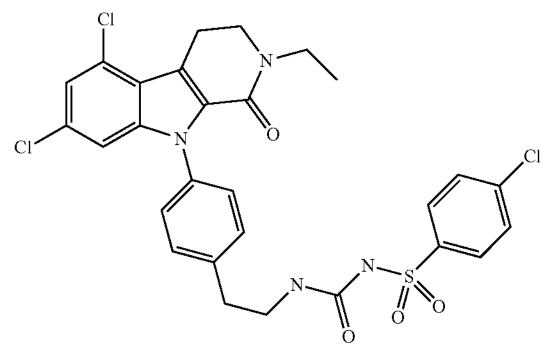 [SMILES: CCN1CCc2c(n(-c3ccc(CCNC(=O)NS(=O)(=O)c4ccc(Cl)cc4)cc3)c3cc(Cl)cc(Cl)c23)C1=O] | 620.5 (M + H) |
| 1-7 | 4-chloro-N-{[(2-{4-[5,7-dichloro-2-(cyclopropylmethyl)-1-oxo-1,2,3,4-tetrahydro-9H-beta-carbolin-9-yl]phenyl}ethyl)amino]carbonyl}benzenesulfonamide | 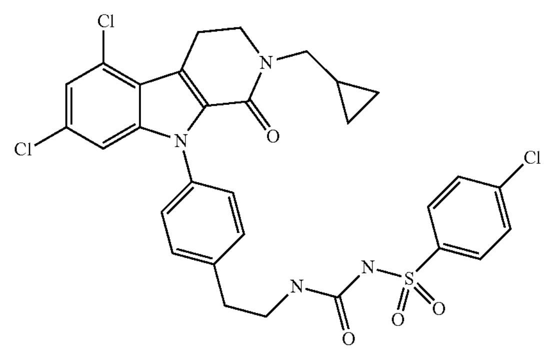 [SMILES: O=C(NCCc1ccc(-n2c3c(c4c(Cl)cc(Cl)cc42)CCN(CC2CC2)C3=O)cc1)NS(=O)(=O)c1ccc(Cl)cc1] | 646.5 (M + H) |
| 1-8 | 4-chloro-N-[({2-[4-(2-methyl-1-oxo-6-phenyl-1,2,3,4-tetrahydro-9H-beta-carbolin-9-yl)phenyl]ethyl}amino)carbonyl]benzenesulfonamide | 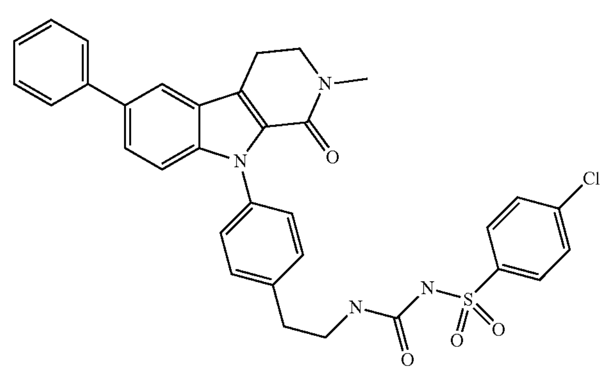 | 613.6 (M + H) |
| 1-9 | 4-chloro-N-[({2-[4-(5,7-dichloro-1-oxo-2-phenyl-1,2,3,4-tetrahydro-9H-beta-carbolin-9-yl)phenyl]ethyl}amino)carbonyl]benzenesulfonamide | 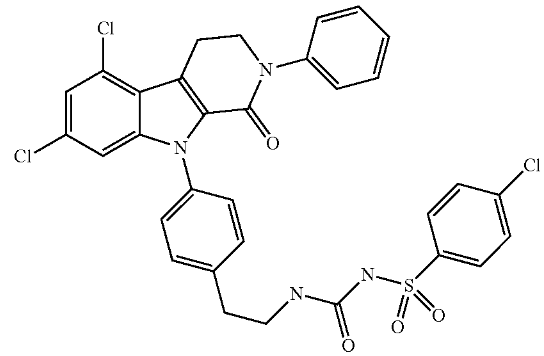 [SMILES: O=C(NCCc1ccc(-n2c3c(c4c(Cl)cc(Cl)cc42)CCN(c2ccccc2)C3=O)cc1)NS(=O)(=O)c1ccc(Cl)cc1] | 668.5 (M + H) |

TABLE 1-continued

| Ex | IUPAC name | Structure | MS |
|---|---|---|---|
| 1-10 | 4-chloro-N-[({2-[4-(6,7-dichloro-2-methyl-1-oxo-1,2,3,4-tetrahydro-9H-beta-carbolin-9-yl)phenyl]ethyl}amino)carbonyl]benzenesulfonamide | 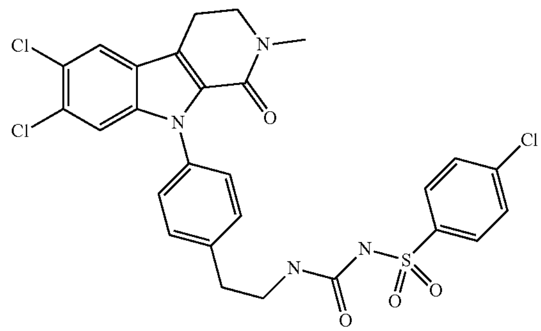 [SMILES: CN1CCc2c(n(-c3ccc(CCNC(=O)NS(=O)(=O)c4ccc(Cl)cc4)cc3)c3cc(Cl)c(Cl)cc23)C1=O] | 606.4 (M + H) |
| 1-11 | 4-chloro-N-[({2-[4-(5,6-dichloro-2-methyl-1-oxo-1,2,3,4-tetrahydro-9H-beta-carbolin-9-yl)phenyl]ethyl}amino)carbonyl]benzenesulfonamide | 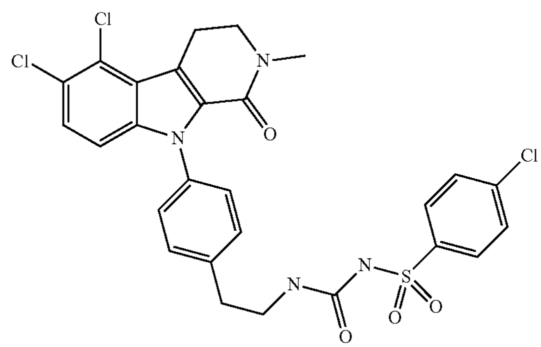 [SMILES: CN1CCc2c(n(-c3ccc(CCNC(=O)NS(=O)(=O)c4ccc(Cl)cc4)cc3)c3ccc(Cl)c(Cl)c23)C1=O] | 606.4 (M + H) |
| 1-12 | 4-chloro-N-[({2-[4-(7-chloro-2-methyl-1-oxo-1,2,3,4-tetrahydro-9H-beta-carbolin-9-yl)phenyl]ethyl}amino)carbonyl]benzenesulfonamide | 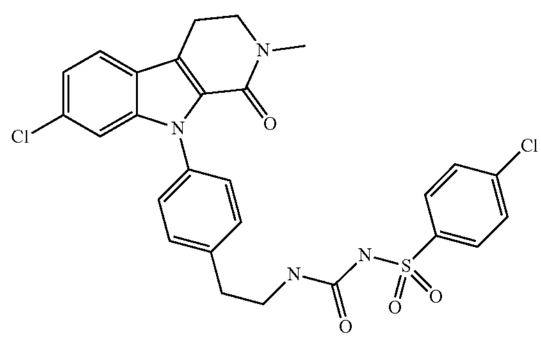 [SMILES: CN1CCc2c(n(-c3ccc(CCNC(=O)NS(=O)(=O)c4ccc(Cl)cc4)cc3)c3cc(Cl)ccc23)C1=O] | 571.9 (M + H) |
| 1-13 | 4-chloro-N-[({2-[4-(5-chloro-2-methyl-1-oxo-1,2,3,4-tetrahydro-9H-beta-carbolin-9-yl)phenyl]ethyl}amino)carbonyl]benzenesulfonamide | 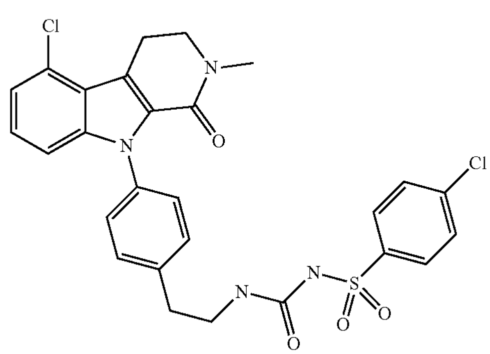 [SMILES: CN1CCc2c(n(-c3ccc(CCNC(=O)NS(=O)(=O)c4ccc(Cl)cc4)cc3)c3cccc(Cl)c23)C1=O] | 571.9 (M + H) |

TABLE 1-continued

| Ex | IUPAC name | Structure | MS |
|---|---|---|---|
| 1-14 | N-[({2-[4-(5-bromo-2-methyl-1-oxo-1,2,3,4-tetrahydro-9H-beta-carbolin-9-yl)phenyl]ethyl}amino)carbonyl]-4-chlorobenzenesulfonamide | 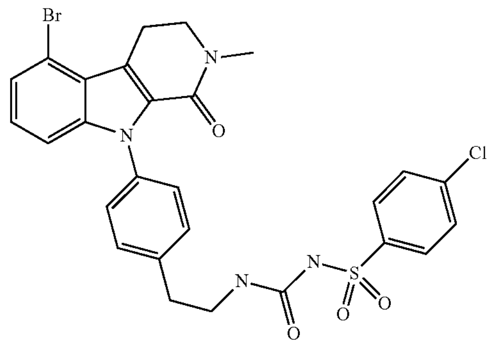 [SMILES: CN1CCc2c(n(-c3ccc(CCNC(=O)NS(=O)(=O)c4ccc(Cl)cc4)cc3)c3cccc(Br)c23)C1=O] | 616.4 (M + H) |
| 1-15 | N-[({2-[4-(7-bromo-2-methyl-1-oxo-1,2,3,4-tetrahydro-9H-beta-carbolin-9-yl)phenyl]ethyl}amino)carbonyl]-4-chlorobenzenesulfonamide | 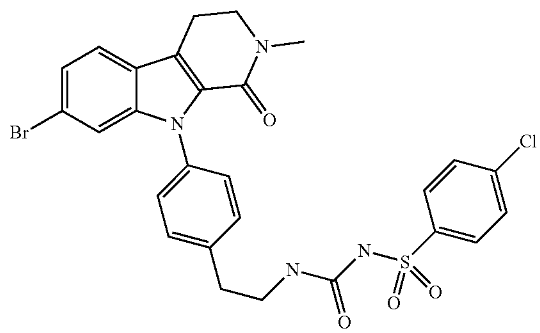 | 616.4 (M + H) |
| 1-16 | N-[({1-[4-(6-bromo-2-methyl-1-oxo-1,2,3,4-tetrahydro-9H-beta-carbolin-9-yl)benzyl]cyclopropyl}amino)carbonyl]-4-chloro-benzenesulfonamide | 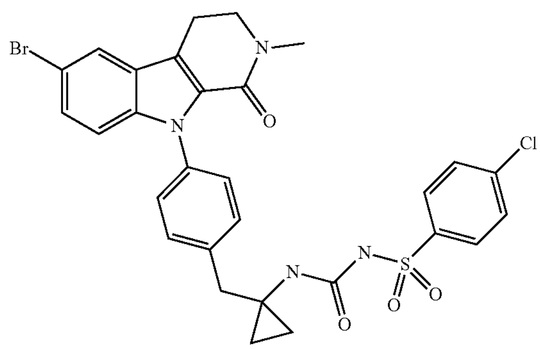 | 614.2 (M + H) |
| 1-17 | 4-chloro-N-[({2-[4-(2-methyl-1-oxo-5-phenyl-1,2,3,4-tetrahydro-9H-beta-carbolin-9-yl)phenyl]ethyl}amino)carbonyl]benzenesulfonamide | 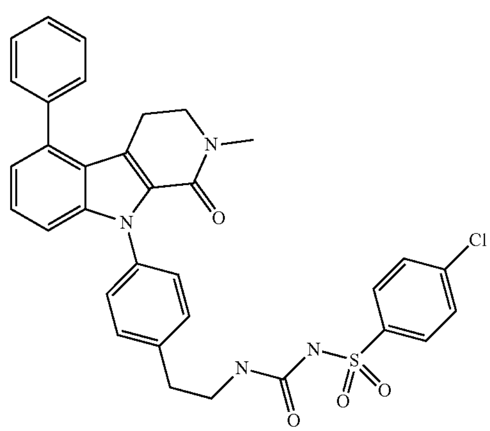 [SMILES: CN1CCc2c(n(-c3ccc(CCNC(=O)NS(=O)(=O)c4ccc(Cl)cc4)cc3)c3cccc(-c4ccccc4)c23)C1=O] | 614.3 (M + H) |

TABLE 1-continued

| Ex | IUPAC name | Structure | MS |
|---|---|---|---|
| 1-18 | 4-chloro-N-[({2-[4-(2-methyl-1-oxo-7-phenyl-1,2,3,4-tetrahydro-9H-beta-carbolin-9-yl)phenyl]ethyl}amino)carbonyl]benzenesulfonamide | 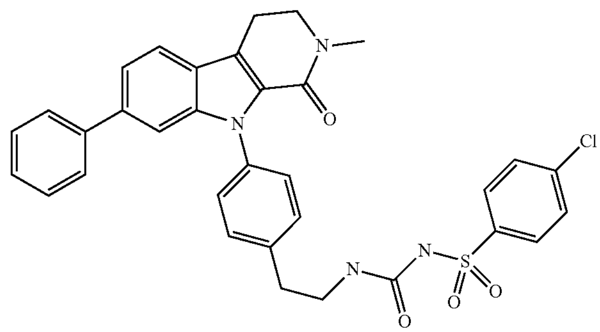 | 577.1 (M + H) |
| 1-19 | 4-chloro-N-{[(2-{4-[6-(4-fluorophenyl)-2-methyl-1-oxo-1,2,3,4-tetrahydro-9H-beta-carbolin-9-yl]phenyl}ethyl)amino]carbonyl}benzenesulfonamide | 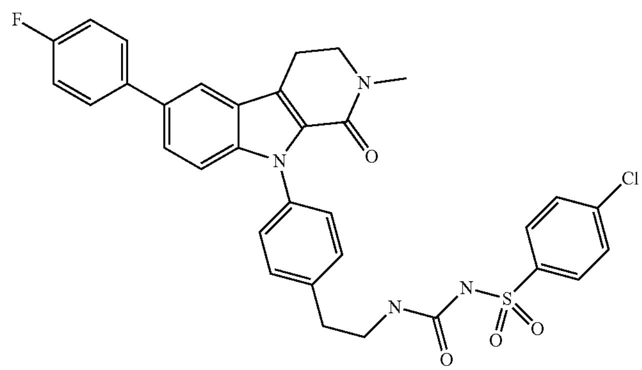 [SMILES: CN1CCc2c(n(-c3ccc(CCNC(=O)NS(=O)(=O)c4ccc(Cl)cc4)cc3)c3ccc(-c4ccc(F)cc4)cc23)C1=O] | 593.0 (M + Na) |
| 1-20 | 4-chloro-N-[({2-[4-(8-chloro-2-methyl-1-oxo-1,2,3,4-tetrahydro-9H-beta-carbolin-9-yl)phenyl]ethyl}amino)carbonyl]benzenesulfonamide | 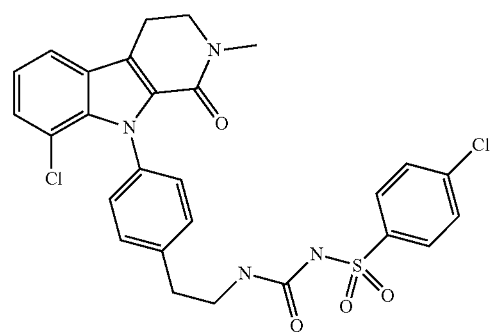 | 691.1 (M + H) |
| 1-21 | 4-chloro-N-[({2-[4-(2-methyl-1-oxo-6-pyridin-3-yl-1,2,3,4-tetrahydro-9H-beta-carbolin-9-yl)phenyl]ethyl}amino)carbonyl]benzenesulfonamide | 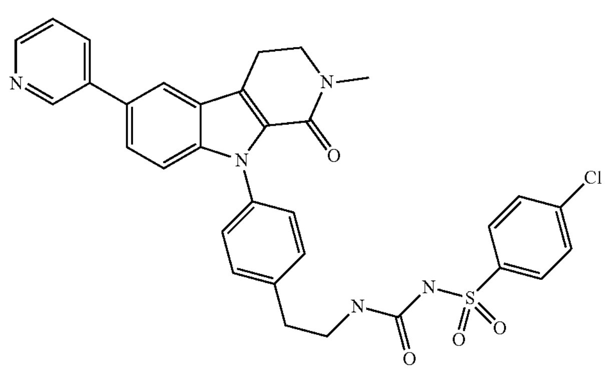 | 692.0 (M + H) |

TABLE 1-continued

| Ex | IUPAC name | Structure | MS |
|---|---|---|---|
| 1-22 | 4-chloro-N-[({2-[4-(2-methyl-1-oxo-6-pyridin-2-yl-1,2,3,4-tetrahydro-9H-beta-carbolin-9-yl)phenyl]ethyl}amino)carbonyl]benzene-sulfonamide | 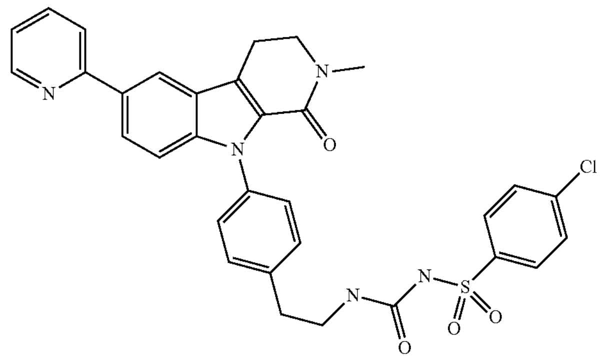 | 577.1 (M + H) |
| 1-23 | 4-chloro-N-{[(1-{4-[6-(2-fluorophenyl)-2-methyl-1-oxo-1,2,3,4-tetrahydro-9H-beta-carbolin-9-yl]benzyl}cyclopropyl)amino]carbonyl}benzene-sulfonamide | 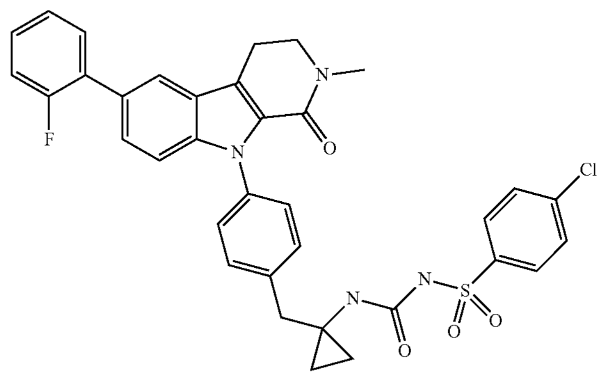 [SMILES: CN1CCc2c(n(-c3ccc(CC4(NC(=O)NS(=O)(=O)c5ccc(Cl)cc5)CC4)cc3)c3ccc(-c4ccccc4F)cc23)C1=O] | 657.1 (M + H) |
| 1-24 | 4-chloro-N-[({1-[4-(2-methyl-1-oxo-6-pyridin-3-yl-1,2,3,4-tetrahydro-9H-beta-carbolin-9-yl)benzyl]cyclopropyl}amino)carbonyl]benzene-sulfonamide | 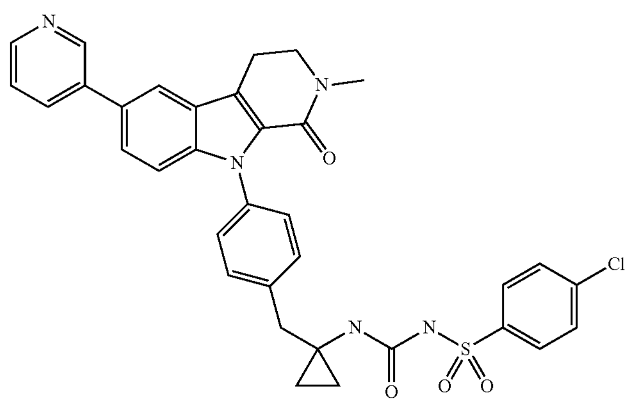 [SMILES: CN1CCc2c(n(-c3ccc(CC4(NC(=O)NS(=O)(=O)c5ccc(Cl)cc5)CC4)cc3)c3ccc(-c4cccnc4)cc23)C1=O] | 640.2 (M + H) |
| 1-25 | 4-chloro-N-{[(1-{4-[2-methyl-1-oxo-6-(3-thienyl)-1,2,3,4-tetrahydro-9H-beta-carbolin-9-yl]benzyl}cyclopropyl)amino]carbonyl}benzene-sulfonamide | 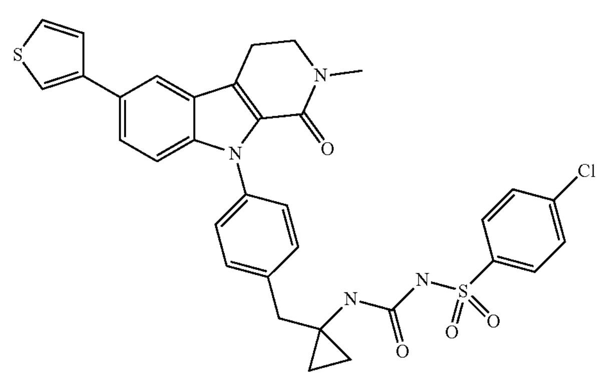 [SMILES: CN1CCc2c(n(-c3ccc(CC4(NC(=O)NS(=O)(=O)c5ccc(Cl)cc5)CC4)cc3)c3ccc(-c4ccsc4)cc23)C1=O] | 643.1 (M − H) |

TABLE 1-continued

| Ex | IUPAC name | Structure | MS |
|---|---|---|---|
| 1-26 | 4-chloro-N-[({1-[4-(2-methyl-1-oxo-6-pyridin-2-yl-1,2,3,4-tetrahydro-9H-beta-carbolin-9-yl)benzyl]cyclopropyl}amino)carbonyl]benzenesulfonamide | 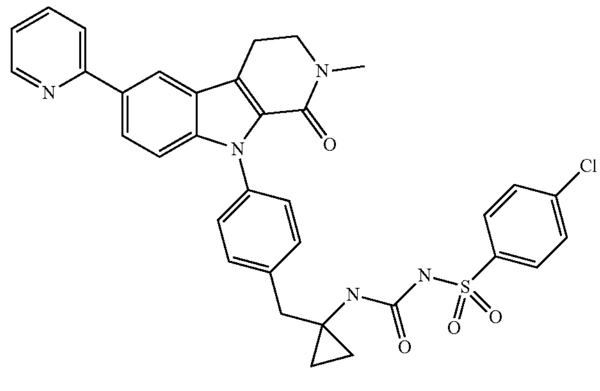 [SMILES: CN1CCc2c(n(-c3ccc(CC4(NC(=O)NS(=O)(=O)c5ccc(Cl)cc5)CC4)cc3)c3ccc(-c4ccccn4)cc23)C1=O] | 640.0 (M + H) |
| 1-27 | 4-chloro-N-{[(1-{4-[2-methyl-6-(2-methylphenyl)-1-oxo-1,2,3,4-tetrahydro-9H-beta-carbolin-9-yl]benzyl}cyclopropyl)amino]carbonyl}benzenesulfonamide | 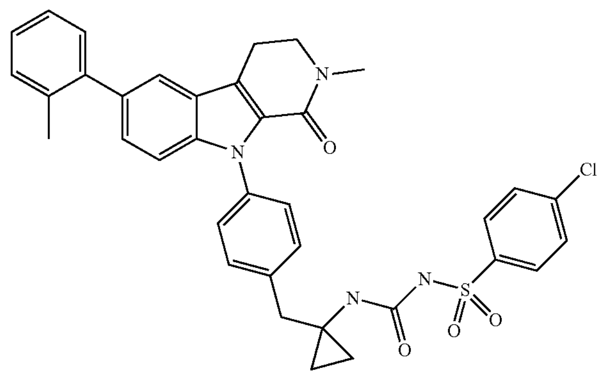 [SMILES: Cc1ccccc1-c1ccc2c(c1)c1c(n2-c2ccc(CC3(NC(=O)NS(=O)(=O)c4ccc(Cl)cc4)CC3)cc2)C(=O)N(C)CC1] | 651.1 (M − H) |
| 1-28 | 4-chloro-N-[({1-[4-(2,5,7-trimethyl-1-oxo-1,2,3,4-tetrahydro-9H-beta-carbolin-9-yl)benzyl]cyclopropyl}amino)carbonyl]benzenesulfonamide | 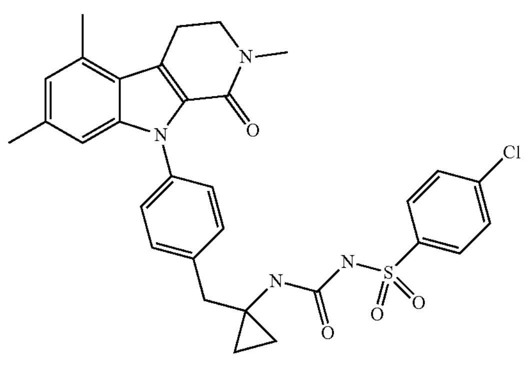 [SMILES: Cc1cc(C)c2c3c(n(-c4ccc(CC5(NC(=O)NS(=O)(=O)c6ccc(Cl)cc6)CC5)cc4)c2c1)C(=O)N(C)CC3] | 591.1 (M + H) |
| 1-29 | 2,6-dichloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | 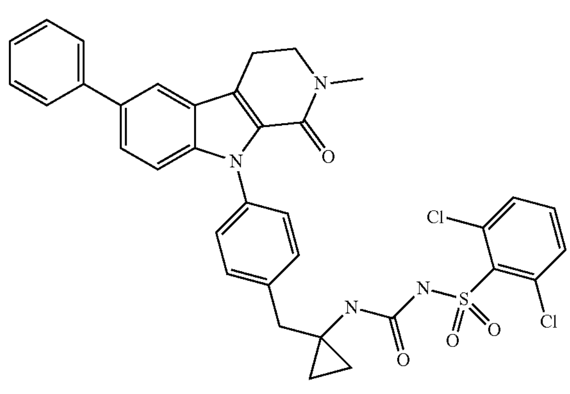 [SMILES: CN1CCc2c(n(-c3ccc(CC4(NC(=O)NS(=O)(=O)c5c(Cl)cccc5Cl)CC4)cc3)c3ccc(-c4ccccc4)cc23)C1=O] | 671.1 (M − H) |

TABLE 1-continued

| Ex | IUPAC name | Structure | MS |
|---|---|---|---|
| 1-30 | 2,6-dimethoxy-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | 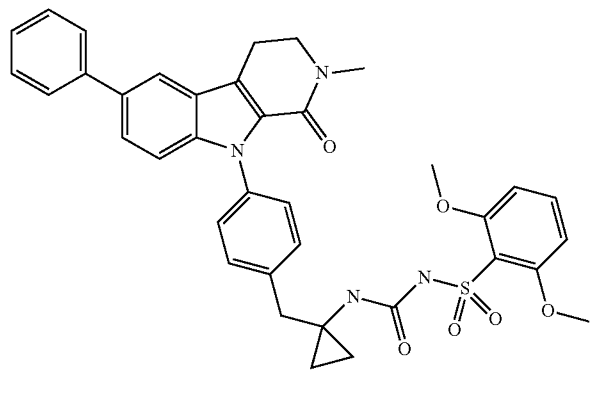 [SMILES: COc1cccc(OC)c1S(=O)(=O)NC(=O)NC1(Cc2ccc(-n3c4c(c5cc(-c6ccccc6)ccc53)CCN(C)C4=O)cc2)CC1] | 663.2 (M − H) |
| 1-31 | 4-chloro-N-{[(2-{4-[2-methyl-6-(methylsulfonyl)-1-oxo-1,2,3,4-tetrahydro-9H-beta-carbolin-9-yl]phenyl}ethyl)amino]carbonyl}benzenesulfonamide | 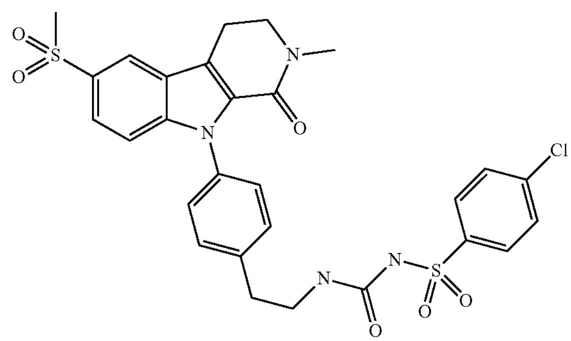 [SMILES: CN1CCc2c(n(-c3ccc(CCNC(=O)NS(=O)(=O)c4ccc(Cl)cc4)cc3)c3ccc(S(C)(=O)=O)cc23)C1=O] | 615.6 (M + H) |
| 1-32 | 4-chloro-N-{[(2-{4-[2-methyl-7-(methylsulfonyl)-1-oxo-1,2,3,4-tetrahydro-9H-beta-carbolin-9-yl]phenyl}ethyl)amino]carbonyl}benzenesulfonamide | 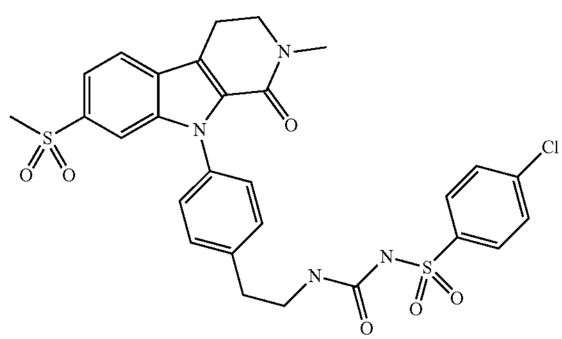 [SMILES: CN1CCc2c(n(-c3ccc(CCNC(=O)NS(=O)(=O)c4ccc(Cl)cc4)cc3)c3cc(S(C)(=O)=O)ccc23)C1=O] | 615.6 (M + H) |
| 1-33 | 4-chloro-N-{[(2-{4-[2-methyl-5-(methylsulfonyl)-1-oxo-1,2,3,4-tetrahydro-9H-beta-carbolin-9-yl]phenyl}ethyl)amino]carbonyl}benzenesulfonamide | 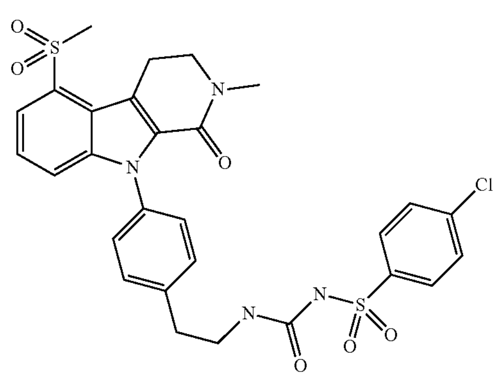 [SMILES: CN1CCc2c(n(-c3ccc(CCNC(=O)NS(=O)(=O)c4ccc(Cl)cc4)cc3)c3cccc(S(C)(=O)=O)c23)C1=O] | 615.6 (M + H) |

TABLE 1-continued

| Ex | IUPAC name | Structure | MS |
|---|---|---|---|
| 1-34 | 4-chloro-N-{[(1-{4-[2-methyl-6-(methylsulfonyl)-1-oxo-1,2,3,4-tetrahydro-9H-beta-carbolin-9-yl]benzyl}cyclopropyl)amino]carbonyl}benzenesulfonamide | 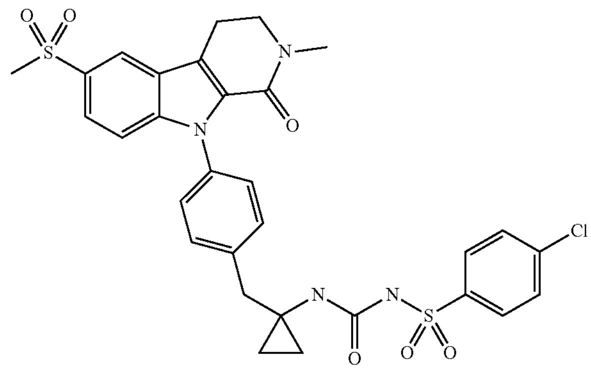 | 614.1 (M + H) |
| 1-35 | 4-chloro-N-({[2-(4-{2-methyl-6-[4-(methylsulfonyl)phenyl]-1-oxo-1,2,3,4-tetrahydro-9H-beta-carbolin-9-yl}phenyl)ethyl]amino}carbonyl)benzenesulfonamide | 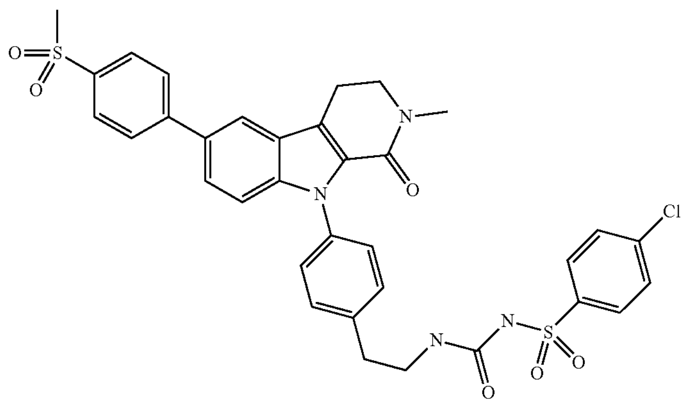 | 614.1 (M + H) |
| 1-36 | 4-chloro-N-({[2-(4-{2-methyl-6-[3-(methylsulfonyl)phenyl]-1-oxo-1,2,3,4-tetrahydro-9H-beta-carbolin-9-yl}phenyl)ethyl]amino}carbonyl)benzenesulfonamide | 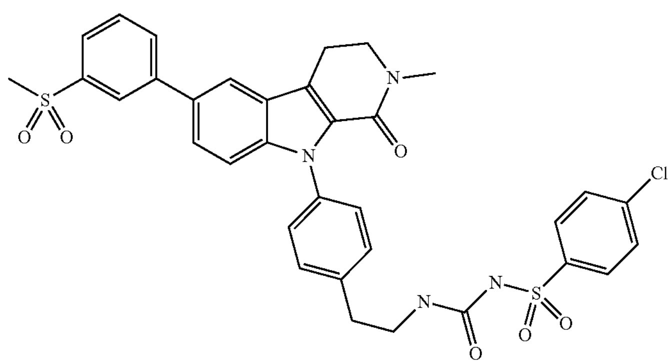 | 577.1 (M + H) |
| 1-37 | 4-chloro-N-{[(1-{4-[2-methyl-1-oxo-6-(phenylsulfonyl)-1,2,3,4-tetrahydro-9H-beta-carbolin-9-yl]benzyl}cyclopropyl)amino]carbonyl}benzenesulfonamide | 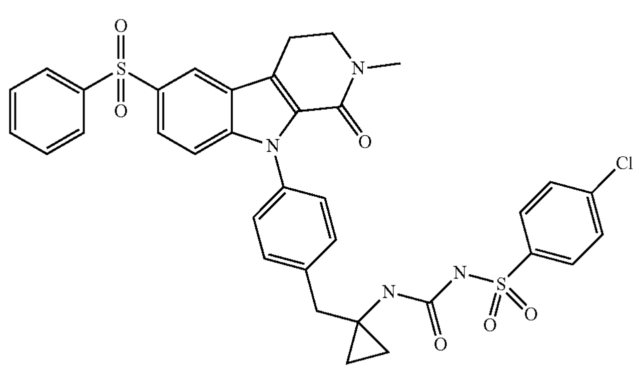 [SMILES: CN1CCc2c(n(-c3ccc(CC4(NC(=O)NS(=O)(=O)c5ccc(Cl)cc5)CC4)cc3)c3ccc(S(=O)(=O)c4ccccc4)cc23)C1=O] | 701.1 (M − H) |

EXAMPLE 2

4-chloro-N-[({1-[4-(6-cyclopropyl-2-methyl-1-oxo-1,2,3,4-tetrahydro-9H-beta-carbolin-9-yl)benzyl]cyclopropyl}amino)carbonyl]benzenesulfonamide (2-1)

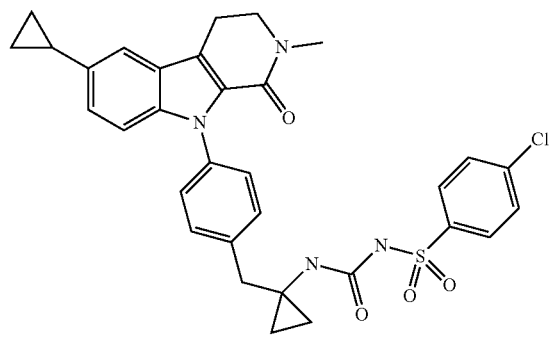 [SMILES: CN1CCc2c(n(-c3ccc(CC4(NC(=O)NS(=O)(=O)c5ccc(Cl)cc5)CC4)cc3)c3ccc(C4CC4)cc23)C1=O]
2-1

Step 1(a)-(c): RE 1a, RE 1b, and RE 1c

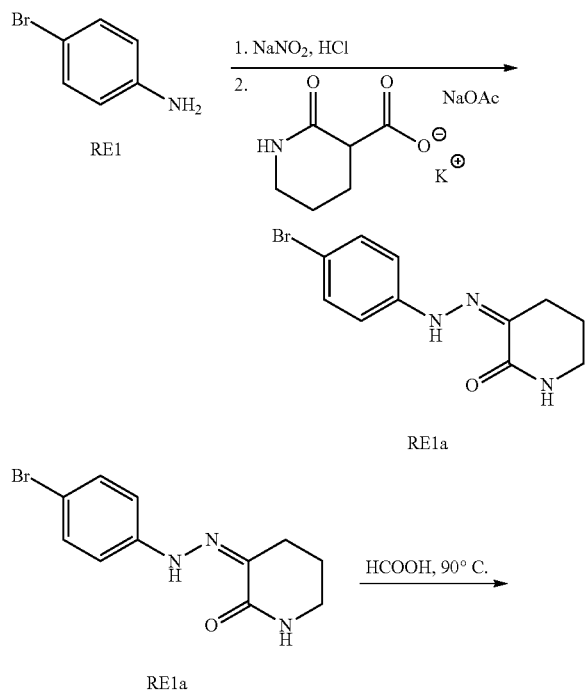

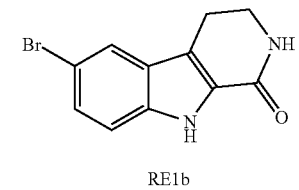

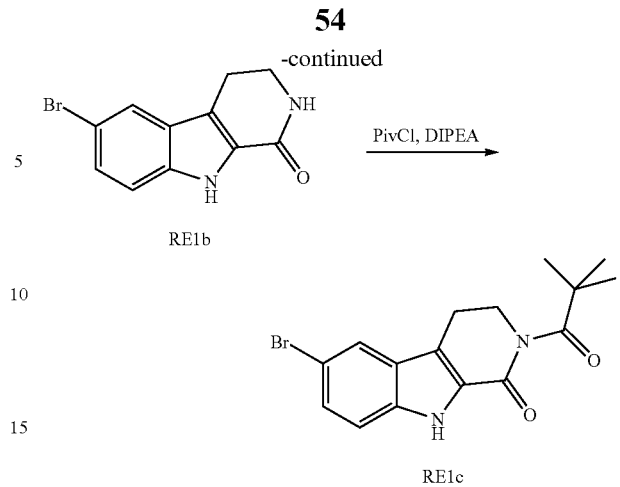

Step 1(a)

To a solution of 3-carbethoxy-2-piperidone (49.7 g, 290 mmol) in H₂O (500 mL) was added solid KOH (17.1 g, 305 mmol) and the mixture was stirred overnight at rt ("carboxylate solution"). In a separate reaction flask, approximately 200 g of ice was added to a suspension of the aniline (50.0 g, 290 mmol) in 100 mL conc. HCl(aq), and the mixture was cooled to 0° C. To this mixture was added a solution of NaNO₂ (22.0 g, 319 mmol) in H₂O (100 mL) via dropping funnel over approximately 1 hour. The mixture became homogeneous, and was stirred for an additional hour at 0° C. ("diazonium solution"). To the carboxylate solution was added approximately 200 g ice, and this solution was chilled to 0° C. The diazonium solution was then transferred to an addition funnel, approximately 200 g of ice was added, and this solution was added to the carboxylate over approximately 1.5 hours. When the addition was complete, the pH of the mixture was adjusted to approximately 4 using approximately 150 mL of sat. NaOAc(aq), and the resulting mixture was stirred for 3 hours at 0° C. The fine precipitate which was formed was removed by filtration through a medium porosity fitted funnel, and rinsed with 3×200 mL H₂O and 2×200 mL Et₂O, then air dried overnight to provide 44 g of approximately 90% purity diazolactam (RE1a) as a light yellow solid which was used directly without further purification.

Step 1(b)

A solution of the diazolactam (44.0 g, approximately 90% purity) in formic acid (250 mL) was heated to 90° C. for 90 minutes, at which point a solid had formed. The mixture was cooled to rt, then diluted with 500 mL H₂O. The resulting light brown solid was removed by filtration, then washed with 100 mL H₂O, 100 mL 2 M Na₂CO₃(aq), 2×100 mL H₂O then 100 mL cold Et₂O. The resulting solid was air dried then pumped under high vacuum to provide 37.6 g (142 mmol, 49% (2 steps)) of indole as a light yellow solid (RE1b).

Step 1(c)

To a solution of the lactam (19.0 g, 71.7 mmol) in toluene (150 mL) was added Hunig's base (25.0 mL, 143 mmol) then pivaloyl chloride (9.70 mL, 78.9 mmol). The mixture was heated to 110° C. for 2 hours, then cooled to rt. An additional 2.0 mL (16.3 mmol) of pivaloyl chloride was added, and heating continued for an additional 2 hours. After cooling to rt, the red solution was poured into H₂O (250 mL) and the product extracted with ethyl acetate (3×200 mL). The combined organic fractions were washed with brine (200 mL), dried (Na₂SO₄) and concentrated in vacuo. Purification by flash column chromatography (80:20 hexanes:EtOAc) provided 11.2 g (32.0 mmol, 45%) of the desired protected lactam (RE1c) as a yellow powder.
Step 2 (a) and (b): RE 2a and RE 2b

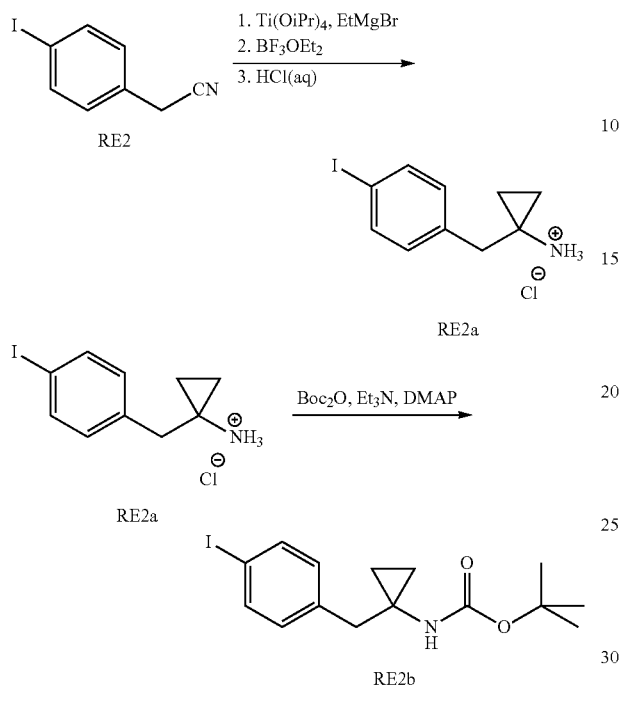

Step 2(a)

A solution of the nitrile (50.0 g, 206 mmol) in toluene (500 mL) was cooled to −25° C., then Ti(O$^i$Pr)$_4$ (60.3 mL, 206 mmol) was added. A commercial (Aldrich) solution of EtMgBr (3.0 M, 137 mL, 411 mmol) was then added dropwise at a rate which maintained the internal temperature between −20 and −25° C. (over approximately 60 minutes). The mixture was stirred for 60 minutes at this temperature, then the BF$_3$OEt$_2$ (52.1 mL, 411 mmol) was added dropwise maintaining a constant internal temperature (over approximately 30 minutes). After stirring the resulting solution for 60 minutes, the mixture was poured into 750 mL 3 N HCl(aq) and stirred rapidly for 30 minutes while warming to room temperature. The mixture was then transferred to a separatory funnel, and allowed to settle for 30 minutes. The thick yellow oil which separated on the bottom was carefully removed, then dissolved in CH$_2$Cl$_2$ (1 L), dried (Na$_2$SO$_4$) and concentrated in vacuo to provide 24 g of the amine salt (RE2a) of sufficient purity (approximately 80%) to be used directly.
Step 2(b)

To a solution of the amine salt (24 g, approximately 80% purity, approximately 78 mmol) in MeOH was added Et$_3$N (27.2 mL, 195 mmol) and Boc$_2$O (17.1 g, 78 mmol) and DMAP. The mixture was stirred for 24 hours at rt. NMR analysis of an aliquot indicated only approximately 60% conversion, so an extra equivalent of Boc$_2$O (17.1 g) and Et$_3$N (10.9 mL) were added, and stirring continued for an additional 24 hours. NMR analysis at this stage showed approximately 80% conversion, so another equivalent of Boc$_2$O (17.1 g) and Et$_3$N (10.9 mL) were added and the mixture was stirred for an additional 24 hours. MeOH was then removed in vacuo, then the residue was diluted with Et$_2$O (400 mL) and washed with H$_2$O (400 mL) and brine (400 mL). The aqueous fractions were further extracted with Et$_2$O (400 mL), then the combined organic extracts were dried (Na$_2$SO$_4$; CH$_2$Cl$_2$ added) and concentrated in vacuo. Purification by flash column chromatography (dry load; 100:0 to 80:20 hexanes:EtOAc, linear gradient) provided 12.0 g (30.5 mmol, 15% (2 steps)) of N-Boc cyclopropyl amine (RE2b) as a yellow solid of approximately 95% purity.
Step 3: RE 3

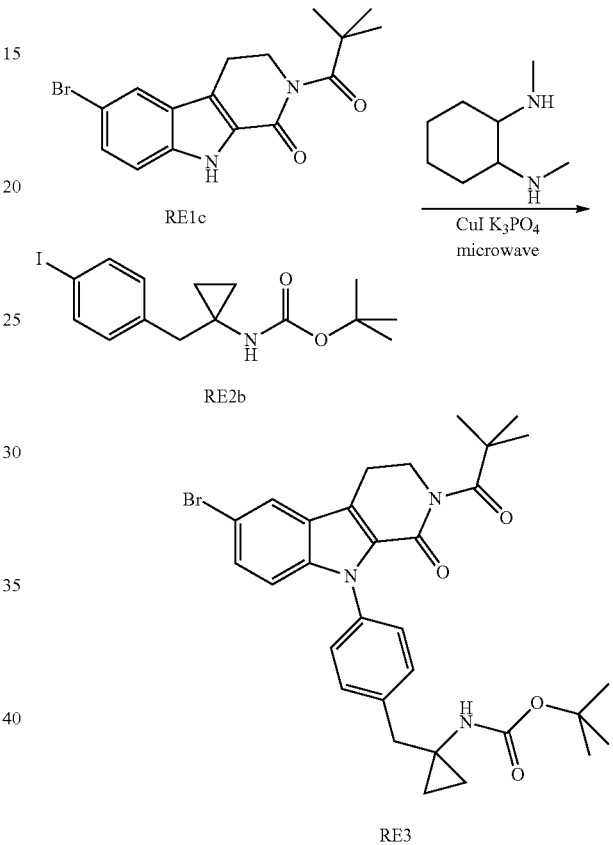

To a mixture of the iodide (1.00 g, 2.68 mmol), carboline (0.982 g, 2.81 mmol), CuI (0.102 g, 0.536 mol) and K$_3$PO$_4$ (1.14 g, 5.36 mmol) in a microwave vial was added toluene that had been degassed by bubbling N$_2$ through for approximately 15 minutes. The ligand (rac-trans-N,N'-dimethylcyclohexane-1,2-diamine, 0.169 mL, 1.07 mmol) was then added, and the mixture was capped and placed in the microwave generator for 30 minutes at 110° C. The mixture was then diluted with H$_2$O (100 mL) and extracted with CH$_2$Cl$_2$ (2×100 mL). The combined organic extracts were dried (Na$_2$SO$_4$) and concentrated in vacuo. Purification by flash column chromatography (load w/CH$_2$Cl$_2$; 100:0 to 60:40 hexanes:EtOAc, linear gradient) provided 468 mg of N-aryl carboline as a approximately 5:1 mixture of bromide:iodide at the 5-position of the carboline. The bromide:iodide ratio obtained is variable, but the mixture can be used directly in downstream coupling processes.

Step 4(a) and (b): RE 4b and RE 4c

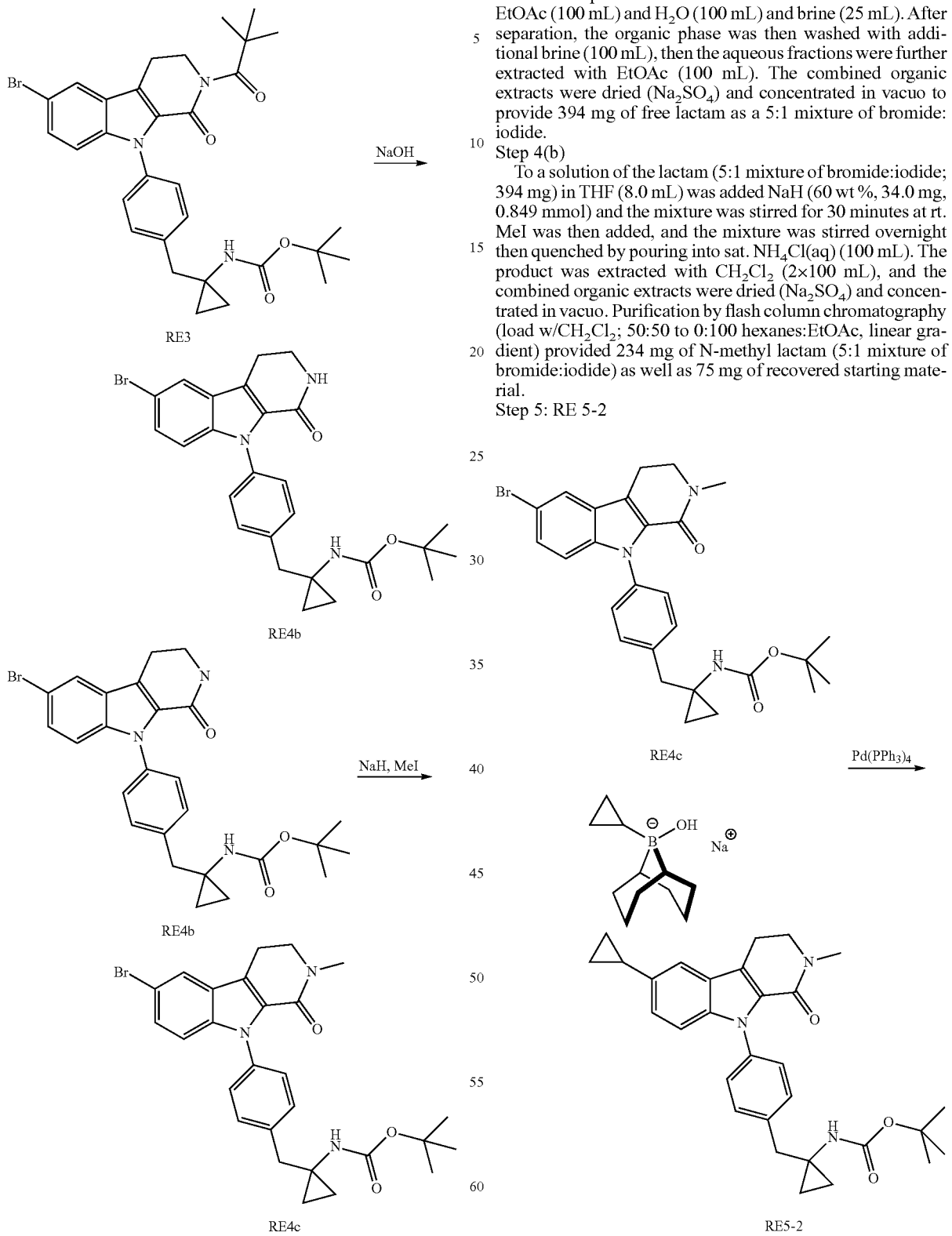

Step 4(a)
To a solution of the N-Piv carboline (5:1 mixture of bromide:iodide; 468 mg) in 1:1 MeOH/THF (8 mL) was added NaOH(aq) (2 M, 1.57 mL, 3.15 mmol) and the mixture was stirred for 45 minutes at rt, at which point TLC analysis showed complete conversion. The mixture was diluted with EtOAc (100 mL) and H₂O (100 mL) and brine (25 mL). After separation, the organic phase was then washed with additional brine (100 mL), then the aqueous fractions were further extracted with EtOAc (100 mL). The combined organic extracts were dried (Na₂SO₄) and concentrated in vacuo to provide 394 mg of free lactam as a 5:1 mixture of bromide:iodide.

Step 4(b)
To a solution of the lactam (5:1 mixture of bromide:iodide; 394 mg) in THF (8.0 mL) was added NaH (60 wt %, 34.0 mg, 0.849 mmol) and the mixture was stirred for 30 minutes at rt. MeI was then added, and the mixture was stirred overnight then quenched by pouring into sat. NH₄Cl(aq) (100 mL). The product was extracted with CH₂Cl₂ (2×100 mL), and the combined organic extracts were dried (Na₂SO₄) and concentrated in vacuo. Purification by flash column chromatography (load w/CH₂Cl₂; 50:50 to 0:100 hexanes:EtOAc, linear gradient) provided 234 mg of N-methyl lactam (5:1 mixture of bromide:iodide) as well as 75 mg of recovered starting material.

Step 5: RE 5-2

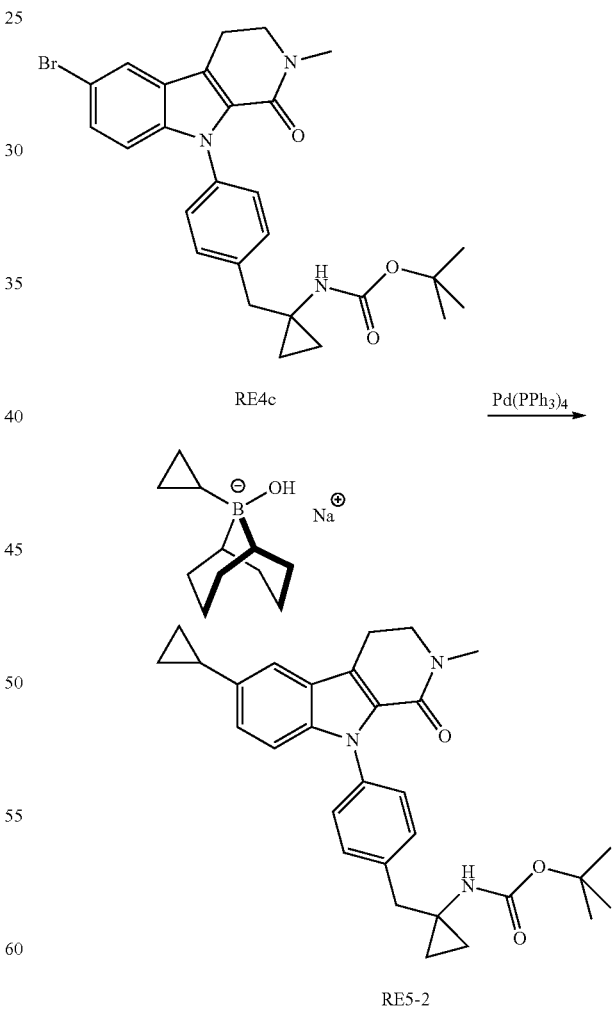

Reference: TL, 2000, 41, 4251

To a suspension of 9-BBN dimer (1.22 g, 5.00 mmol) in THF (5.0 mL) was added propargyl bromide (0.555 mL, 5.00 mmol) and the mixture was heated to reflux for 2 hours. The homogeneous solution was cooled to rt, then 3 M NaOH(aq) (5.00 mL, 15.0 mmol) was added and the mixture was stirred for 1 hour at rt. The homogeneous solution was used directly as a 0.5 M solution of the boronate. To a sample of this boronate solution (0.5 M, 1.91 mL, 0.953 mmol) was added the bromocarboline (200 mg, 0.381 mmol) and Pd(PPh₃)₄ (88 mg, 0.076 mmol) and the mixture was heated to 75° C. overnight. The mixture was then cooled to rt and filtered through a plug of SiO₂ and NaHCO₃ with EtOAc as the eluent, followed by in vacuo concentration. Purification by flash column chromatography (load w/CH₂Cl₂; 50:50 to 10:90 hexanes:EtOAc, linear gradient) provided 170 mg (0.344 mmol, 90%) of the cyclopropyl arene (RE5-2) as an off-white foam.

Step 6(a) and (b): RE 6b and RE 6c

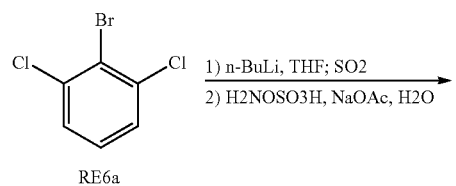

RE6a

RE6b

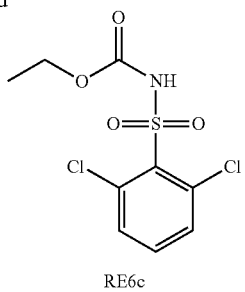

RE6c

Step 6(a)

To a solution of 1-bromo-2,6-dichlorobenzene (4.34 g, 19.2 mmol) in THF (20 mL) at −78° C. was added n-BuLi (1.6 M in hexanes, 10.0 mL, 16.0 mmol). The reaction mixture (precipitate formed with time) was stirred at −78° C. for 4 hours. Sulfur dioxide was then bubbled into the mixture for 15 min. The yellow solution was warmed to RT, during which time a colorless precipitate formed. After 30 min at RT, hexanes were added and the sulfinic salt was removed by filtration. The salt was dissolved in water (50 mL) and sodium acetate (3.28 g, 40.0 mmol) was added. The solution was cooled to 10° C. and hydroxylamine-O-sulfonic acid (2.26 g, 20.0 mmol) was added. The ice-water bath was removed, and a white product precipitated out within minutes. The reaction was stirred at RT overnight. The reaction was extracted with EtOAc (3×50 mL), and the combined organic layers were washed with 5% NaHCO₃(aq) (50 mL) and brine (50 mL), then dried (Na₂SO₄) and concentrated in vacuo to provide 2.66 g (11.8 mmol, 74%) of the sulfonamide (RE6b) as a white solid.

Step 6(b)

To a heterogeneous mixture of sulfonamide (14.5 g, 64.1 mmol) and potassium carbonate (31.0 g, 224 mmol) in acetone (130 mL) was added ethyl chloroformate (15.4 mL, 160 mmol). The reaction was heated to reflux overnight, then cooled to rt, and quenched by the addition of 200 mL 1 N HCl(aq). The product was extracted with EtOAc (3×200 mL), and the combined organic extracts were dried (Na₂SO₄) and concentrated in vacuo to provide 18.8 g (63.1 mmol, 98%) of pure sulfonyl carbamate (RE6c) as a white solid.

Note: Steps 7(a) and (b) have Procedures Analogous to the Ones Described in Example 1 Steps 7(a) and (b).

Compounds (Examples 2-2 through 2-4) were prepared in a similar manner as the compound, Example 2-1, but using the appropriate boronate to generate the desired product.

TABLE 2

| Ex | IUPAC name | Structure | MS |
|---|---|---|---|
| 2-1 | 4-chloro-N-[({1-[4-(6-cyclopropyl-2-methyl-1-oxo-1,2,3,4-tetrahydro-9H-beta-carbolin-9-yl)benzyl]cyclopropyl}amino)carbonyl]benzenesulfonamide | 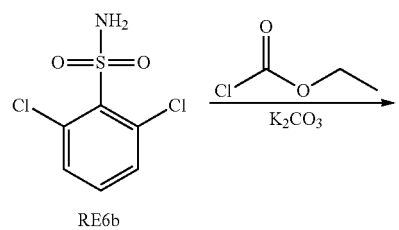 | 603.1 (M + H) |

TABLE 2-continued

| Ex | IUPAC name | Structure | MS |
|---|---|---|---|
| 2-2 | 4-chloro-N-[({2-[4-(6-cyclopropyl-2-methyl-1-oxo-1,2,3,4-tetrahydro-9H-beta-carbolin-9-yl)phenyl]ethyl}amino)carbonyl]benzenesulfonamide | 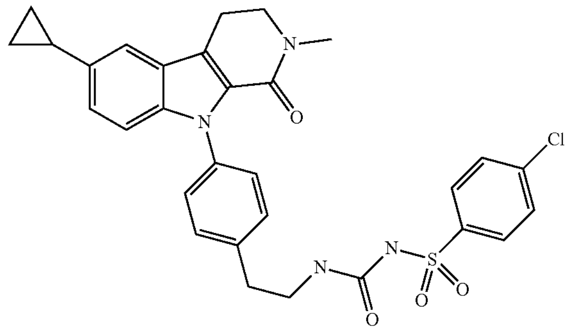 [SMILES: CN1CCc2c(n(-c3ccc(CCNC(=O)NS(=O)(=O)c4ccc(Cl)cc4)cc3)c3ccc(C4CC4)cc23)C1=O] | 629.1 (M − H) |
| 2-3 | 4-chloro-N-[({2-[4-(5-cyclopropyl-2-methyl-1-oxo-1,2,3,4-tetrahydro-9H-beta-carbolin-9-yl)phenyl]ethyl}amino)carbonyl]benzenesulfonamide | 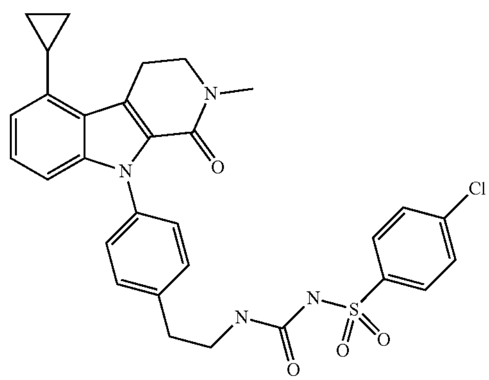 | 641.0 (M + H) |
| 2-4 | 4-chloro-N-[({2-[4-(7-cyclopropyl-2-methyl-1-oxo-1,2,3,4-tetrahydro-9H-beta-carbolin-9-yl)phenyl]ethyl}amino)carbonyl]benzenesulfonamide | 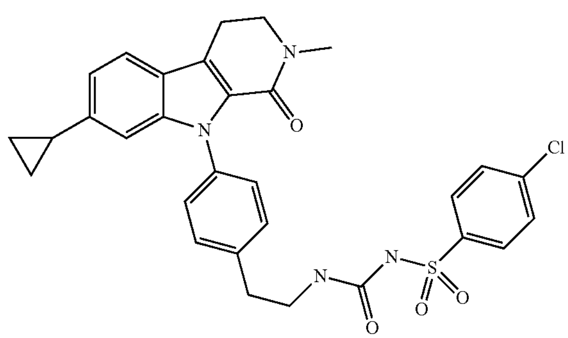 [SMILES: CN1CCc2c(n(-c3ccc(CCNC(=O)NS(=O)(=O)c4ccc(Cl)cc4)cc3)c3cc(C4CC4)ccc23)C1=O] | 663.1 (M + Na) |

EXAMPLE 3 sodium[(4-chlorophenyl)sulfonyl]{[(1-{4-[2-methyl-6-(5-methyl-1,3,4-oxadiazol-2-yl)-1-oxo-1,2,3,4-tetrahydro-9H-beta-carbolin-9-yl]benzyl}cyclopropyl)amino]carbonyl}azanide (3-1)

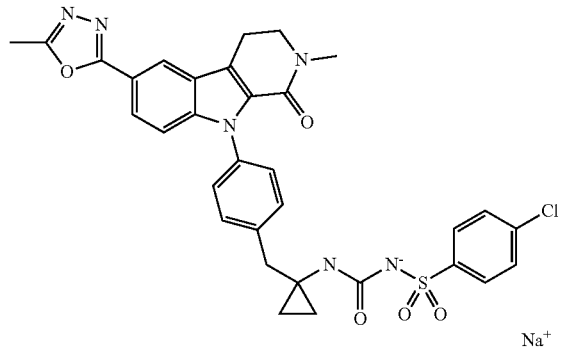

Step 1(a)-(c): RE 1a, RE 1b, and RE 1c

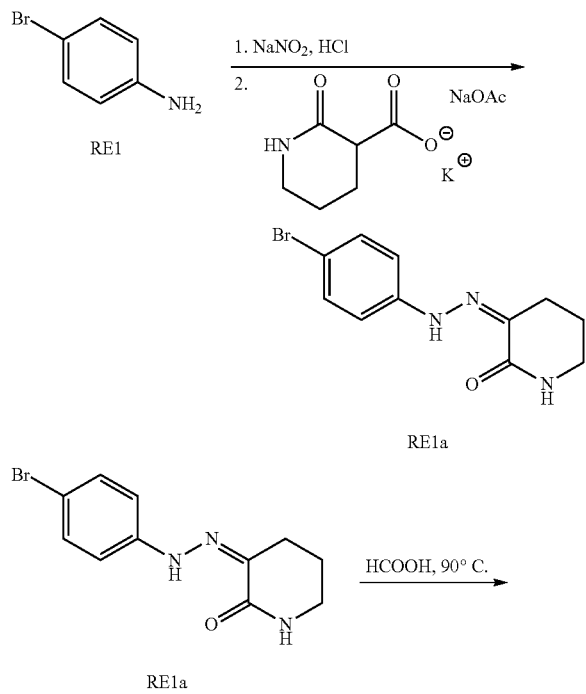

Step 1(a)

To a solution of 3-carbethoxy-2-piperidone (49.7 g, 290 mmol) in $H_2O$ (500 mL) was added solid KOH (17.1 g, 305 mmol) and the mixture was stirred overnight at rt ("carboxylate solution"). In a separate reaction flask, approximately 200 g of ice was added to a suspension of the aniline (50.0 g, 290 mmol) in 100 mL conc. HCl(aq), and the mixture was cooled to 0° C. To this mixture was added a solution of $NaNO_2$ (22.0 g, 319 mmol) in $H_2O$ (100 mL) via dropping funnel over approximately 1 hour. The mixture became homogeneous, and was stirred for an additional hour at 0° C. ("diazonium solution"). To the carboxylate solution was added approximately 200 g ice, and this solution was chilled to 0° C. The diazonium solution was then transferred to an addition funnel, approximately 200 g of ice was added, and this solution was added to the carboxylate over approximately 1.5 hours. When the addition was complete, the pH of the mixture was adjusted to approximately 4 using approximately 150 mL of sat. NaOAc(aq), and the resulting mixture was stirred for 3 hours at 0° C. The fine precipitate which was formed was removed by filtration through a medium porosity fritted funnel, and rinsed with 3×200 mL $H_2O$ and 2×200 mL $Et_2O$, then air dried overnight to provide 44 g of approximately 90% purity diazolactam (RE1a) as a light yellow solid which was used directly without further purification.

Step 1(b)

A solution of the diazolactam (44.0 g, approximately 90% purity) in formic acid (250 mL) was heated to 90° C. for 90 minutes, at which point a solid had formed. The mixture was cooled to rt, then diluted with 500 mL $H_2O$. The resulting light brown solid was removed by filtration, then washed with 100 mL $H_2O$, 100 mL 2 M $Na_2CO_3$(aq), 2×100 mL $H_2O$ then 100 mL cold $Et_2O$. The resulting solid was air dried then pumped under high vacuum to provide 37.6 g (142 mmol, 49% (2 steps)) of indole as a light yellow solid (RE1b).

Step 1(c)

To a solution of the lactam (19.0 g, 71.7 mmol) in toluene (150 mL) was added Hunig's base (25.0 mL, 143 mmol) then pivaloyl chloride (9.70 mL, 78.9 mmol). The mixture was heated to 110° C. for 2 hours, then cooled to rt. An additional 2.0 mL (16.3 mmol) of pivaloyl chloride was added, and heating continued for an additional 2 hours. After cooling to rt, the red solution was poured into $H_2O$ (250 mL) and the product extracted with ethyl actetate (3×200 mL). The combined organic fractions were washed with brine (200 mL), dried ($Na_2SO_4$) and concentrated in vacuo. Purification by flash column chromatography (80:20 hexanes:EtOAc) provided 11.2 g (32.0 mmol, 45%) of the desired protected lactam (RE1c) as a yellow powder.

Step 2 (a) and (b): RE 2a and RE 2b

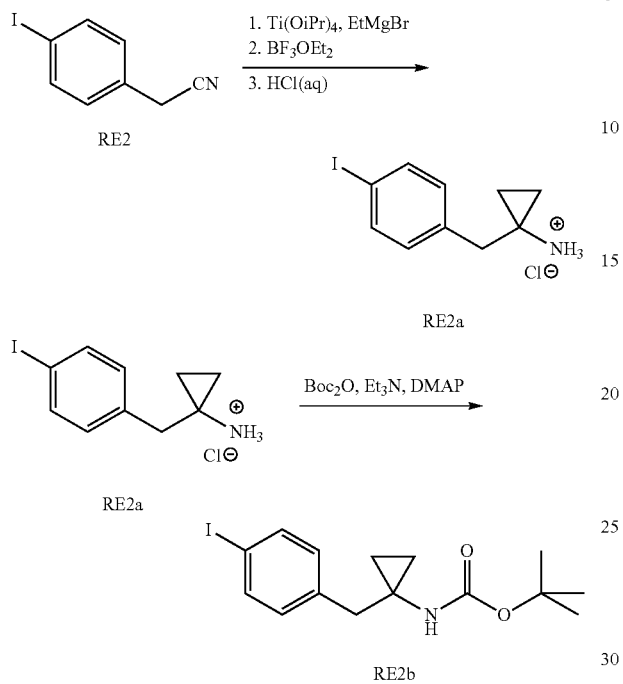

Step 2(a)

A solution of the nitrile (50.0 g, 206 mmol) in toluene (500 mL) was cooled to −25° C., then Ti(O$^i$Pr)$_4$ (60.3 mL, 206 mmol) was added. A commercial (Aldrich) solution of EtMgBr (3.0 M, 137 mL, 411 mmol) was then added dropwise at a rate which maintained the internal temperature between −20 and −25° C. (over approximately 60 minutes). The mixture was stirred for 60 minutes at this temperature, then the BF$_3$OEt$_2$ (52.1 mL, 411 mmol) was added dropwise maintaining a constant internal temperature (over approximately 30 minutes). After stirring the resulting solution for 60 minutes, the mixture was poured into 750 mL 3 N HCl(aq) and stirred rapidly for 30 minutes while warming to room temperature. The mixture was then transferred to a separatory funnel, and allowed to settle for 30 minutes. The thick yellow oil which separated on the bottom was carefully removed, then dissolved in CH$_2$Cl$_2$ (1 L), dried (Na$_2$SO$_4$) and concentrated in vacuo to provide 24 g of the amine salt (RE2a) of sufficient purity (approximately 80%) to be used directly.

Step 2(b)

To a solution of the amine salt (24 g, approximately 80% purity, approximately 78 mmol) in MeOH was added Et$_3$N (27.2 mL, 195 mmol) and Boc$_2$O (17.1 g, 78 mmol) and DMAP. The mixture was stirred for 24 hours at it NMR analysis of an aliquot indicated only approximately 60% conversion, so an extra equivalent of Boc$_2$O (17.1 g) and Et$_3$N (10.9 mL) were added, and stirring continued for an additional 24 hours. NMR analysis at this stage showed approximately 80% conversion, so another equivalent of Boc$_2$O (17.1 g) and Et$_3$N (10.9 mL) were added and the mixture was stirred for an additional 24 hours. MeOH was then removed in vacuo, then the residue was diluted with Et$_2$O (400 mL) and washed with H$_2$O (400 mL) and brine (400 mL). The aqueous fractions were further extracted with Et$_2$O (400 mL), then the combined organic extracts were dried (Na$_2$SO$_4$; CH$_2$Cl$_2$ added) and concentrated in vacuo. Purification by flash column chromatography (dry load; 100:0 to 80:20 hexanes:EtOAc, linear gradient) provided 12.0 g (30.5 mmol, 15% (2 steps)) of N-Boc cyclopropyl amine (RE2b) as a yellow solid of approximately 95% purity.

Step 3: RE 3

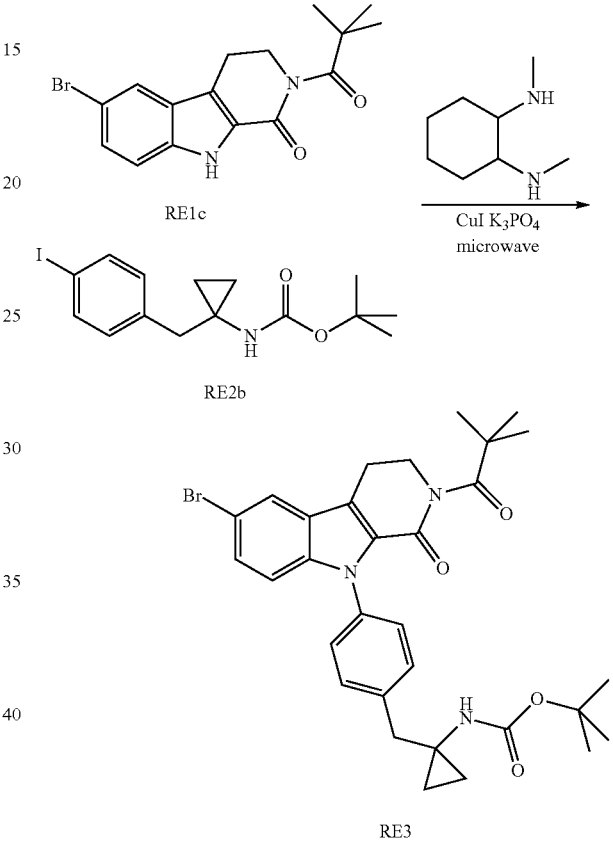

To a mixture of the iodide (1.00 g, 2.68 mmol), carboline (0.982 g, 2.81 mmol), CuI (0.102 g, 0.536 mol) and K$_3$PO$_4$ (1.14 g, 5.36 mmol) in a microwave vial was added toluene that had been degassed by bubbling N$_2$ through for approximately 15 minutes. The ligand (rac-trans-N,N'-dimethylcyclohexane-1,2-diamine, 0.169 mL, 1.07 mmol) was then added, and the mixture was capped and placed in the microwave generator for 30 minutes at 110° C. The mixture was then diluted with H$_2$O (100 mL) and extracted with CH$_2$Cl$_2$ (2×100 mL). The combined organic extracts were dried (Na$_2$SO$_4$) and concentrated in vacuo. Purification by flash column chromatography (load w/CH$_2$Cl$_2$; 100:0 to 60:40 hexanes:EtOAc, linear gradient) provided 468 mg of N-aryl carboline as a approximately 5:1 mixture of bromide:iodide at the 5-position of the carboline. The bromide:iodide ratio obtained is variable, but the mixture can be used directly in downstream coupling processes.

Step 4(a) and (b): RE 4b and RE 4c

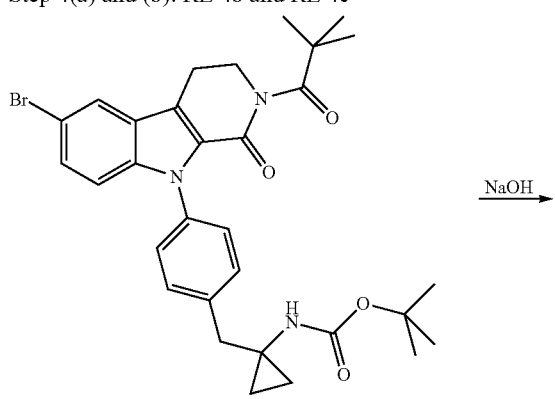

RE3

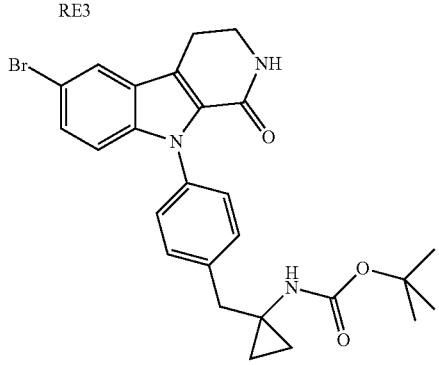

RE4b

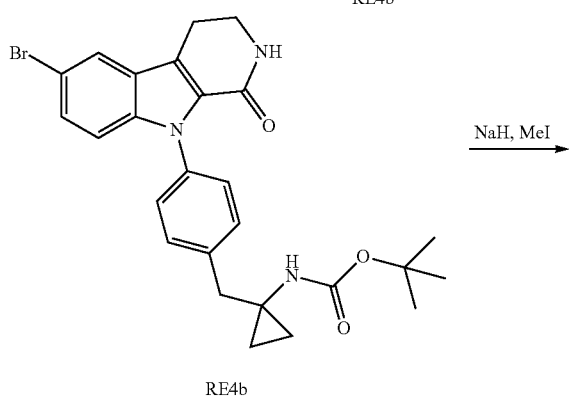

RE4b

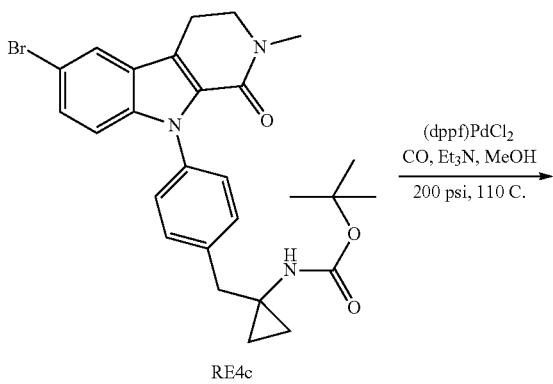

RE4c

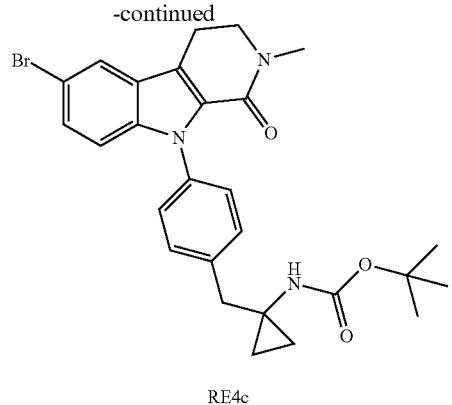

RE4c

Step 4(a)

To a solution of the N-Piv carboline (5:1 mixture of bromide:iodide; 468 mg) in 1:1 MeOH/THF (8 mL) was added NaOH(aq) (2 M, 1.57 mL, 3.15 mmol) and the mixture was stirred for 45 minutes at rt, at which point TLC analysis showed complete conversion. The mixture was diluted with EtOAc (100 mL) and $H_2O$ (100 mL) and brine (25 mL). After separation, the organic phase was then washed with additional brine (100 mL), then the aqueous fractions were further extracted with EtOAc (100 mL). The combined organic extracts were dried ($Na_2SO_4$) and concentrated in vacuo to provide 394 mg of free lactam as a 5:1 mixture of bromide:iodide.

Step 4(b)

To a solution of the lactam (5:1 mixture of bromide:iodide; 394 mg) in THF (8.0 mL) was added NaH (60 wt %, 34.0 mg, 0.849 mmol) and the mixture was stirred for 30 minutes at rt. MeI was then added, and the mixture was stirred overnight then quenched by pouring into sat. $NH_4Cl$(aq) (100 mL). The product was extracted with $CH_2Cl_2$ (2×100 mL), and the combined organic extracts were dried ($Na_2SO_4$) and concentrated in vacuo. Purification by flash column chromatography (load w/$CH_2Cl_2$; 50:50 to 0:100 hexanes:EtOAc, linear gradient) provided 234 mg of N-methyl lactam (5:1 mixture of bromide:iodide) as well as 75 mg of recovered starting material.

Step 5(a)-(d): RE 5-3, RE 5-3a, RE5-3b, and RE5-3c

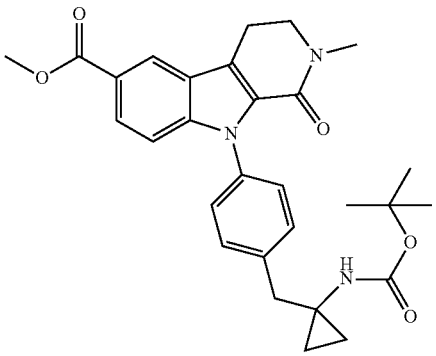

RE5-3

-continued
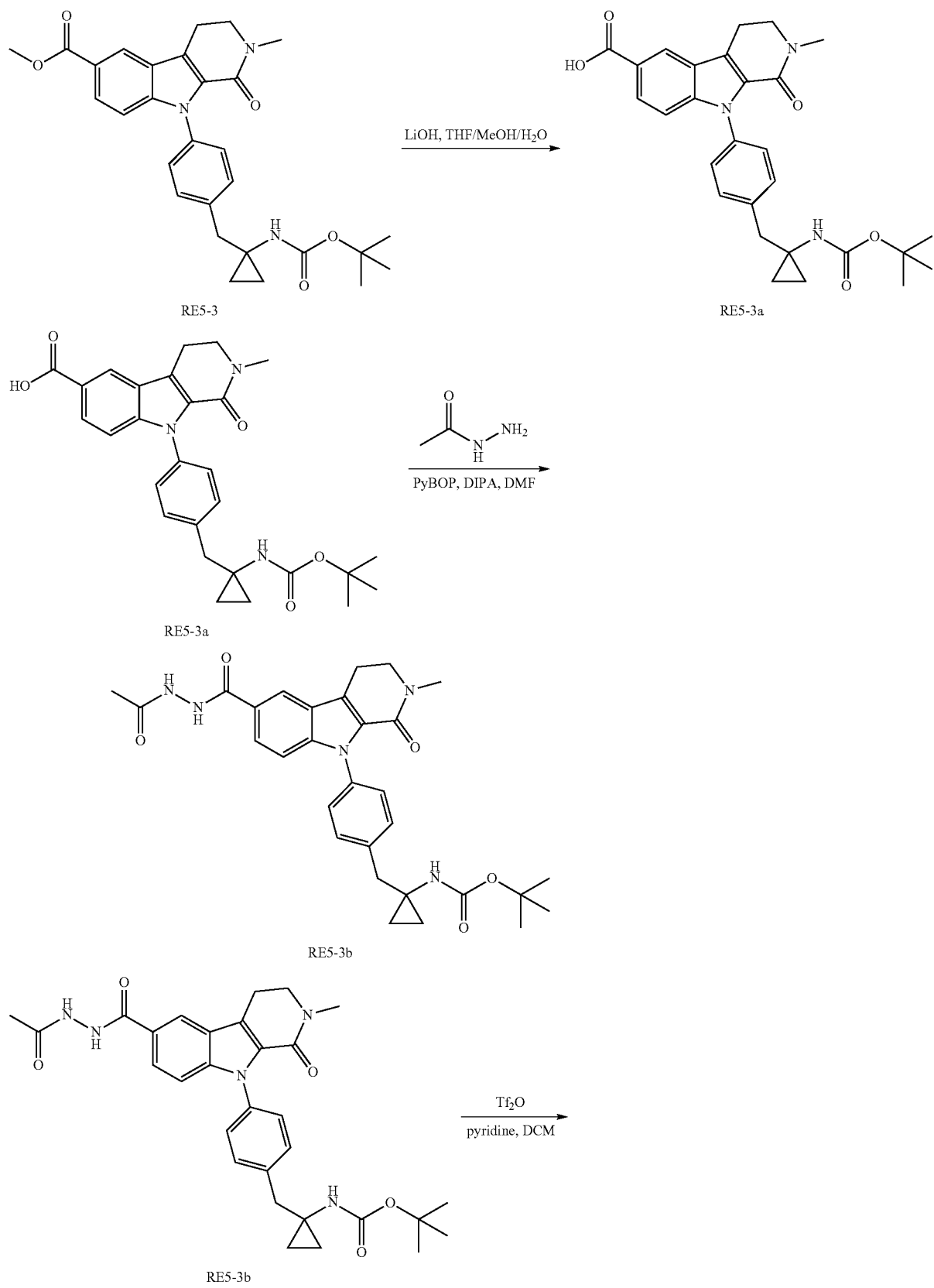

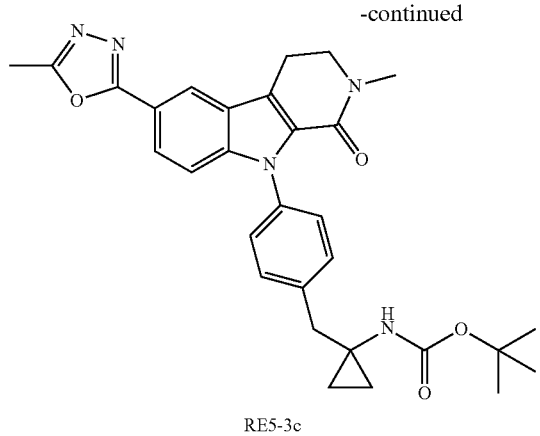

RE5-3c

Step 5(a)

A bomb was charged with the arylbromide (2.5:1 mixture with iodide; 75 mg), (dppf)PdCl$_2$ (9.60 mg, 0.013 mmol), triethylamine (0.027 mL, 0.197 mmol) and MeOH (1.6 mL). The vessel was charged and purged three times with CO (500 psi), then pressurized with CO (200 psi) and heated at 110° C. for 20 hours. The vessel was removed from the oil bath, cooled to RT and depressurized. In vacuo concentration and purification by flash column chromatography (80% EtOAc/hexanes, loaded with DCM and solvent system) to afford 62 mg (0.123 mmol) of the desired ester (RE5-3) as a light beige solid.

Step 5(b)

To a solution of methyl ester (254 mg, 0.504 mmol) in a mixture of THF (12 mL), MeOH (4 mL) and H$_2$O (4 mL) was added LiOH—H$_2$O (163 mg, 3.88 mmol). The yellow solution was stirred overnight at rt at which point TLC analysis indicated complete consumption of the starting material. The reaction was quenched by the addition of 1 M HCl(aq) (30 mL), and the product was extracted with EtOAc (3×30 mL). The combined organic extracts were dried (Na$_2$SO$_4$) and concentrated in vacuo to provide 196 mg (0.400 mmol, 79%) of pure acid (RE5-3a) as a beige solid.

Step 5(c)

A solution of the acid (180 mg, 0.368 mmol), PyBOP (478 mg, 0.919 mmol), acyl hydrazide (82 mg, 1.1 mmol) and DIPA (0.157 mL, 1.10 mmol) in DMF (5 mL) was heated at 80° C. overnight. The reaction was cooled to rt, diluted with 1:1 water/brine (50 mL) and extracted with EtOAc (50 mL). The organic extracts were dried (Na$_2$SO$_4$) and concentrated in vacuo. Purification by flash column chromatography (90:10 EtOAc:MeOH) provided 130 mg (0.238 mmol, 65%) of pure bis-acyl hydrazide (RE5-3b) as a white solid.

Step 5(d)

To a solution of the bis-acyl hydrazide (113 mg, 0.207 mmol) in DCM (2 mL) was added pyridine (0.042 mL, 0.518 mmol). The solution was cooled to −10° C. (ice bath with NaCl), then triflic anhydride (0.077 mL, 0.456 mmol) was added (solution turned bright orange) and the mixture was gradually warmed to rt overnight. The reaction was quenched by the addition of sat. NaHCO$_3$ (30 mL) and extract with DCM (3×30 mL). The combined organic extracts were dried (Na$_2$SO$_4$) and concentrated in vacuo. Purification by flash column chromatography (100% EtOAc) provided 53 mg (0.100 mmol, 48%) of pure oxadiazole (RE5-3c).

Step 6(a) and (b): RE 6b and RE 6c

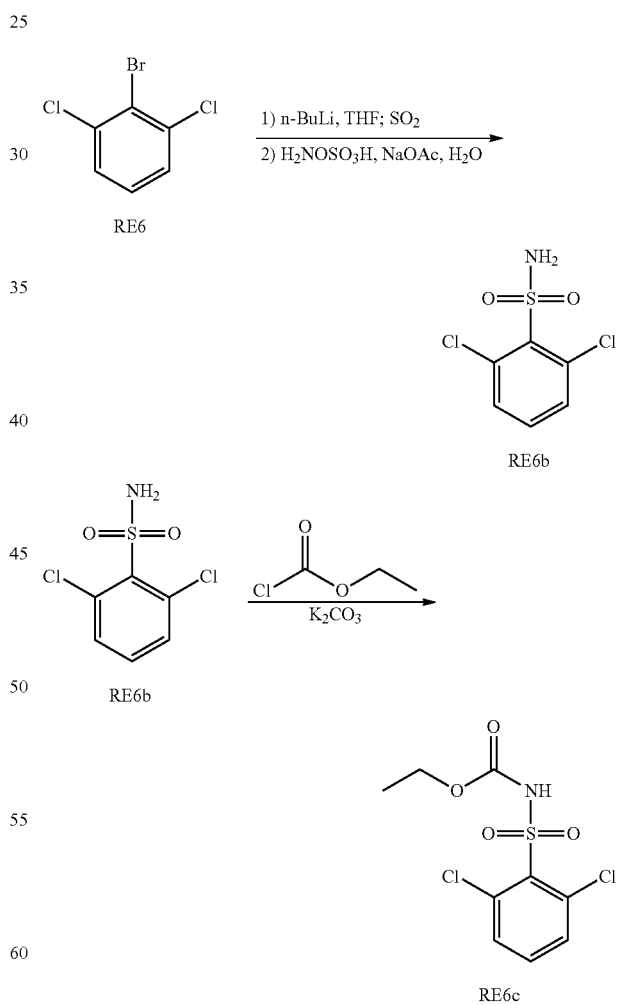

Step 6(a)

To a solution of 1-bromo-2,6-dichlorobenzene (4.34 g, 19.2 mmol) in THF (20 mL) at −78° C. was added n-BuLi (1.6

M in hexanes, 10.0 mL, 16.0 mmol). The reaction mixture (precipitate formed with time) was stirred at −78° C. for 4 hours. Sulfur dioxide was then bubbled into the mixture for 15 min The yellow solution was warmed to RT, during which time a colorless precipitate formed. After 30 min at RT, hexanes was added and the sulfinic salt was removed by filtration. The salt was dissolved in water (50 mL) and sodium acetate (3.28 g, 40.0 mmol) was added. The solution was cooled to 10° C. and hydroxylamine-O-sulfonic acid (2.26 g, 20.0 mmol) was added. The ice-water bath was removed, and a white product precipitated out within minutes. The reaction was stirred at RT overnight. The reaction was extracted with EtOAc (3×50 mL), and the combined organic layers were washed with 5% NaHCO$_3$(aq) (50 mL) and brine (50 mL), then dried (Na$_2$SO$_4$) and concentrated in vacuo to provide 2.66 g (11.8 mmol, 74%) of the sulfonamide (RE6b) as a white solid.

Step 6(b)

To a heterogeneous mixture of sulfonamide (14.5 g, 64.1 mmol) and potassium carbonate (31.0 g, 224 mmol) in acetone (130 mL) was added ethyl chloroformate (15.4 mL, 160 mmol). The reaction was heated to reflux overnight, then cooled to rt, and quenched by the addition of 200 mL 1 N HCl(aq). The product was extracted with EtOAc (3×200 mL), and the combined organic extracts were dried (Na$_2$SO$_4$) and concentrated in vacuo to provide 18.8 g (63.1 mmol, 98%) of pure sulfonyl carbamate (RE6c) as a white solid.

Step 7: RE 7-3

To a pink solution of carbamate (53 mg, 0.10 mmol) in DCM (2 mL) was added TFA (2 mL). The reaction turned yellow and MS indicated complete conversion after 5 minutes. The reaction was concentrated and the yellow oil was used without purification in the next reaction. To a solution of this ammonium salt and triethylamine (0.070 mL, 0.50 mmol) in DCM (3 mL) was added the isocyanate (0.018 mL, 0.12 mmol). The solution was refluxed for 4 hrs then cooled to rt. In vacuo concentration and purification by flash column chromatography (99:1 EtOAc, AcOH) provided 44 mg (0.068 mmol, 68%) of the desired sulfonylurea as a yellow solid. A solution of the sulfonylurea in 1:1 THF/ethanol (4 mL) was added sodium hydroxide (10N, 8.1 µL, 0.081 mmol). The bright yellow solution was stirred for 1 hour. The organic solvent was concentrated and the remaining yellow solid was dissolved in water (2 mL), frozen with liquid nitrogen and lyophilized for 24 hours to provide 44 mg of the desired sodium salt (3-1) as a yellow solid. (MS 644.9 (M+H)).

Compounds (Examples 3-2 through 3-5) were prepared in a similar manner as the compound, Example 3-1, but using the appropriate lactams to generate the desired compounds.

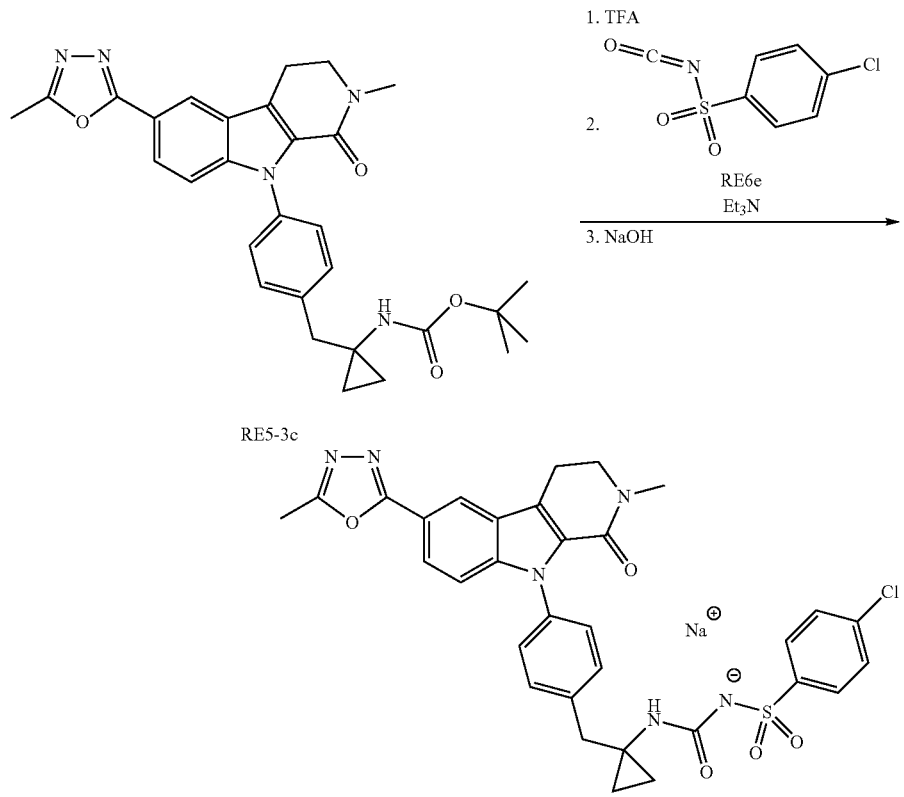

TABLE 3

| Ex | IUPAC name | Structure | MS |
|---|---|---|---|
| 3-1 | sodium [(4-chlorophenyl)sulfonyl]{[(1-{4-[2-methyl-6-(5-methyl-1,3,4-oxadiazol-2-yl)-1-oxo-1,2,3,4-tetrahydro-9H-beta-carbolin-9-yl]benzyl}cyclopropyl)amino]carbonyl}azanide | 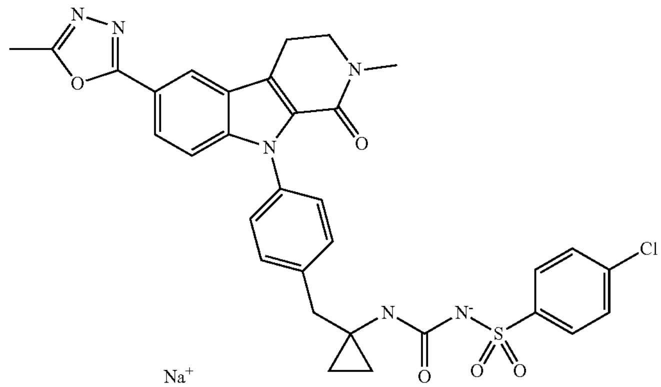 [SMILES: Cc1nnc(-c2ccc3c(c2)c2c(n3-c3ccc(CC4(NC(=O)[N-]S(=O)(=O)c5ccc(Cl)cc5)CC4)cc3)C(=O)N(C)CC2)o1 ; [Na+]] | 644.9 (M + H) |
| 3-2 | methyl 9-[4-({1-[({[(4-chlorophenyl)sulfonyl]amino}carbonyl)amino]cyclopropyl}methyl)phenyl]-2-methyl-1-oxo-2,3,4,9-tetrahydro-1H-beta-carboline-6-carboxylate | 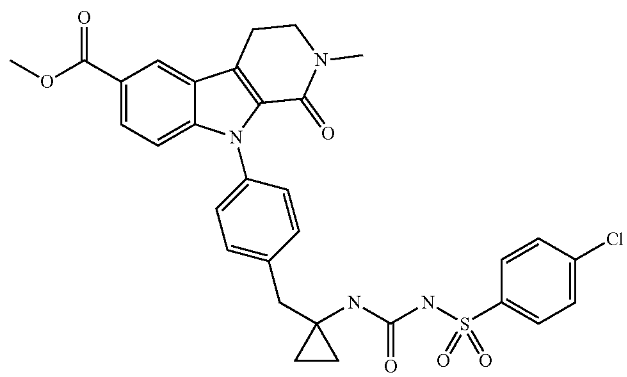 [SMILES: COC(=O)c1ccc2c(c1)c1c(n2-c2ccc(CC3(NC(=O)NS(=O)(=O)c4ccc(Cl)cc4)CC3)cc2)C(=O)N(C)CC1] | 622.1 (M + H) |
| 3-3 | 9-[4-({1-[({[(4-chlorophenyl)sulfonyl]amino}carbonyl)amino]cyclopropyl}methyl)phenyl]-2-methyl-1-oxo-2,3,4,9-tetrahydro-1H-beta-carboline-6-carboxylic acid | 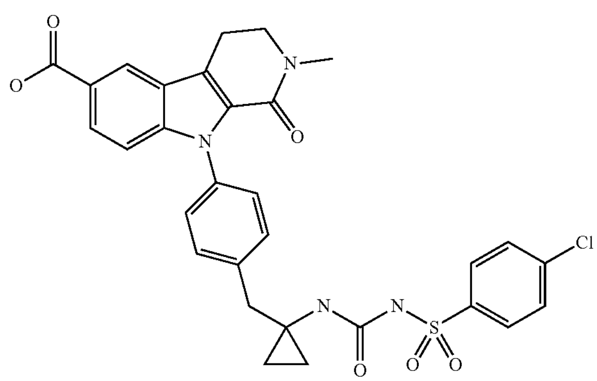 [SMILES: CN1CCc2c(n(-c3ccc(CC4(NC(=O)NS(=O)(=O)c5ccc(Cl)cc5)CC4)cc3)c3ccc(C(=O)O)cc23)C1=O] | 605.1 (M − H) |
| 3-4 | 4-chloro-N-{[(1-{4-[2-methyl-1-oxo-6-(1H-pyrazol-5-yl)-1,2,3,4-tetrahydro-9H-beta-carbolin-9-yl]benzyl}cyclopropyl)amino]carbonyl}benzenesulfonamide | 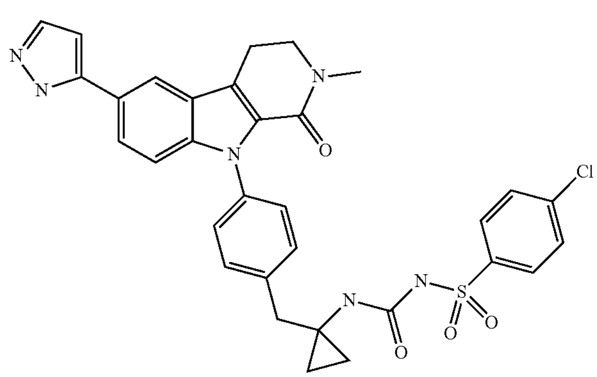 [SMILES: CN1CCc2c(n(-c3ccc(CC4(NC(=O)NS(=O)(=O)c5ccc(Cl)cc5)CC4)cc3)c3ccc(-c4ccn[nH]4)cc23)C1=O] | 651.1 (M + Na) |

TABLE 3-continued

| Ex | IUPAC name | Structure | MS |
|---|---|---|---|
| 3-5 | 4-chloro-N-{[(1-{4-[2-methyl-1-oxo-6-(5-phenyl-1,3,4-oxadiazol-2-yl)-1,2,3,4-tetrahydro-9H-beta-carbolin-9-yl]benzyl}cyclopropyl)amino]carbonyl}benzenesulfonamide | 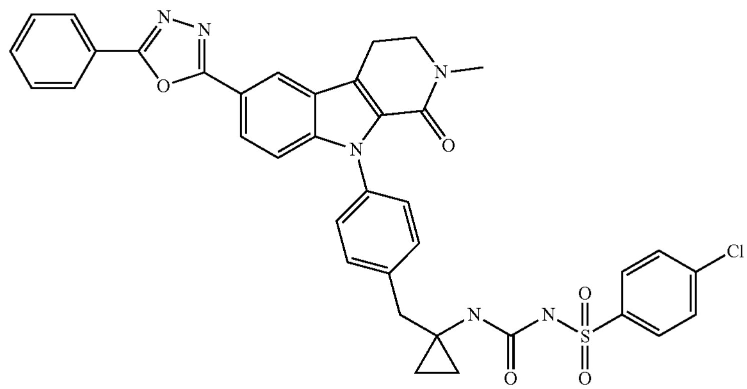 [SMILES: CN1CCc2c(n(-c3ccc(CC4(NC(=O)NS(=O)(=O)c5ccc(Cl)cc5)CC4)cc3)c3ccc(-c4nnc(-c5ccccc5)o4)cc23)C1=O] | 707.1 (M + H) |

Assays For Determining Biological Activity

The compounds of Formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Agonist and Antagonist Assays

Whole cell second messenger assays measuring stimulation of intracellular cAMP accumulation in HEK-293(ebna)-hEP4 cells are performed to determine whether receptor ligands are agonists or antagonists. Cells are harvested and resuspended in HBSS containing 25 mM HEPES, pH 7.4. Incubations contain 0.5 mM IBMX (phosphodiesterase inhibitor, available from Biomol). Samples are incubated at 37° C. for 10 min, the reaction is terminated and cAMP levels are then measured. Ligands are added in DMSO which is kept constant at 1% (v/v; agonists) or 2% (v/v; antagonists) in all incubations. For agonists, second messenger responses are expressed as a function of ligand concentration and both $EC_{50}$ values and the maximum response as compared to a $PGE_2$ standard are calculated. For antagonists, the ability of a ligand to inhibit an agonist response is determined by carrying out dose-response curves in the presence of $PGE_2$ agonist at a concentration corresponding to its $EC_{50}$. $IC_{50}$ values are calculated as the concentration of ligand required to inhibit 50% of the $PGE_2$-induced activity.

Rat Paw Edema Assay

The method is the same as described in Chan et al (J. Pharmacol. Exp. Ther. 274: 1531-1537, 1995) incorporated by reference in its entirety, herein.

Acute Inflammatory Hyperalgesia Induced by Carrageenan in Rats

The method is the same as described in Boyce et al (Neuropharmacology 33: 1609-1611, 1994) incorporated by reference in its entirety, herein.

Adjuvant-Induced Arthritis in Rats

Female Lewis rats (body weight approximately 146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.001-10.0 mg/kg) such that the body weights were equivalent within each group. Six groups of 10 rats each are injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) are determined before (day −1) and 17 to 21 days following adjuvant injection, and primary paw volumes are determined before (day −1) and on days 4 and 17 to 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 17-21 using the Faxitron (45 kVp, 30 seconds) and Kodak X-OMAT TL film, and are developed in an automatic processor. Radiographs are evaluated for changes in the soft and hard tissues by an investigator who was blinded to experimental treatment. The following radiographic changes are graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria are used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 17 to 21 days. The compounds are prepared weekly, refrigerated in the dark until used, and vortex mixed immediately prior to administration.

Prostanoid Receptor Binding Assays

Transfected HEK 293(ebna) cells are maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP1, EP2, EP3-III, EP4, FP, IP, and TP) are performed in 10 mM MES/KOH (pH 6.0) (EPs, FP and TP) or 10 mM HEPES/KOH (pH 7.4) (DPs and IP), containing 1 mM EDTA, 2.5-30 mM divalent cation and the appropriate radio-ligand. Synthetic compounds are added in DMSO which is kept constant at 1% (v/v) in all incubations. The reaction is initiated by addition of membrane protein. Non-specific binding is determined in the presence of 10 μM of the corresponding non-radioactive prostanoid. Incubations are conducted for 60-120 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves. The binding affinity of the compounds is determined by calculating the equilibrium inhibition constant ($K_i$) from the equation $K_i$=InPt/1+[radio-ligand]/$K_d$ where $K_d$ is the equilibrium dissociation constant for the radio-ligand:receptor interaction and InPt is the inflection point of the dose-response curves.

The compounds that are the subject of the present invention show $IC_{50}$ values ranging from about 20 nm to about 0.20 nm, as determined by the radioligand displacement binding assay. Abramovitz, M. et al., Biochem, Biophys. Acta, 2000, 1483, pp. 285. Examples 1-1, 1-7, and 1-32 have $IC_{50}$s ranging from about 5 nm to about 1 nm. Examples 1-9, 1-18, 1-20, and 1-33 have $IC_{50}$s greater than 5 nm. The remaining Examples have $IC_{50}$s less than 1 nm.

TABLE 4

| Ex | IUPAC name | $IC_{50}$ (nm) X > 5 | $IC_{50}$ (nm) 1 < X < 5 | $IC_{50}$ (nm) X < 1 |
|---|---|---|---|---|
| 1-1 | 4-chloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | | X | |
| 1-2 | 4-methyl-N-[({2-[4-(2,5,7-trimethyl-1-oxo-1,2,3,4-tetrahydro-9H-beta-carbolin-9-yl)phenyl]ethyl}amino)carbonyl] benzenesulfonamide | | | X |
| 1-3 | 4-chloro-N-[({2-[4-(5,7-dichloro-2-methyl-1-oxo-1,2,3,4-tetrahydro-9H-beta-carbolin-9-yl)phenyl]ethyl}amino)carbonyl]benzenesulfonamide | | | X |
| 1-4 | 4-chloro-N-[({2-[4-(6-chloro-2-methyl-1-oxo-1,2,3,4-tetrahydro-9H-beta-carbolin-9-yl)phenyl]ethyl}amino)carbonyl]benzenesulfonamide | | | X |
| 1-5 | N-[({2-[4-(6-bromo-2-methyl-1-oxo-1,2,3,4-tetrahydro-9H-beta-carbolin-9-yl)phenyl]ethyl}amino)carbonyl]-4-chlorobenzenesulfonamide | | | X |
| 1-6 | 4-chloro-N-[({2-[4-(5,7-dichloro-2-ethyl-1-oxo-1,2,3,4-tetrahydro-9H-beta-carbolin-9-yl)phenyl]ethyl}amino)carbonyl]benzenesulfonamide | | | X |
| 1-7 | 4-chloro-N-{[(2-{4-[5,7-dichloro-2-(cyclopropylmethyl)-1-oxo-1,2,3,4-tetrahydro-9H-beta-carbolin-9-yl]phenyl}ethyl)amino]carbonyl}benzenesulfonamide | | X | |
| 1-8 | 4-chloro-N-[({2-[4-(2-methyl-1-oxo-6-phenyl-1,2,3,4-tetrahydro-9H-beta-carbolin-9-yl)phenyl]ethyl}amino)carbonyl]benzenesulfonamide | | | X |
| 1-9 | 4-chloro-N-[({2-[4-(5,7-dichloro-1-oxo-2-phenyl-1,2,3,4-tetrahydro-9H-beta-carbolin-9-yl)phenyl]ethyl}amino)carbonyl]benzenesulfonamide | X | | |
| 1-10 | 4-chloro-N-[({2-[4-(6,7-dichloro-2-methyl-1-oxo-1,2,3,4-tetrahydro-9H-beta-carbolin-9-yl)phenyl]ethyl}amino)carbonyl]benzenesulfonamide | | | X |
| 1-11 | 4-chloro-N-[({2-[4-(5,6-dichloro-2-methyl-1-oxo-1,2,3,4-tetrahydro-9H-beta-carbolin-9-yl)phenyl]ethyl}amino)carbonyl]benzenesulfonamide | | | X |
| 1-12 | 4-chloro-N-[({2-[4-(7-chloro-2-methyl-1-oxo-1,2,3,4-tetrahydro-9H-beta-carbolin-9-yl)phenyl]ethyl}amino)carbonyl]benzenesulfonamide | | | X |
| 1-13 | 4-chloro-N-[({2-[4-(5-chloro-2-methyl-1-oxo-1,2,3,4-tetrahydro-9H-beta-carbolin-9-yl)phenyl]ethyl}amino)carbonyl]benzenesulfonamide | | | X |
| 1-14 | N-[({2-[4-(5-bromo-2-methyl-1-oxo-1,2,3,4-tetrahydro-9H-beta-carbolin-9-yl)phenyl]ethyl}amino)carbonyl]-4-chlorobenzenesulfonamide | | | X |
| 1-15 | N-[({2-[4-(7-bromo-2-methyl-1-oxo-1,2,3,4-tetrahydro-9H-beta-carbolin-9-yl)phenyl]ethyl}amino)carbonyl]-4-chlorobenzenesulfonamide | | | X |
| 1-16 | N-[({1-[4-(6-bromo-2-methyl-1-oxo-1,2,3,4-tetrahydro-9H-beta-carbolin-9-yl)benzyl]cyclopropyl}amino)carbonyl]-4-chlorobenzenesulfonamide | | | X |
| 1-17 | 4-chloro-N-[({2-[4-(2-methyl-1-oxo-5-phenyl-1,2,3,4-tetrahydro-9H-beta-carbolin-9-yl)phenyl]ethyl}amino)carbonyl]benzenesulfonamide | | | X |

TABLE 4-continued

| Ex | IUPAC name | IC$_{50}$ (nm) X > 5 | IC$_{50}$ (nm) 1 < X < 5 | IC$_{50}$ (nm) X < 1 |
|---|---|---|---|---|
| 1-18 | 4-chloro-N-[({2-[4-(2-methyl-1-oxo-7-phenyl-1,2,3,4-tetrahydro-9H-beta-carbolin-9-yl)phenyl]ethyl}amino)carbonyl]benzenesulfonamide | X | | |
| 1-19 | 4-chloro-N-{[(2-{4-[6-(4-fluorophenyl)-2-methyl-1-oxo-1,2,3,4-tetrahydro-9H-beta-carbolin-9-yl]phenyl}ethyl)amino]carbonyl}benzenesulfonamide | | | X |
| 1-20 | 4-chloro-N-[({2-[4-(8-chloro-2-methyl-1-oxo-1,2,3,4-tetrahydro-9H-beta-carbolin-9-yl)phenyl]ethyl}amino)carbonyl]benzenesulfonamide | X | | |
| 1-21 | 4-chloro-N-[({2-[4-(2-methyl-1-oxo-6-pyridin-3-yl-1,2,3,4-tetrahydro-9H-beta-carbolin-9-yl)phenyl]ethyl}amino)carbonyl]benzenesulfonamide | | | X |
| 1-22 | 4-chloro-N-[({2-[4-(2-methyl-1-oxo-6-pyridin-2-yl-1,2,3,4-tetrahydro-9H-beta-carbolin-9-yl)phenyl]ethyl}amino)carbonyl]benzenesulfonamide | | | X |
| 1-23 | 4-chloro-N-{[(1-{4-[6-(2-fluorophenyl)-2-methyl-1-oxo-1,2,3,4-tetrahydro-9H-beta-carbolin-9-yl]benzyl}cyclopropyl)amino]carbonyl}benzenesulfonamide | | | X |
| 1-24 | 4-chloro-N-[({1-[4-(2-methyl-1-oxo-6-pyridin-3-yl-1,2,3,4-tetrahydro-9H-beta-carbolin-9-yl)benzyl]cyclopropyl}amino)carbonyl]benzenesulfonamide | | | X |
| 1-25 | 4-chloro-N-{[(1-{4-[2-methyl-1-oxo-6-(3-thienyl)-1,2,3,4-tetrahydro-9H-beta-carbolin-9-yl]benzyl}cyclopropyl)amino]carbonyl}benzenesulfonamide | | | X |
| 1-26 | 4-chloro-N-[({1-[4-(2-methyl-1-oxo-6-pyridin-2-yl-1,2,3,4-tetrahydro-9H-beta-carbolin-9-yl)benzyl]cyclopropyl}amino)carbonyl]benzenesulfonamide | | | X |
| 1-27 | 4-chloro-N-{[(1-{4-[2-methyl-6-(2-methylphenyl)-1-oxo-1,2,3,4-tetrahydro-9H-beta-carbolin-9-yl]benzyl}cyclopropyl)amino]carbonyl}benzenesulfonamide | | | X |
| 1-28 | 4-chloro-N-[({1-[4-(2,5,7-trimethyl-1-oxo-1,2,3,4-tetrahydro-9H-beta-carbolin-9-yl)benzyl]cyclopropyl}amino)carbonyl]benzenesulfonamide | | | X |
| 1-29 | 2,6-dichloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | | | X |
| 1-30 | 2,6-dimethoxy-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide | | | X |
| 1-31 | 4-chloro-N-{[(2-{4-[2-methyl-6-(methylsulfonyl)-1-oxo-1,2,3,4-tetrahydro-9H-beta-carbolin-9-yl]phenyl}ethyl)amino]carbonyl}benzenesulfonamide | | | X |
| 1-32 | 4-chloro-N-{[(2-{4-[2-methyl-7-(methylsulfonyl)-1-oxo-1,2,3,4-tetrahydro-9H-beta-carbolin-9-yl]phenyl}ethyl)amino]carbonyl}benzenesulfonamide | | X | |
| 1-33 | 4-chloro-N-{[(2-{4-[2-methyl-5-(methylsulfonyl)-1-oxo-1,2,3,4-tetrahydro-9H-beta-carbolin-9-yl]phenyl}ethyl)amino]carbonyl}benzenesulfonamide | X | | |
| 1-34 | 4-chloro-N-{[(1-{4-[2-methyl-6-(methylsulfonyl)-1-oxo-1,2,3,4-tetrahydro-9H-beta-carbolin-9-yl]benzyl}cyclopropyl)amino]carbonyl}benzenesulfonamide | | | X |
| 1-35 | 4-chloro-N-({[2-(4-{2-methyl-6-[4-(methylsulfonyl)phenyl]-1-oxo-1,2,3,4-tetrahydro-9H-beta-carbolin-9-yl}phenyl)ethyl]amino}carbonyl)benzenesulfonamide | | | X |
| 1-36 | 4-chloro-N-({[2-(4-{2-methyl-6-[3-(methylsulfonyl)phenyl]-1-oxo-1,2,3,4-tetrahydro-9H-beta-carbolin-9-yl}phenyl)ethyl]amino}carbonyl)benzenesulfonamide | | | X |
| 1-37 | 4-chloro-N-{[(1-{4-[2-methyl-1-oxo-6-(phenylsulfonyl)-1,2,3,4-tetrahydro-9H-beta-carbolin-9-yl]benzyl}cyclopropyl)amino]carbonyl}benzenesulfonamide | | | X |
| 2-1 | 4-chloro-N-[({1-[4-(6-cyclopropyl-2-methyl-1-oxo-1,2,3,4-tetrahydro-9H-beta-carbolin-9-yl)benzyl]cyclopropyl}amino)carbonyl]benzenesulfonamide | | | X |
| 2-2 | 4-chloro-N-[({2-[4-(6-cyclopropyl-2-methyl-1-oxo-1,2,3,4-tetrahydro-9H-beta-carbolin-9-yl)phenyl]ethyl}amino)carbonyl]benzenesulfonamide | | | X |
| 2-3 | 4-chloro-N-[({2-[4-(5-cyclopropyl-2-methyl-1-oxo-1,2,3,4-tetrahydro-9H-beta-carbolin-9-yl)phenyl]ethyl}amino)carbonyl]benzenesulfonamide | | | X |
| 2-4 | 4-chloro-N-[({2-[4-(7-cyclopropyl-2-methyl-1-oxo-1,2,3,4-tetrahydro-9H-beta-carbolin-9-yl)phenyl]ethyl}amino)carbonyl]benzenesulfonamide | | | X |

TABLE 4-continued

| Ex | IUPAC name | IC$_{50}$ (nm) X > 5 | IC$_{50}$ (nm) 1 < X < 5 | IC$_{50}$ (nm) X < 1 |
|---|---|---|---|---|
| 3-1 | sodium [(4-chlorophenyl)sulfonyl]{[(1-{4-[2-methyl-6-(5-methyl-1,3,4-oxadiazol-2-yl)-1-oxo-1,2,3,4-tetrahydro-9H-beta-carbolin-9-yl]benzyl}cyclopropyl)amino]carbonyl} azanide | | | X |
| 3-2 | methyl 9-[4-({1-[({[(4-chlorophenyl)sulfonyl]amino}carbonyl)amino]cyclopropyl}methyl)phenyl]-2-methyl-1-oxo-2,3,4,9-tetrahydro-1H-beta-carboline-6-carboxylate | | | X |
| 3-3 | 9-[4-({1-[({[(4chlorophenyl)sulfonyl]amino}carbonyl)amino] cyclopropyl}methyl)phenyl]-2-methyl-1-oxo-2,3,4,9-tetrahydro-1H-beta-carboline-6-carboxylic acid | | | X |
| 3-4 | 4-chloro-N-{[(1-{4-[2-methyl-1-oxo-6-(1H-pyrazol-5-yl)-1,2,3,4-tetrahydro-9H-beta-carbolin-9-yl]benzyl}cyclopropyl)amino]carbonyl}benzenesulfonamide | | | X |
| 3-5 | 4-chloro-N-{[(1-{4-[2-methyl-1-oxo-6-(5-phenyl-1,3,4-oxadiazol-2-yl)-1,2,3,4-tetrahydro-9H-beta-carbolin-9-yl]benzyl}cyclopropyl)amino]carbonyl}benzenesulfonamide | | | X |

What is claimed is:

1. A compound of Formula I and pharmaceutically acceptable salts and solvates thereof,

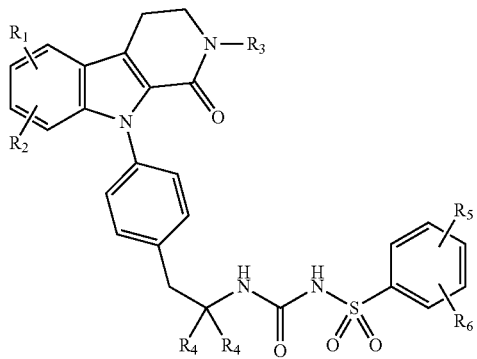

Formula I wherein:

x is 0, 1, or 2;
y is 0, 1, or 2;
n is 1, 2, 3, 4, 5 or 6;
$R_1$, $R_2$ are each independently selected from hydrogen, halogen, $C_{1-6}$ alkyl, $C_{3-6}$ cycloalkyl, aryl, heteroaryl, $NR_aR_b$, $S(O)_xR_a$, $C(O)_yR_a$, and $OR_a$, wherein said alkyl, cycloalkyl, aryl, and heteroaryl are optionally substituted with one or more substituents $R_7$;
$R_3$ is selected from hydrogen, $C_{1-6}$ alkyl, $C_{3-6}$ cycloalkyl, aryl, and heteroaryl, wherein said alkyl, cycloalkyl, aryl, and heteroaryl are optionally substituted with one or more substituents $R_7$;
$R_4$ is hydrogen or the two $R_4$ groups are $(CH_2)_n$ and together with the carbon atom to which they are attached form a 3 to 6 membered ring;
$R_5$, $R_6$ are each independently selected from hydrogen, halogen, $C_{1-6}$ alkyl, $C_{3-6}$ cycloalkyl, aryl, heteroaryl, $NR_aR_b$, $S(O)_xR_a$, and $OR_a$, wherein said alkyl, cycloalkyl, aryl, and heteroaryl are optionally substituted with one or more substituents $R_7$;
$R_a$, $R_b$ are each independently selected from hydrogen, hydroxy, $C_{1-6}$ alkyl, $C_{1-6}$ alkoxy, $C_{3-10}$ cycloalkyl, aryl, and heterocyclyl, wherein said alkyl, cycloalkyl, aryl and heterocyclyl are optionally substituted with one or more substituents $R_7$;
$R_7$ is selected from hydroxy, aryl, halogen, —$C_{1-6}$ alkyl, $C_{1-6}$ alkoxy, hydrogen, $S(O)_xR_a$, and $C_{3-6}$cycloalkyl.

2. A compound according to claim 1 wherein $R_1$, $R_2$ are each independently selected from hydrogen, halogen, $C_{1-4}$ alkyl, $C_{3-6}$ cycloalkyl, aryl, heteroaryl, $C(O)_yRa$, and $S(O)_xRa$, wherein said aryl and heteroaryl groups are optionally substituted with one or more $R_7$.

3. A compound according to claim 1 wherein $R_3$ is selected from hydrogen, $C_{1-6}$ alkyl, $C_{3-6}$ cycloalkyl, and aryl.

4. A compound according to claim 1 wherein $R_4$ is hydrogen.

5. A compound according to claim 1 wherein $R_5$, $R_6$ are each independently selected from hydrogen, halogen, $C_{1-6}$ alkyl, $C_{3-6}$ cycloalkyl, and $OC_{1-4}$ alkyl.

6. A compound according to claim 1 wherein $R_7$ is selected from hydrogen, halogen, $C_{1-4}$ alkyl, and phenyl.

7. A compound according to claim 2 wherein $R_3$ is selected from hydrogen, $C_{1-6}$ alkyl, $C_{3-6}$ cycloalkyl, and aryl.

8. A compound according to claim 2 wherein the two $R_4$ groups are $(CH_2)_n$ and together with the carbon atom to which they are attached form a 3 to 6 membered ring.

9. A compound according to claim 2 wherein $R_5$, $R_6$ are each independently selected from hydrogen, halogen, $C_{1-6}$ alkyl, $C_{3-6}$ cycloalkyl, and $OC_{1-4}$ alkyl.

10. A compound according to claim 2 wherein $R_7$ is selected from hydrogen, halogen, $C_{1-4}$ alkyl, and phenyl.

11. A compound according to claim 7 wherein $R_5$, $R_6$ are each independently selected from hydrogen, halogen, $C_{1-6}$ alkyl, $C_{3-6}$ cycloalkyl, and $OC_{1-4}$ alkyl.

12. A compound selected from the group consisting of:
4-chloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;
4-methyl-N-[({2-[4-(2,5,7-trimethyl-1-oxo-1,2,3,4-tetrahydro-9H-beta-carbolin-9-yl)phenyl]ethyl}amino)carbonyl]benzenesulfonamide;
4-chloro-N-[({2-[4-(5,7-dichloro-2-methyl-1-oxo-1,2,3,4-tetrahydro-9H-beta-carbolin-9-yl)phenyl]ethyl}amino)carbonyl]benzenesulfonamide;
4-chloro-N-[({2-[4-(6-chloro-2-methyl-1-oxo-1,2,3,4-tetrahydro-9H-beta-carbolin-9-yl)phenyl]ethyl}amino)carbonyl]benzenesulfonamide;

N-[({2-[4-(6-bromo-2-methyl-1-oxo-1,2,3,4-tetrahydro-9H-beta-carbolin-9-yl)phenyl]ethyl}amino)carbonyl]-4-chlorobenzenesulfonamide;

4-chloro-N-[({2-[4-(5,7-dichloro-2-ethyl-1-oxo-1,2,3,4-tetrahydro-9H-beta-carbolin-9-yl)phenyl]ethyl}amino)carbonyl]benzenesulfonamide;

4-chloro-N-{[(2-{4-[5,7-dichloro-2-(cyclopropylmethyl)-1-oxo-1,2,3,4-tetrahydro-9H-beta-carbolin-9-yl]phenyl}ethyl)amino]carbonyl}benzenesulfonamide;

4-chloro-N-[({2-[4-(2-methyl-1-oxo-6-phenyl-1,2,3,4-tetrahydro-9H-beta-carbolin-9-yl)phenyl]ethyl}amino)carbonyl]benzenesulfonamide;

4-chloro-N-[({2-[4-(5,7-dichloro-1-oxo-2-phenyl-1,2,3,4-tetrahydro-9H-beta-carbolin-9-yl)phenyl]ethyl}amino)carbonyl]benzenesulfonamide;

4-chloro-N-[({2-[4-(6,7-dichloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5,6-dichloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(7-chloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5-chloro-2-methyl-1-oxo-1,2,3,4-tetrahydro-9H-beta-carbolin-9-yl)phenyl]ethyl}amino)carbonyl]benzenesulfonamide;

N-[({2-[4-(5-bromo-2-methyl-1-oxo-1,2,3,4-tetrahydro-9H-beta-carbolin-9-yl)phenyl]ethyl}amino)carbonyl]-4-chlorobenzenesulfonamide;

N-[({2-[4-(7-bromo-2-methyl-1-oxo-1,2,3,4-tetrahydro-9H-beta-carbolin-9-yl)phenyl]ethyl}amino)carbonyl]-4-chlorobenzenesulfonamide;

N-[({1-[4-(6-bromo-2-methyl-1-oxo-1,2,3,4-tetrahydro-9H-beta-carbolin-9-yl)benzyl]cyclopropyl}amino)carbonyl]-4-chlorobenzenesulfonamide;

4-chloro-N-[({2-[4-(2-methyl-1-oxo-5-phenyl-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-7-phenyl-1,2,3,4-tetrahydro-9H-beta-carbolin-9-yl)phenyl]ethyl}amino)carbonyl]benzenesulfonamide;

4-chloro-N-{[(2-{4-[6-(4-fluorophenyl)-2-methyl-1-oxo-1,2,3,4-tetrahydro-9H-beta-carbolin-9-yl]phenyl}ethyl)amino]carbonyl}benzenesulfonamide;

4-chloro-N-[({2-[4-(8-chloro-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-6-pyridin-3-yl-1,2,3,4-tetrahydro-9H-beta-carbolin-9-yl)phenyl]ethyl}amino)carbonyl]benzenesulfonamide;

4-chloro-N-[({2-[4-(2-methyl-1-oxo-6-pyridin-2-yl-1,2,3,4-tetrahydro-9H-beta-carbolin-9-yl)phenyl]ethyl}amino)carbonyl]benzenesulfonamide;

4-chloro-N-{[(1-{4-[6-(2-fluorophenyl)-2-methyl-1-oxo-1,2,3,4-tetrahydro-9H-beta-carbolin-9-yl]benzyl}cyclopropyl)amino]carbonyl}benzenesulfonamide;

4-chloro-N-[({1-[4-(2-methyl-1-oxo-6-pyridin-3-yl-1,2,3,4-tetrahydro-9H-beta-carbolin-9-yl)benzyl]cyclopropyl}amino)carbonyl]benzenesulfonamide;

4-chloro-N-{[(1-{4-[2-methyl-1-oxo-6-(3-thienyl)-1,2,3,4-tetrahydro-9H-beta-carbolin-9-yl]benzyl}cyclopropyl)amino]carbonyl}benzenesulfonamide;

4-chloro-N-[({1-[4-(2-methyl-1-oxo-6-pyridin-2-yl-1,2,3,4-tetrahydro-9H-beta-carbolin-9-yl)benzyl]cyclopropyl}amino)carbonyl]benzenesulfonamide;

4-chloro-N-{[(1-{4-[2-methyl-6-(2-methylphenyl)-1-oxo-1,2,3,4-tetrahydro-9H-beta-carbolin-9-yl]benzyl}cyclopropyl)amino]carbonyl}benzenesulfonamide;

4-chloro-N-[({1-[4-(2,5,7-trimethyl-1-oxo-1,2,3,4-tetrahydro-9H-beta-carbolin-9-yl)benzyl]cyclopropyl}amino)carbonyl]benzenesulfonamide;

2,6-dichloro-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;

2,6-dimethoxy-N-[({1-[4-(2-methyl-1-oxo-6-phenyl-1,2,3,4-tetrahydro-9H-beta-carbolin-9-yl)benzyl]cyclopropyl}amino)carbonyl]benzenesulfonamide;

4-chloro-N-[({1-[4-(6-cyclopropyl-2-methyl-1-oxo-1,2,3,4-tetrahydro-9H-beta-carbolin-9-yl)benzyl]cyclopropyl}amino)carbonyl]benzenesulfonamide;

4-chloro-N-[({2-[4-(6-cyclopropyl-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(5-cyclopropyl-2-methyl-1-oxo-1,2,3,4-tetrahydro-9H-beta-carbolin-9-yl)phenyl]ethyl}amino)carbonyl]benzenesulfonamide;

4-chloro-N-[({2-[4-(7-cyclopropyl-2-methyl-1-oxo-1,2,3,4-tetrahydro-9H-beta-carbolin-9-yl)phenyl]ethyl}amino)carbonyl]benzenesulfonamide;

sodium[((4-chlorophenyl)sulfonyl]{[(1-{4-[2-methyl-6-(5-methyl-1,3,4-oxadiazol-2-yl)-1-oxo-1,2,3,4-tetrahydro-9H-beta-carbolin-9-yl]benzyl}cyclopropyl)amino]carbonyl}azanide;

4-chloro-N-{[(2-{4-[2-methyl-6-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(2-{4-[2-methyl-7-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(2-{-4-[2-methyl-5-(methylsulfonyl)-1-oxo-1,2,3,4-tetrahydro-9H-beta-carbolin-9-yl]phenyl}ethyl)amino]carbonyl}benzenesulfonamide;

4-chloro-N-{[(1-{4-[2-methyl-6-(methylsulfonyl)-1-oxo-1,2,3,4-tetrahydro-9H-beta-carbolin-9-yl]benzyl}cyclopropyl)amino]carbonyl}benzenesulfonamide;

4-chloro-N-({[2-(4-{2-methyl-6-[4-(methylsulfonyl)phenyl]-1-oxo-1,2,3,4-tetrahydro-9H-beta-carbolin-9-yl}phenyl)ethyl]amino}carbonyl)benzenesulfonamide;

4-chloro-N-({[2-(4-{2-methyl-6-[3-(methylsulfonyl)phenyl]-1-oxo-1,2,3,4-tetrahydro-9H-beta-carbolin-9-yl}phenyl)ethyl]amino}carbonyl)benzenesulfonamide;

methyl 9-[4-({1-[({[(4chlorophenyl)sulfonyl]amino}carbonyl)amino]cyclopropyl}methyl)phenyl]-2-methyl-1-oxo-2,3,4,9-tetrahydro-1H-beta-carboline-6-carboxylate;

9-[4-({1-[({[(4-chlorophenyl)sulfonyl]amino}carbonyl)amino]cyclopropyl}methyl)phenyl]-2-methyl-1-oxo-2,3,4,9-tetrahydro-1H-beta-carboline-6-carboxylic acid;

4-chloro-N-{[(1-{4-[2-methyl-1-oxo-6-(1H-pyrazol-5-yl)-1,2,3,4-tetrahydro-9H-beta-carbolin-9-yl]benzyl}cyclopropyl)amino]carbonyl}benzenesulfonamide;

4-chloro-N-{[(1-{4-[2-methyl-1-oxo-6-(5-phenyl-1,3,4-oxadiazol-2-yl)-1,2,3,4-tetrahydro-9H-beta-carbolin-9-yl]benzyl}cyclopropyl)amino]carbonyl}benzenesulfonamide;

4-chloro-N-{[(1-{-4-[2-methyl-1-oxo-6-(phenylsulfonyl)-1,2,3,4-tetrahydro-9H-beta-carbolin-9-yl]benzyl}cyclopropyl)amino]carbonyl}benzenesulfonamide; and pharmaceutically acceptable salts and solvates thereof.

13. A pharmaceutical composition comprising a compound of claim 1 in admixture with one or more pharmaceutically acceptable carriers or excipients.

14. A method of inhibiting an agonist response of PGE2 at EP4 receptor, the action of PGE2 at EP4 receptors, which method comprises administering to said subject an effective amount of a compound according to claim 1.

15. A compound of Formula I and pharmaceutically acceptable salts and solvates thereof,

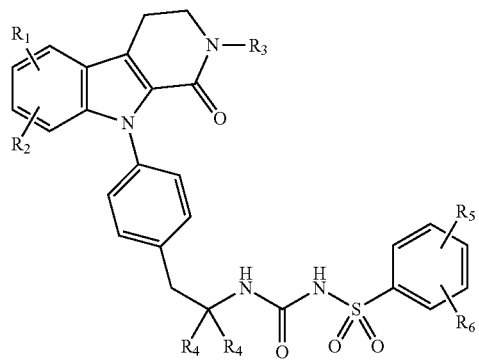

Formula I wherein:
x is 0, 1, or 2;
y is 0, 1, or 2;
n is 1, 2, or 3;
$R_1$, $R_2$ are each independently selected from hydrogen, halogen, $C_{1-4}$ alkyl, $C_{3-6}$ cycloalkyl, aryl, heteroaryl, $S(O)_xR_a$, and $C(O)_yR_a$, wherein said aryl and heteroaryl are optionally substituted with one or more substituents $R_7$;
$R_3$ is selected from hydrogen, $C_{1-6}$ alkyl, $C_{3-6}$ cycloalkyl, and aryl;
$R_4$ is hydrogen or the two $R_4$ groups are $(CH_2)_n$ and together with the carbon atom to which they are attached form a 3 to 6 membered ring;
$R_5$, $R_6$ are each independently selected from hydrogen, halogen, $C_{1-6}$ alkyl, $C_{3-6}$ cycloalkyl, and $OC_{1-4}$ alkyl;
$R_a$, $R_b$ are each independently selected from hydrogen, $C_{1-6}$ alkyl, $C_{3-10}$ cycloalkyl, aryl, and heterocyclyl, wherein said alkyl, cycloalkyl, aryl and heterocyclyl are optionally substituted with one or more substituents $R_7$; and
$R_7$ is selected from hydrogen, halogen, —$C_1$-4 alkyl, and phenyl.

16. A compound of Formula I and pharmaceutically acceptable salts and solvates thereof,

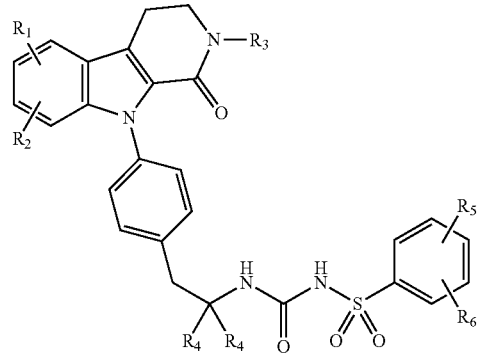

Formula I wherein:
x is 0, 1, or 2;
y is 0, 1, or 2;
n is 1, 2, or 3;
$R_1$, $R_2$ are each independently selected from hydrogen, halogen, $C_{1-3}$ alkyl, cyclopropyl, phenyl, benzyl, pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl, $C(O)_yR_a$, and $S(O)_xR_a$, wherein said phenyl and oxadiazolyl are optionally substituted with one or more $R_7$;
$R_3$ is selected from hydrogen, methyl, ethyl, cyclopropyl, cyclopropylmethyl, and phenyl;
$R_4$ is hydrogen or the two $R_4$ groups are $(CH_2)_n$ and together with the carbon atom to which they are attached form a 3 to 6 membered ring;
$R_5$, $R_6$ are each independently selected from hydrogen, chlorine, bromine, fluorine, methyl, ethyl, cyclopropyl, methoxyl, and ethoxyl;
$R_a$, $R_b$ are each independently selected from hydrogen, $C_{1-6}$ alkyl, $C_{3-10}$ cycloalkyl, aryl, and heterocyclyl, wherein said alkyl, cycloalkyl, aryl and heterocyclyl are optionally substituted with one or more substituents $R_7$; and
$R_7$ is selected from hydrogen, halogen, methyl, ethyl, and phenyl.

17. A compound of Formula I and pharmaceutically acceptable salts and solvates thereof,

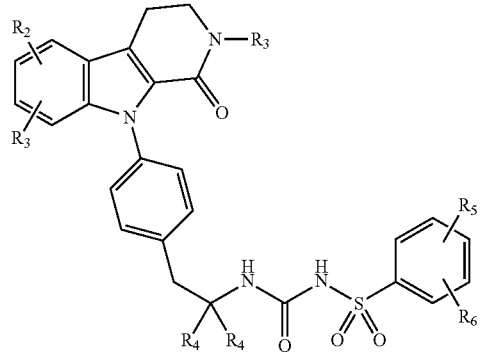

Formula I wherein:
  x is 0, 1, or 2;
  y is 0, 1, or 2;
  n is 1, 2, or 3;
  $R_1$, $R_2$ are each independently selected from hydrogen, methyl, cyclopropyl, chlorine, bromine, phenyl, pyridyl, thienyl (or thiophenyl), pyrazolyl, oxadiazolyl, $C(O)_y Ra$, and $S(O)_x Ra$, wherein said phenyl and oxadiazolyl are optionally substituted with one or more $R_7$;
  $R_3$ is selected from hydrogen, methyl, ethyl, cyclopropyl, cyclopropylmethyl, and phenyl;
  $R_4$ is hydrogen or the two $R_4$ groups are $(CH_2)_n$ and together with the carbon atom to which they are attached form a 3 to 6 membered ring;
  $R_5$, $R_6$ are each independently selected from hydrogen, chlorine, methyl, and methoxyl;
  $R_a$, $R_b$ are each independently selected from hydrogen, methyl, ethyl, and phenyl; and
  $R_7$ is selected from hydrogen, methyl, fluorine, and phenyl.

* * * * *

UNITED STATES PATENT AND TRADEMARK OFFICE
CERTIFICATE OF CORRECTION

PATENT NO. : 8,685,999 B2  Page 1 of 1
APPLICATION NO. : 13/120786
DATED : April 1, 2014
INVENTOR(S) : Berthelette et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 424 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,685,999 B2
APPLICATION NO. : 13/120786
DATED : April 1, 2014
INVENTOR(S) : Carl Berthelette et al.

It is certified that error appears in the above-identified patent and that said Letters Patent is hereby corrected as shown below:

On the Title Page

Item (73) Assignee:
- Delete "Merck Sharp & Dohme Corp.,
  Rahway, NJ (US)"
- Add "Merck Canada Inc.,
  Kirkland, Quebec (CA)"

Signed and Sealed this
Twenty-fifth Day of August, 2020

Andrei Iancu
*Director of the United States Patent and Trademark Office*